US008152904B2

(12) United States Patent
Slobodzian et al.

(10) Patent No.: US 8,152,904 B2
(45) Date of Patent: Apr. 10, 2012

(54) LIQUID DEGAS SYSTEM

(75) Inventors: Jonathan K. Slobodzian, Lynnwood, WA (US); Gregory T. Wing, Carnation, WA (US)

(73) Assignee: LipoSonix, Inc., Bothell, WA (US)

( * ) Notice: Subject to any disclaimer, the term of this patent is extended or adjusted under 35 U.S.C. 154(b) by 126 days.

(21) Appl. No.: 12/794,653

(22) Filed: Jun. 4, 2010

(65) Prior Publication Data

US 2011/0072970 A1    Mar. 31, 2011

Related U.S. Application Data

(60) Provisional application No. 61/246,937, filed on Sep. 29, 2009.

(51) Int. Cl.
*B01D 19/00* (2006.01)
*C02F 1/20* (2006.01)

(52) U.S. Cl. .............. 95/248; 95/266; 96/193; 96/194

(58) Field of Classification Search .............. 95/248, 95/266, 247, 249; 96/193, 194, 174
See application file for complete search history.

(56) References Cited

U.S. PATENT DOCUMENTS

| | | | |
|---|---|---|---|
| 2,773,555 A | 12/1956 | Pape | |
| 3,676,983 A | 7/1972 | Nold | |
| 3,722,180 A | 3/1973 | Boucher et al. | |
| 3,853,500 A | 12/1974 | Gassman et al. | |
| 4,216,089 A | 8/1980 | Boon et al. | |
| 4,300,919 A * | 11/1981 | Lewis et al. | 95/259 |
| 4,427,421 A | 1/1984 | Jensen et al. | |
| 4,935,151 A | 6/1990 | Do | |
| 5,508,975 A | 4/1996 | Walter | |
| 5,509,954 A | 4/1996 | Derian et al. | |
| 5,674,312 A | 10/1997 | Mazzei | |
| 5,865,995 A | 2/1999 | Nelson | |
| 5,879,314 A * | 3/1999 | Peterson et al. | 601/2 |
| 6,193,893 B1 | 2/2001 | Mazzei | |
| 6,290,760 B1 * | 9/2001 | Taivalkoski et al. | 96/195 |
| 6,338,749 B1 | 1/2002 | Fulk et al. | |

(Continued)

FOREIGN PATENT DOCUMENTS

WO    WO 00/74812 A1    12/2000

OTHER PUBLICATIONS

International Search Report and Written Opinion mailed on Nov. 23, 2010 for International Application No. PCT/US10/050274 filed on Sep. 24, 2010, 9 pages.

*Primary Examiner* — Duane Smith
*Assistant Examiner* — Douglas Theisen
(74) *Attorney, Agent, or Firm* — Wood, Herron & Evans, LLP

(57) ABSTRACT

A medical ultrasound system. A base unit is included having system electronics, a user interface and ultrasound control electronics. An ultrasound therapy head is in electronic communication with the base unit. The therapy head includes a replaceable, sealed transducer cartridge with a coupling fluid therein. A cooling system is provided for cooling the coupling fluid. A plurality of guide indicators are positioned around the therapy head to align with crossed lines on a patient so as to properly align the therapy head prior to use. The therapy head can provide variable treatments to an area while the therapy head is in contact with a patient.

12 Claims, 61 Drawing Sheets

U.S. PATENT DOCUMENTS

| | | |
|---|---|---|
| 6,402,810 B1 | 6/2002 | Mayer et al. |
| 6,402,818 B1 | 6/2002 | Sengupta |
| 7,294,171 B2 | 11/2007 | Yamada |
| 7,387,660 B2 | 6/2008 | Tessien et al. |
| 7,857,773 B2 | 12/2010 | Desilets |
| 2002/0129705 A1 | 9/2002 | Castellano et al. |
| 2003/0010213 A1 | 1/2003 | Gerner et al. |
| 2003/0233937 A1 | 12/2003 | Martel |
| 2006/0122509 A1 | 6/2006 | Desilets |
| 2007/0238994 A1 | 10/2007 | Stecco |
| 2008/0125764 A1* | 5/2008 | Vancelette et al. .............. 606/22 |
| 2008/0243035 A1 | 10/2008 | Crunkilton |
| 2009/0120296 A1* | 5/2009 | Saito ............................... 96/174 |
| 2009/0171252 A1 | 7/2009 | Bockenstedt |
| 2009/0248578 A1 | 10/2009 | Pollock |

* cited by examiner

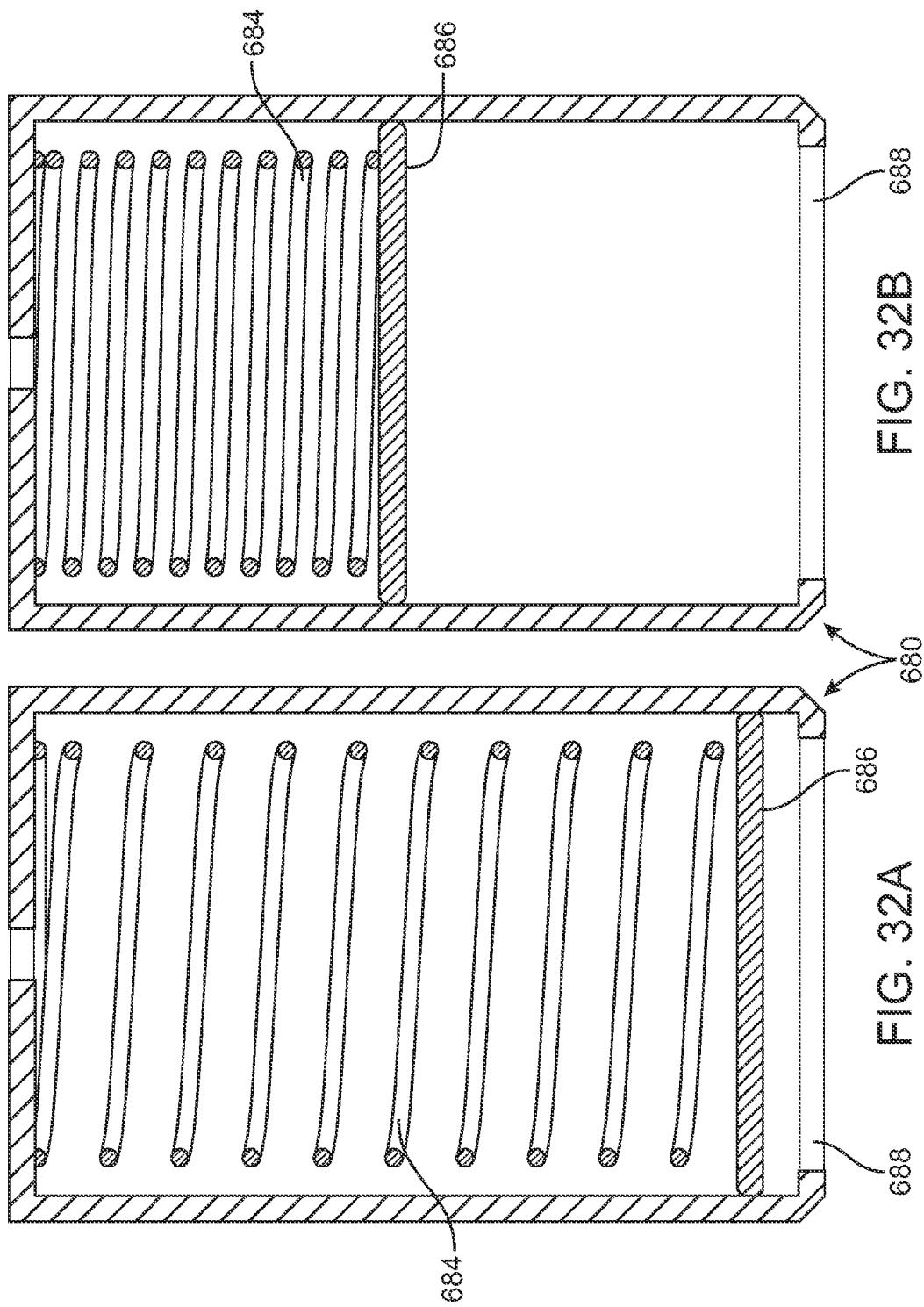

LIQUID DEGAS SYSTEM

CROSS-REFERENCES TO RELATED APPLICATIONS

The present application claims priority of U.S. patent application Ser. No. 61/246,937, filed Sep. 29, 2009, the full disclosure of which is incorporated herein by reference.

BACKGROUND

High intensity focused ultrasound (HIFU) has gained increased popularity and support as a therapy device in the medical community. Ultrasound energy has been used extensively in non-therapeutic procedures such as tissue imaging for diagnostic purposes. HIFU involves higher levels of power (over diagnostic ultrasound), to achieve a variety of physical effects in tissue for the purpose of achieving a desired therapeutic effect. A recurring design issue for HIFU treatment devices is balancing the needs of the therapeutic demands a procedure may require, and the acceptability of the device produced by medical device manufacturers. This is particularly true in aesthetic medicine, where devices of therapeutic utility must meet the rigorous utility, image and usability demands of practitioners of aesthetic medicine and their clientele.

BRIEF SUMMARY

Water and other liquids used in the methods and system for the present invention will frequently need to have dissolved gasses removed to produce a degassed liquid stream. A liquid degas system suitable for producing such a water or other liquid degassed stream comprises a reservoir and a ventilation chamber within the reservoir, where the reservoir contains a gassed liquid which is subjected to a pressure drop sufficient to separate the gassed liquid into a degassed liquid stream and a gas stream which are then delivered to the ventilation chamber. Within the ventilation chamber, the gas and degassed liquid are separated with the gas being returned to the gassed liquid within the reservoir and the degassed liquid being removed for use in the therapy systems herein, either as a cooling liquid, an acoustic coupling liquid, or both.

The liquid degas system further comprises a conduit located to receive the gassed liquid from the reservoir and pass the liquid to a bottom of the ventilation chamber. The conduit has a flow restriction, such as a reduced diameter orifice, valve, or other reduced diameter component within the conduit which creates the pressure drop as the gassed liquid presses through the flow restrictor. A pump is provided to cause the gassed liquid to flow from the reservoir, through the flow restriction, and through the conduit into the ventilation chamber. Typically, the pump will be positioned downstream from the flow orifice, usually between the flow orifice and the ventilation chamber. A gas vent is provided on the top of the ventilation chamber and receives the separated gas and releases said gas through an exit port into the gassed liquid within the reservoir, typically at a level which is below the top of the ventilation chamber. An outlet is provided at the bottom of the ventilation chamber to allow the degassed liquid to be removed from the ventilation chamber and delivered to other parts of the system.

In exemplary embodiments, the system further comprises a distribution manifold within the ventilation chamber, where the manifold receives the degassed liquid and gas mixture from the conduit and distributes that mixture throughout the ventilation chamber. Usually, the distribution manifold includes sidewalls and a top with orifices formed therethrough to distribute and release the mixture within the ventilation chamber. The gas vent typically comprises a vent conduit attached at one end to an aperture for passage within the top of the ventilation chamber and having the exit port at a level below the top of the ventilation chamber. The characteristics of the pump and the sizes of the conduit and flow restrictor will be selected to provide a pressure drop across the flow restrictor so that the liquid gas mixture has an absolute pressure in the range from 1 to 2.5 pounds per square inch (psi) after it is passed through the flow restrictor. In the exemplary embodiments, the liquid degas system may be provided in an enclosure which is attached or otherwise coupled to an ultrasound therapy head by a cable having proximal distal ends. The cable provides liquid circuit from the outlet of the degas system. Optionally, the system may include a chiller or cooler if the degassed liquid is intended to provide cooling for the therapy head.

In another aspect of the present invention, a method for degassing a liquid comprising maintaining a gassed liquid in the reservoir. The gassed liquid is drawn from the reservoir through a flow restrictor to form a mixture of degassed liquid and gas as a result of the pressure drop which occurs as the liquid flow through the flow restrictor. The mixture of degassed liquid and gas is then passed to a ventilation chamber within the reservoir where the mixture is able to separate into a gas portion which rises to the top of the chamber and a degassed liquid portion which falls to the bottom of the chamber. The gas is vented from the top of the ventilation chamber into the gassed liquid in the reservoir, and the degassed liquid portion can be removed from the bottom of the ventilation chamber for use in the therapy systems of the present invention or in other systems.

This method may further comprise circulating the degassed liquid from the bottom of the ventilation chamber through a liquid circuit where it absorbs gas and returns to the gassed liquid within the reservoir for recycling and treatment. The liquid circuit may comprise a therapy head having an ultrasonic transducer therein, in which case the liquid circuit may further comprise a heat exchanger to cool the degassed liquid before it enters the therapy head. In certain embodiments, the mixture of the degassed liquid and gas maybe passed through a distribution manifold having a plurality of orifices which create a positive pressure and restrict flow of the degassed liquid.

BRIEF DESCRIPTION OF THE DRAWINGS

FIGS. 32A-B provide a pressure relief mechanism in accordance with an embodiment for the cartridge;

DETAILED DESCRIPTION

Figure 1:
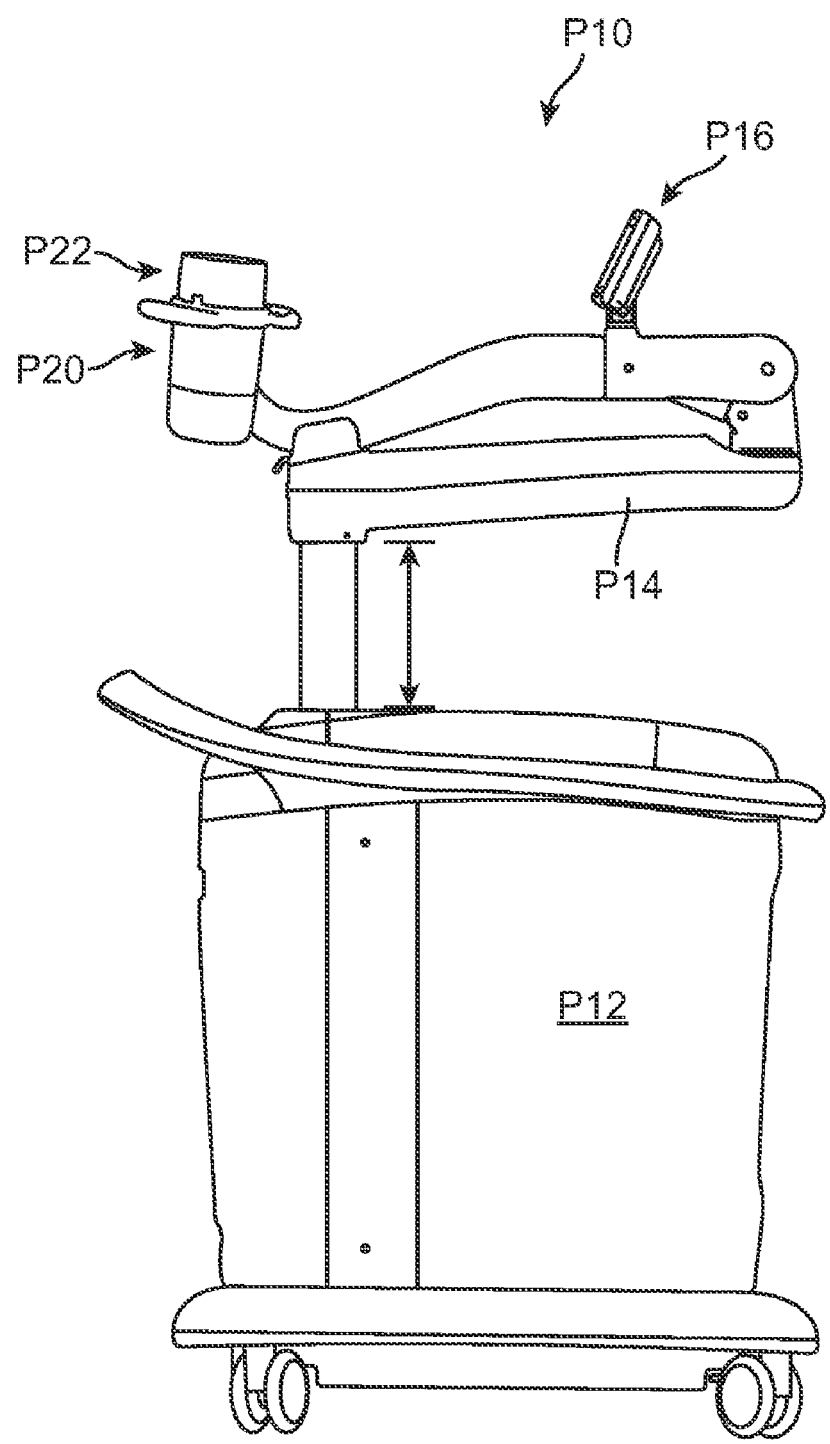
FIG. 1 shows a medical ultrasound system of the prior art.

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Described herein are medical ultrasound systems for body contouring, components of medical ultrasound systems, and methods for servicing, updating and using medical ultrasound systems.

Medical ultrasound systems on the invention typically include two main components with various subcomponents. The first main component is the base unit. The base unit component is usually a mobile piece of equipment designed to rest on the floor and provide an enclosed form factor that houses numerous subcomponents of the system. Details of the sub components are provided throughout the description. Mainly, the subcomponents that are either large or heavy, or more conveniently located away from a patient, are stored in the system base. The base unit refers to the larger of the two main components. It may have castors or wheels and be referred to herein as a cart. Mobility in the base unit is generally provided for ease of use, but in no way should be read as limiting the invention in any way.

The second main component is the treatment head. The treatment head component of medical ultrasound systems of the invention is also described herein in various embodiments. In a typical aspect, the treatment head has two sections that are detachable from each other. When the two sections are properly assembled in such aspects, the treatment head operates in conjunction with the base unit to produce ultrasound energy for medical purposes. Each section is often referred to herein as the therapy head body, and the cartridge. Alternatively the therapy head body may be the upper compartment while the cartridge is the lower compartment. The therapy head (or therapy head body) contains subcomponents that are designed for long wear and extended use. The cartridge contains subcomponents that are generally designed for limited use before being replaced. The term treatment head and therapy head are sometimes used interchangeably and may include the cartridge with the upper compartment. The cartridge contains an energy emitter, and in most embodiments, this energy emitter may be at least one high intensity focused ultrasound (HIFU) transducer. The cartridge generally is removable and has a limited life span.

The primary purpose of the system is to provide therapeutic ultrasound for the purposes of body contouring. This intended use of the system is for non-invasive therapy. That is, the present system and its many sub components are designed for use outside a patient body and typically does not involve any minimally invasive techniques, surgery, or tissue imaging other than what the system is capable of performing by itself. The system can operate independently of diagnostic, imaging, or anesthetic equipment that might also be used on a patient. Systems of the invention also or alternatively can be used in a non-sterile field. Sterilization of the many parts and system surfaces is not typically required between uses, though individual users may choose to do so for various reasons. The many embodiments of the invention described herein provide for a more usable device for body contouring over those of the prior art.

An interface cable is typically used to connect the base to the treatment head. A number of examples of such cables are described herein.

The description of the many embodiments of each of the components is not meant to imply a strict requirement of one embodiment of one component being tied solely to another embodiment of another component. Rather the description of the various embodiments of each the base unit, the treatment head and the interface cable should be viewed as interchangeable. An embodiment of the base unit may be used with more than one embodiment of the treatment head, and vice versa. Some embodiments of either the base or the treatment head will logically exclude embodiments of the other component. Those skilled in the art will realize certain pairings of base unit and treatment head do not go together, however in general the various embodiments of one component are designed to work equally well with the various embodiments of the other components. The various embodiments are herein described both in text, and in annotated drawing descriptions.

In an embodiment, the base unit is a base with a low center of gravity and rests on a frame with casters. Extending from the base is, e.g., a combined ergonomic front panel and main system compartment. The main system compartment can be mounted on the frame with casters, and the ergonomic front panel serves as one side of the compartment. The front panel typically extends upward from the base and main compartment. One or two handles are usually integrated into the front face so that the handle(s) can be easily reached, and a display screen is commonly ergonomically positioned for easy viewing. The front panel typically further possesses at least one docking port for removably receiving a treatment head. Additional docking ports may also be incorporated into the front panel.

Extending from the upper end of the front panel typically is a display screen. The display may also be a touch screen interface. The display panel or the base unit may have speakers for producing audible signals for the user. Inputs for other user interface devices, such as a keyboard, mouse or pointer device, may also be provided.

The main compartment of the base unit contains the bulk of the system electronics. These electronics typically include a group of treatment head connectors (electrical and fluidics) and a treatment head interface board; a digital data interface; system electronics including a therapy processor and a high voltage transmitter; electronic control for a fluidics system (liquid circulation system) having chiller/fans, fluid tank, pump and sensors; and a system power supply. The fluidics system may also incorporate a degas device for removing dissolved gasses from the liquid. Additional electronics may be added via one or more daughter board adapters located on any one of the existing boards within the system.

Systems of the invention should typically utilize liquid in the fluidics system in a different manner over the prior art. Instead of filling and draining the therapy head when replacing a transducer, many embodiments use a transducer in a sealed cartridge. The cartridge may contain about 100 to 200 milliliters (ml) of static liquid coupling fluid, whereas the prior art may use about 400-500 ml of liquid routed throughout the base unit and the therapy head. The cartridge may be designed for using about 120-160 ml, and in another aspect the cartridge may contain 130-150 ml. In addition, embodiments herein utilize a cartridge that is self contained. Thus, the coupling liquid remains static in the cartridge, and does not need to be replaced when that cartridge is removed from the therapy head. Distinguished from the coupling liquid is a cooling liquid in many embodiments. The cooling fluid is circulated through a heat exchanger thermally connected to the cartridge. The heat exchanger may be in the cartridge (integrated within the cartridge) or part of the therapy head and fashioned to draw heat away from the cartridge. Using a separate cooling liquid (from the coupling fluid) allows the cooling liquid circulation to move the length of the circulation system more efficiently. The majority of embodiments also provide for a treatment head that no longer requires constant filling and draining, thus reducing the spillage and fluid loss from the fluidics system. Advantages of some embodiments of the systems of the invention also or alternatively include faster and/or cleaner replacement of the transducer assembly.

The description of pressures herein make reference to either "absolute" pressure, or "gauge" pressure, both measured in PSI. Absolute pressure is the pressure measured independent of atmospheric pressure. It is the "absolute" pressure relative to zero PSI (pounds per square inch). The gauge pressure is the pressure above the local atmospheric pressure. Gauge is the local atmospheric pressure, plus the pressure read in the system or component described. The various pressure readings are usually called out, however unless specified, pressures relating to the therapy head are generally GAUGE pressures, and pressures in the fluid circulation components in the base are generally ABSOLUTE pressures.

The use of a separate cooling liquid and circulation system (separated from the coupling liquid in the cartridge) may allow the circulation system to pump smaller volumes of cooling liquid to cool the cartridge. Typically, the cooling system pumps the cooling liquid at about 40 PSI (gauge) in the base unit to achieve a therapy head/cartridge system pressure of about 20 PSI (gauge). The cooling system pressure is generally above atmospheric pressure throughout the system, but may approach atmospheric pressure when returning from the therapy head to the fluid reservoir (described herein). In these embodiments, the lower fluid quantity required in the therapy head allows for a lower volume of fluid to be pumped, and may in turn allow for a pump using less power. It may also be true that a lower fluid flow rate (volume/sec) is required to provide the same level of cooling as in prior art systems. This feature provides another area of bulk and weight savings allowing the present system to be substantially smaller in size and weight compared to the prior art. Furthermore, the fluidics system in some embodiments no longer requires a degas unit for removing dissolved gases from the coupling liquid as are used in prior art devices that circulate a coupling liquid around the transducer. This provides the advantage of allowing the system liquid to contain dissolved gasses without causing interference in the transmission of ultrasound energy in the cartridge fluid from the treatment head to the patient.

The system described herein typically makes use of higher levels of integration in the functions provided reducing power and electrical signal interconnects between the various functions allowing for reduced number of circuit cards and cabling internal to the system compared to the prior art system shown in FIG. 1.

The system may have an Ethernet adapter to receive a 10/100/1000 Ethernet line which may be used to link the system to a service computer or the internet, and provide software updates, system diagnostic capabilities, account usage updating and/or investment recovery banking of unused pay-per-use units for the treatment head (also known as "user sites" and described in co-pending U.S. patent application Ser. No. 12/407,212, filed Mar. 19, 2009, and entitled "Methods and Apparatus for Medical Device Investment Recovery").

The display screen typically included with the system provides system information and operational information to the user. In one aspect, the display has touch screen capabilities, allowing the user to use the screen as a control interface for operating the system, checking system status, running diagnostics programs, displaying error messages and system alerts, and/or providing a user with an interface to check non-active functions related to system usage, such as checking the user site bank account. The display screen may incorporate both button touch screen functions, and motion sensitivity, similar to screens used in personal data assistants and mobile phones. It may also or alternatively provide an on/off switch and/or house a speaker. In another aspect, the screen is a conventional LCD device.

One or more foot switch jacks can also or alternatively are provided for connecting a single or multifunction foot switch. The foot switch may optionally be used to control therapy activation of the system. Some users prefer hand activated therapy treatment while others prefer using a foot switch. Typically, systems of the invention can provide the option for either method to be used.

A system power supply is usually provided in the cart. In one aspect, the power supply can run on normal amperage and voltage. For example, in the United States, the system operates on a standard 115 volt/15 amp 60 Hz line using a grounded plug. In Europe the system operates on a European standard 240 volts/50 Hz line. Similarly the system uses a power supply that converts the power of the local standard into the power requirements the system needs for proper operation. A safety sensor or watchdog circuit monitors the AC power input as well as the DC output of the supply and provides a cut off in the event the power input or output is out of safety specification for the system. In an embodiment, the system operates with as many components as possible requiring the same voltage. In another embodiment, the system utilizes one voltage for all components. In still another embodiment the system utilizes two voltages for all components.

The system may have one or more treatment heads connected to the base unit. The treatment head(s) are usually connected to the base unit by a cable. In one aspect, the system has been partitioned to allow for an interface cable to be used, which combines electrical and fluid channels between the base unit and the treatment head. The treatment head may also or alternatively possess any of the following: user controls allowing for the turning on or off of the transducer, a display to provide status information, a speaker or sound emitting component or device, and/or any other controls and indicator lights as may be desired. In addition to controls on the treatment head, display, and/or foot switch, the base unit can have inputs for other user input devices like a keyboard, mouse (computer pointer device), or other control unit. A wireless control device may also be used.

In one aspect, the treatment head is connected to the base unit using only the minimum number of connections required for system operation. The proper functional partitioning of the system can allow for a reduction in wires used to connect between the system electronics in the base, and the treatment head. A technical challenge in the prior art was the requirement for multiple signals wires to be used for the interface between the treatment head and system. By proper partitioning and circuit design the interface for control, monitor and status can become a pure digital interface. A digital interface can then be implemented using serialization techniques to reduce the interface to a few digital lines. Serializing data allows for reducing the number of signaling circuits. Another technical challenge of the prior art is providing a light weight and easily manageable cooling device for the hand held component. Reducing the cooling requirements of the cartridge can also allow the reduction of the fluid lines to and from the treatment head to allow for a small diameter interface cable.

To facilitate the removal of a mechanical arm as used in the prior art, one embodiment may partition the circuitry between the treatment head and base unit to allow for an interface cable to be used. An embodiment of an interface cable is now described. The interface cable possesses a high speed serial digital interface. The digital interface is enabled by partitioning any power amplifiers, for motor control or cooling devices for example in the treatment head; digitizing analog signals in the treatment head, for example temperature sensors, provide for a digital interface to the various functions in the treatment head and provide for a serial interface to the digital interfaces. This type of system allows the leveraging of existing Low Voltage Differential Signaling (LVDS) technology to implement a high speed serial digital interface between the base and treatment head. The serial digital interface removes the bulk of analog, motor drive and parallel digital signals that were carried on multiple cables in the prior art. By using high speed serial digital interface, and properly partitioning the circuitry between the treatment head and cart, the control and information can now be passed through a small group of twisted pair wires.

Serialization of the signals between the base unit and the treatment head is processed by a pair of chips; one in the base unit and one in the upper compartment of the treatment head. The chips are responsible for regulating signal traffic produced by the system electronics (both in the base and in the treatment head) and feeding them serially through two pairs of twisted pair wires. One pair allows for uninterrupted signal from the base to the treatment head, while the other pair allows for signal from the treatment head to the cart. The twisted pair wires connect (allowing electronic communication between) the pair of chips where encoding, decoding, and serialization occurs. The chips may be general processors, field programmable gate arrays (FPGA) or application specific integrated circuits (ASIC) or any combination of these devices and/or their equivalents. These chips can also perform additional encoding for line balancing and bandwidth reduction. The chips may also provide error checking of data.

In an embodiment, signal count can be reduced by using a serialize-deserialize routine executed between the pair of chips, one located in the base unit and the other in the treatment head. In an embodiment, a pair of field programmable gate array (FPGA) chips in the system and the head do additional encoding for line balance and transmission line bandwidth reduction similar to 8B/10B encoding. The FPGAs also error check the data. The pair of chips operate as serializer-deserializer (SERDES) components. The first chip in the base unit receives electrical signals from the electronic components within the base unit. All the electrical components within the base unit that are used to control any component, process or monitor any function in the treatment head are routed through the first chip in the base unit. Data is transmitted between the base and treatment head chips using time division multiplexing. Thus where unserialized signal control would ordinarily require at least one wire for every control circuit to the appropriate electrical control element to be controlled, various embodiments of system of the invention allow signals to be sent to various components to be controlled over the same wire. In an embodiment, the serialize action takes 15 signals and encodes them to 18 signals for transmission line bandwidth reduction as well as error checking The serializer then sends them through the first pair of wires with the first signal being sent for a short period and then the second signal being sent for a short period, and so on. There are 20 time periods in all due to the overhead of a start bit and a stop bit surrounding each set of 18 bits. All of this is controlled by the FPGA chips used in the SERDES operation (and/or an application specific integrated circuit (ASIC) or equivalent function SERDES device). The number of time periods is not fixed, and may be adjusted higher or lower as desired. Because the transmission and SERDES operation occur very quickly relative to the mechanical operation of the treatment head, there is no issue of lag or signal backlogging in communication between the base unit and treatment head during therapy treatment. By way of example, an embodiment of the above described operation takes advantage of simultaneous (parallel) system inputs that are sent to the treatment head in a serial fashion—or at least at a different level than the 15 bits discussed above. Data that is low enough in bandwidth is serialized prior to sending. An example of this can be motor commands. In an embodiment, each of the two motors require 12 bits of drive command. This would mean that more than all of the 15 signaled bits would be used up for just motor drive commands—24 bits. For this reason the system assigns 4 of the lines to be a Serial Peripheral Interface (SPI) bus. The system sends all 15 bits 30,000,000 times per second, easily enabling some of them to be serial in nature and still have a very high bandwidth compared to the requirements. The 24-bit data on the SPI bus in the above example would send the two drive commands about 625,000 times a second. This is well above the 20 kH motor current command sample rate produced by the motor servo controller in the main unit. It takes at least 48 "frames" to transmit the 24 bits in a serial fashion along with a data clock for SPI operation—a frame being one group of 15 bits of parallel.

By using a first pair of wires to transmit electrical signals from the base unit to the treatment head, and a second pair of wires to receive electrical signals from the treatment head (transmitted from the treatment head to the base unit) two electrical signal paths may operate simultaneously, with each path operating through a SERDES pathway. In addition to the control of various electronic components through the SERDES pathway, the operation of an array transducer can be handled in real time using direct wire connect between the transducer beam former (in the base unit) and the individual elements of an array transducer in the treatment head as described above. This is achievable using the same interface cable because the control signals thusly serialized leave plenty of room in the cable for many thin coax cables to drive an array transducer. If a single element transducer is used, only one coax cable is required, but several can be used to share the high power drive requirements or to optimize impedance matching. Appropriately, the cable can be laid out for the number of coax, twisted pair, power/ground and fluid lines required to provide proper connection, command and control of the treatment head.

Power is supplied from the base unit to the treatment head through individual power wires based on voltage needed to drive each component. To the extent multiple components in the treatment head can be driven by power of the same voltage, those components can be placed in a circuit with a single power wire carrying the appropriate voltage. The power wire between the base unit and the treatment head may be insulated and/or shielded so as not to produce any cross talk (signal interference) with the electrical signal in the SERDES pathway. In an aspect, the power lines may not be shielded, but instead the lines may be filtered at each end so as to just receive the direct current (DC). Alternatively, the data pairs are twisted and shielded to protect them from the power supply wires.

Integrated fluidics lines are also incorporated into the interface cable. Using any of several cooling and fluid circulation system described herein, the need for large volume fluid flow is now reduced to a level where a smaller volume of fluid can achieve the results previously required. This allows the use of reduced diameter tubes contributing to shrinking the design over the prior art.

In addition, the interface cable may include one or more transducer drive carrying cables. These drive cables may be coax cables, twisted pairs or shielded wires. Shielding is generally used on transducer drive cables to provide shielding for electro-magnetic interference (EMI) reasons. In an embodiment, an annular array transducer may be used, where multiple drive cables (such as coax) may be used in the interface cable to deliver signal to an array transducer. The number of coax cables may correspond directly to the number of transducer elements, or they may be reduced to fit a modified transducer excitement program (such as grouping elements into excitement groups, controlled by a single time delay for further reducing the signal load). In another aspect of the system of the invention, an array transducer may be used having twelve (12) to twenty four (24) elements, and the interface cable would have a corresponding number of coaxial cables incorporated into it. Alternatively the coaxial cables may be substituted with shielded twisted pairs (or unshielded wires if the bandwidth is low enough).

In an embodiment the interface cable has both 24 v and 5 v power wires, and a common ground wire. The various electronic elements in the treatment head, such as motors, sensors, transducer and other components can all be driven directly (or converted to the desired voltage in the treatment head) from the two power lines, one twisted pair (the other transmits data back to the components in the cart), and however many coax cables are required to drive the transducer in real time. Alternatively the components in the treatment head may all operate on one voltage (or converted to one voltage) and thus need only one power line in the interface cable.

In addition to the components described herein as commonly incorporated into the interface cable, the cable itself may be connectorized. That is, the cable may be removably engaged to the system (and/or the treatment head) to allow modularity of the treatment head to the system. In some cases the modularity will provide a means for attaching a completely different cable between the treatment head and the base unit. In other embodiments, the interface cable may carry the appropriate electrical communication and fluid requirements of different treatment heads, so that only the treatment head need be removed from the interface cable to allow connection of a new treatment head. This embodiment can allow a user to detach a therapy head from the interface cable instead of removing the interface cable from the base unit, although the user may also elect to switch the interface cable with the therapy head. The removable engagement of the interface cable typically adapts to both the electrical and fluid systems while maintaining a common adapter among the different types of cables that can be used. In one aspect, the system electronics can identify what kind of cable is attached to the base unit, and utilize the wire and fluid channels of the wire appropriately. This may be achieved by using a readable identification chip incorporated into the interface cable or its removable engagement.

Automatic identification of the parts in the treatment head may occur by using a query between the base unit and the treatment head where the query produces a response code corresponding to a look up table stored in the base unit. The look up code provides the voltage and signal requirements for the operation of the treatment head components. If the interface cable is also replaced with the treatment head, a similar query and response system can be used to identify the parameters of the cable. In addition to the cable or treatment head having an identifier response to a query, each individual electronic component within the treatment head may respond to a query through the return twisted pair. A combination of query and response systems may be used to ensure proper calibration of power, signal and control of the treatment head. In an embodiment the treatment head has an encrypted code to ensure the system uses only authorized manufactured parts with the system. The lower compartment can have (or be associated with) an encrypted authorization code to track both the proper use of authorized manufactured parts, and to track the use of the transducer for site banking purposes (and also used for calibration data). Further to the challenge and response systems described herein, the treatment head and lower compartment may also use a challenge and response protocol to ensure the treatment head and lower compartment of the treatment head are hooked up to a duly authorized cart. The challenge and use protocol and the site banking protocol are further described in co-pending U.S. patent application Ser. No. 12/407212, mentioned above.

In operation, the user typically can hold the treatment head during a HIFU procedure, and the interface cable will allow greater mobility and freedom to the operator to use the treatment head in virtually any angle or position over the prior art. The interface cable may be draped across the body of the patient under treatment, or allowed to drape over the patient's side.

If the use of a cable guide is desired by the user, an optional boom or cable retraction system may be used. A boom would provide a light weight alternative to a mechanical arm and provide sufficient structure to suspend the interface cable so the interface cable makes its approach to the patient from above the patient, instead of being draped across the patient's body. A retraction device, like a spring tensioned reel, may optionally be included that provides cable management so the interface cable does not get tangled up with the operator or patient. A retraction system may also be used within the base unit so when the treatment head is returned to its dock, the cable is automatically reeled in. Alternatively the guide may take the form of a boom, allowing the interface cable to be projected horizontally over the patient. A boom can be either retractable into the cart, or completely removable. The boom could alternatively take the form of a light weight load balancing arm.

The treatment head typically operates as a single unit during therapy, but can be separated into two discrete subcomponents. The upper compartment or therapy head body (body) usually contains electric motors, control electronics, gears and linkages for moving a transducer assembly located in a cartridge as well as the electronics like motor drivers, DACs (digital to analog converters), ADCs (analog to digital converters) and/or other logic devices. The upper compartment is typically designed for extended use, and has components that are longer in wear, or relatively expensive to replace.

The cartridge may be referred to as the lower compartment. A cooling device is typically used to remove heat from the cartridge. A cooling device may remove heat from the cartridge in a number of different fashions. In one aspect, a fluid circulation system in the base unit circulates fluid into the treatment head to cool the cartridge. Thermal regulation of the cartridge can be important because the transducer assembly inside the cartridge may generate a significant amount of heat, which can adversely affect the reliability of the transducer in the cartridge and/or become uncomfortably hot next to a patient's skin. When the therapy head body is connected to the cartridge, the treatment head is whole. The cartridge comes in multiple embodiments, and the upper compartment comes in various embodiments to adapt to the cartridge. Alternatively, the cartridge comes in multiple configurations to adapt to various shapes and design embodiments of the therapy head body. In one aspect, the cartridge is disposable.

The various descriptions for the cartridges are generally interchangeable. Typically these include several common features such as: designed to be removably engaged to the upper section or therapy head body. The cartridge defines an ultrasound chamber that contains an ultrasound transducer. The chamber is typically a sealed enclosure that is generally liquid tight. Although the chamber is often described herein as being fluid filled or liquid filled with a coupling fluid, it is not necessary that the sealed fluid enclosure contain any particular fluid, but instead fluid is not leaked when put into the sealed fluid enclosure (ultrasound chamber). In several embodiments, one of several fluids are selected as being used as the coupling fluid, and these are aspects of the invention (being "dry" or not liquid filled, alternatively being "wet" when one or more of the selected liquids is used in the ultrasound chamber).

The use of the term "ultrasound chamber" should not be interpreted as limiting the scope of the disclosure to ultrasound energy being strictly confined to the chamber. The chamber is where the ultrasound transducer resides, with the specific intent in most embodiments that ultrasound energy will radiate out of the chamber when the device is in operation. The cartridge interior defines the ultrasound chamber, which is also a sealed enclosure that is generally fluid tight.

In an embodiment, the transducer assembly is typically contained in a sealed enclosure filled with an appropriate ultrasound coupling medium, such as degassed water. The enclosure may be water tight. The enclosure may be made of plastic or other suitable material, and may have a lining on the interior of the compartment to prevent gas from seeping into the sealed enclosure and entering the degassed water. The lining can be, for example, a sputtered metal layer, such as titanium. The enclosure has an acoustic window in all embodiments, which allows for an acoustic beam path for the transmission of ultrasound energy from the enclosed transducer to outside the cartridge. In embodiments that may use a metallization layer or sputtered metal lining, the acoustic window may also be treated with such metallization or sputtered metal lining. The metallization layer or sputtered metal material would form a thin enough layer so as to permit the transmission of ultrasound energy from the cartridge. The transducer assembly is mounted to a mechanical arm or linkage that is able to engage a counterpart in the upper compartment. The upper compartment has an actuator assembly that moves the transducer assembly in the sealed enclosure by engaging directly (or indirectly) a control arm attached to the transducer assembly. The cartridge usually has a fluid tight interface built into that portion of the cartridge that engages the control arm extending down from the upper compartment. When the upper and lower compartments are properly connected, the control arm from the upper compartment engages a receptacle in the fluid tight interface. The interface may be a spherical ball with an O-ring seal under pressure, a boot or other equivalent structure. When the control arm of the upper compartment is moved by the actuator assembly, the transducer assembly in the lower compartment moves in a predictable fashion. The system controls the movement of the transducer assembly by controlling the motion of the control arm.

Electrical connections are usually provided either through the control arm (as in a hollow arm with electrical signal paths running through there), or through a separate electrical plug/socket in the interface between the upper and lower compartments. The electrical interface between the upper and lower compartments may be within the confines of the physical volume where the two compartments are joined together, or it may be an electrical plug/socket interface outside the confines of the mechanical connection. The electrical interface can provide power and timing control to the transducer assembly to control the acoustic output, as well as power one or more of a variety of sensor elements in the lower compartment that may be used to measure fluid temperature, pressure, dissolved gases and/or movement of the transducer assembly during a procedure.

In an embodiment, the cartridge can be sealed, so that a liquid within the cartridge is degassed. A metallization layer can help prevent gas leakage into the cartridge. Since the cartridge can be sealed, any heat build up in the cartridge may pose problems for the operation of the treatment head, and/or be uncomfortable to either the user and/or patient. If heat accumulation occurs, cooling the cartridge may be necessary.

In an embodiment, a transducer cartridge as described herein includes a thermally conductive plate or a heat transfer plate incorporated into the lower compartment. The lower compartment (cartridge) may have a plate in direct contact with the fluid sealed within the cartridge. In one aspect, the heat transfer plate coincides with the surface used to at least partially engage with the upper compartment. This allows heat absorbed by the heat transfer plate to at least partially radiate the heat into the upper compartment.

In an embodiment, the upper compartment has a heat exchanger in the form of a heat absorption component adapted to work with the heat transfer plate in the lower compartment. The heat absorption component of the upper compartment and the heat transfer plate of the lower compartment do not need to be the same physical size or foot print, so long as they operate to transfer heat as necessary out of the cartridge. The heat absorption component takes heat away from the cartridge through the heat transfer plate. Once heat is transferred from the heat transfer plate to the heat absorption device, the temperature in the cartridge is reduced. This heat transfer can be done continuously to set the temperature of the fluid within the cartridge, or periodically based on need. For instance, the heat transfer function may be set to automatically operate if a temperature sensor in the cartridge detects the fluid temperature exceeds a preset threshold range of about one (1) to thirty seven (37) degrees centigrade. In an embodiment, the threshold range may be narrowed to about five (5) to eighteen (18) degrees centigrade. In another embodiment, the fluid temperature may be adjusted to assist with numbing the skin of a patient by chilling the skin. The fluid temperature may be lowered to about one (1) to seven (7) degrees centigrade.

In an embodiment, the heat absorption component is a thermoelectric device, like a layer of thermal electric chips (TEC). The layer of thermal electric chips may be a single large chip, or a group of chips laid out next to each other to form a grid of chips. TECs produce a thermal gradient between the two faces of the chip when an electric current is introduced to the TEC. The cool side of the chip faces the heat transfer plate of the cartridge, while the hot side of the chip(s) face away from the lower compartment.

Heat is drawn away from the thermal electric device layer by using a heat sink attached to the thermal electric device layer. The heat sink may be a fluid filled bath having a chilled fluid circulated through it (e.g. from the fluid circulation system described in one aspect herein). The heat sink may also be a highly conductive thermal material (like copper or aluminum) formed into an air cooled device. If air cooled, a small fan may be included in the upper compartment for continually moving air across the heat sink. The upper compartment would further have both air inlet and exhaust vents for drawing in cool air and venting warm air.

In an embodiment, the heat absorption component is itself one of the above mentioned heat sinks (liquid filled bath or air cooled heat sink). In this embodiment the heat transfer plate is still formed into the cartridge, however instead of using a thermal electric device layer to remove heat from the cartridge, a heat sink is used. A fluid heat absorption layer may used and supplied with a chilled fluid from the cart. Activation of the heat absorption component may be preprogrammed for a variety of situations, such as when the fluid temperature of the cartridge exceeds a certain value or to maintain a certain temperature in the cartridge.

In an embodiment, the heat transfer plate of the cartridge may be replaced with a heat exchanger within the sealed fluid enclosure of the cartridge. Inside the cartridge, a heat conducting pipe is positioned within the cartridge so as to maximize the surface area of the heat exchanger (and thus maximize the thermal transfer area) while avoiding that volume of space within the cartridge needed for the transducer assembly to move freely. The heat exchanging pipe may be made of copper, aluminum, stainless steel or other materials (including plastic) so long as the tubing is sufficiently thin walled (thermally conductive) to allow heat transfer from the cartridge environment into the fluid in the heat exchanging pipes. The heat exchanger should also avoid interfering in the broadcast of ultrasound energy from the transducer through the transmission window. The heat exchanger may be a coil arranged in a serial configuration (as in a continuous winding of the coil), a parallel configuration (as in two or more pipes arranged in parallel alignment and fed from a single input, and drained from a single output), or a winding configuration (a mix of serpentine and/or straight paths) and any combination of these configurations are equally usable as a coil heat exchanger. In another embodiment, the heat exchanger may be a sealed plate with either serial or parallel water paths integrated into the sealed plate so as to function similar to a coil or pipe arrangement.

In one aspect the heat exchanger is liquid filled, however it is not necessarily the same liquid used in the fluid tight sealed enclosure of the cartridge. This allows the liquid in the heat exchanger to be circulated with the liquid from the fluid circulation system without compromising the structural and isolation integrity of the degassed liquid volume sealed within the cartridge. Once again the fluid in the heat exchanger is circulated with chilled fluid from the fluid circulation system and is activated on demand based on either preprogrammed parameters or user command. Note the fluid circulation system in any of the embodiments described herein may be set to "Always on" so that liquid circulation is always occurring. Chilling of the liquid circulating in the circuit may similarly be set for "always on." Because the liquid circulation fluid is separated from the liquid sealed within the cartridge, degassing is not required of the fluid in the cart/fluid circulation system. In an embodiment, the cartridge may be filled with a non-liquid fluid, such as a gas prior to actual use, and filled with a static coupling liquid just prior to use.

Various coupling and cooling fluids are used in or with the various embodiments and aspects described herein. The coupling and cooling fluids used may be similar in composition and treatment, or they may be highly variable. In one aspect, the coupling fluid used in the cartridge may be degassed water. Water degassed to less than 12 ppm of dissolved oxygen may be used as a coupling fluid inside the cartridge. In another aspect, the level of oxygen in the degassed water is about 8 ppm and in another aspect the level of degasses oxygen may be about 5 ppm or less. In another aspect, the coupling fluid inside the cartridge may contain additives to extend the life of the cartridge (such as a biocide to increase the shelf life) or other additives that may improve the device performance or improve shelf life. In an aspect of the invention, the use of a metallization layer or sputter metal material promotes the shelf life of the cartridge relating to extending the duration in which degassed water may maintain the low level of dissolved gasses within the cartridge. The level or amount of metallization needed may be derived using the formula wherein a thickness of the metallization layer is less than X, where $X=[((\alpha-0.09)*1000)/0.03]+500$, with X being the metallization layer thickness in Angstroms, and $\alpha$ being a maximum acceptable acoustic attenuation in dB in a transmission window.

In another aspect, the coupling fluid inside the cartridge may contain various concentrations of salts. A salt solution inside the therapy head should have sufficient ultrasound transparency to allow the system to broadcast the desired amount of energy. . A salt solution helps to prevent gas absorption in the solution as well, and may reduce the possibility of producing cavitation or micro streaming events within the cartridge. The salt concentration will depend on the kind of salt used, and the desired fluid characteristic the salt concentration can provide. For the purposes of maintaining a degassed coupling solution in the cartridge, a salt solution and/or a metallization layer can be used.

In one non-limiting example, a calcium chloride (CaCl) salt was added to water for use as a coupling solution inside the cartridge. Increasing the CaCl concentration range to about ten (10) percent by weight to about twenty one (21) percent by weight to help reduce the incidence of freezing (by lowering the freezing point of the water) and reducing the likelihood of cavitation (by preventing gas bubble formation during operation of the ultrasound transducer) while maintaining a desired transparency of ultrasound energy through the salt solution. The level of CaCl may be increased or decreased as desired, and other salts probably may be used to produce a similar effect.

The cooling fluid used inside the ultrasound system may be water in an embodiment. The cooling fluid generally has a high thermal absorption capability, such as water, or a water mixture with other chemicals. Chemicals that may be used include a biocide (to prevent bacterial growth in the fluid circulation system), a chemical additive (for system detection purposes) or other ingredients that may increase the fluid system performance or longevity.

Outside the therapy head and cartridge, another coupling solution can be used to couple ultrasound energy between the medical system and the patient. In an embodiment, this coupling solution may be a water solution that is ninety-nine percent (99%) pure water, with less than one percent (1%) of impurities (excluding dissolved or suspended gases). In another embodiment, the patient side coupling solution may be a light mineral oil or other fluid having similar viscosity characteristics of water. An aspect of the system of the invention is to use a coupling solution outside the body that is drawn from the same reservoir as the cooling liquid of the fluid circulation system. In this aspect, the liquid is circulated from the base unit to the therapy head body, and then dispensed from the therapy head body onto a patient's skin.

In an aspect of the system of the invention, fluid from the fluid circulation system flows directly into the sealed fluid enclosure of the cartridge. In this embodiment, the cartridge is not sealed with a degassed fluid. Instead once the cartridge is connected to the upper compartment, the cartridge is flooded using fluid from the fluid circulation system. In this embodiment, a degas unit may be used to reduce the dissolved gas level in the fluid prior to treatment. In one aspect the fluid may be degassed down to about five (5) to ten (10) ppm or lower dissolved oxygen (oxygen being used as a common meter for all other dissolved gasses based on proportion of gas dissolution). A chiller may also be used to cool the water in this embodiment. No drip fluid connectors may be used between the cartridge and the treatment head and/or circulation system to reduce liquid leakage during cartridge replacements.

In an embodiment, the treatment head may be designed using the smaller size and components of the system described above, but retain a removable transducer cartridge that leaves the transducer assembly removably connected to the upper compartment. In this embodiment, the system replicates the process of draining the fluid from the treatment head by evacuating the fluid chamber of the treatment head.

The user then removes the transducer cartridge and replaces the transducer. The system then refills the fluid chamber inside the treatment head. The fluid in this embodiment also requires degassing. A degas device for use with these embodiments is provided herein. The degas device is connected to the fluidics system in the base unit, and utilizes a single pump to both move the fluid through the system, as well as force the fluid through a chamber for removing dissolved gasses. To reduce liquid spillage during cartridge replacement, "no drip" fluid connectors may be used, which shut off the liquid supply on the inlet and outlet liquid lines when the cartridge is replaced.

The degas unit according to this embodiment is a system for separating gas from a gas-containing liquid. The degassing system includes a flow restriction component in fluid communication with a supply of the gas-containing liquid, a pump in fluid communication with the flow restriction component, a separation chamber in fluid communication with the flow restriction component through the pump, one or more gas outlet(s) in fluid communication with the separation chamber, and a degassed fluid outlet in fluid communication with the separation chamber. The pump is configured to draw a flow of the gas-containing liquid through the flow restriction to create a solution of liquid with gas bubbles. The separation chamber is configured for gravity induced separation between the gas bubbles and the liquid. In this embodiment, gases are drawn out of solution by pulling the liquid through a small orifice. As the liquid escapes the orifice it experiences a region of negative pressure causing bubbles to form. The bubbles and liquid flow through a pump and into a separation chamber. The separation chamber is under positive pressure to slow down the escape of the gas bubble and liquid solution through the gas outlet(s). The separation chamber is placed within a ventilation chamber that is also under positive pressure. As the gas and liquid solution exit the separation chamber and enter the ventilation chamber, the gas bubbles float up, and the degassed liquid is pushed down through a liquid outlet duct.

In another embodiment, a system for separating gas from a gas-containing liquid is provided. The degassing system may include a pair of degas filters arranged serially. A liquid may be drawn through a flow restriction component to produce gas bubbles. The liquid is then pushed through a first degas filter, where gas bubbles are vented out. The liquid continues to a second gas filter that has a vent line connecting to the liquid line just prior to the intake section of the pump. The vent line provides a vacuum on the second gas filter so that dissolved gasses may be drawn out of solution and vented out of the liquid. The liquid then can be used in a fluid circuit calling for degassed, or reduced dissolved gas, liquid. The liquid circulates back into the degas system near the pump intake. The degas system may include a reservoir, in which case the liquid circuit return may flow into the reservoir.

In another embodiment, medical ultrasound systems are provided. The medical ultrasound systems include an ultrasound therapy head and a degassing system. The ultrasound therapy head includes an ultrasound transducer that is at least partially surrounded by a coupling fluid. The degassing system is typically located in the base unit and incorporated into the liquid circulation system. A liquid circuit pumps liquid from a reservoir, through a degas device and to the therapy head so as to supply degassed coupling fluid to the therapy head. In one aspect, the degassing system includes a flow restriction in fluid communication with a supply of coupling fluid, a pump in fluid communication with the flow restriction, a separation chamber in fluid communication with the flow restriction through the pump, a gas outlet in fluid communication with the separation chamber, and a degassed fluid outlet in fluid communication with the separation chamber. The pump can be configured to draw a flow of the coupling fluid through the restriction to create a solution of coupling fluid with gas bubbles. The separation chamber also or alternatively can be configured for gravity induced separation between the gas bubbles and the coupling fluid.

In an embodiment, a fluid coupling device adapted for use with an ultrasound treatment head is provided. A treatment head like any described herein or being substantially equivalent to such a component/device, may be equipped with a coupling fluid dispenser. The dispenser draws from the fluidics system of the ultrasound system for fluid. The liquid used as a coolant in the treatment head, and as a heat sink for the ultrasound transducer, may also be used to couple the treatment head to a patient body by dispersing it on to the patient. This is achieved by having a separate fluid conduit from the treatment head, to a volume of space outside the treatment head. The conduit may be under additional pressure from the fluidics system normal pressure, or it may be the same or less pressure than the fluidics system. The fluid drawn from the fluidics system is dispensed on a patient body prior to placing the treatment head on the skin surface. The fluid may be sprayed, sprinkled, dropped, or in any fashion dispersed over the patient skin surface prior to treatment. The fluid dispersion may be through an aerosolizer, mister or other dispensing mechanism. In one aspect the dispensing of the fluid is controlled by the user so the fluid may be accurately delivered and evenly distributed on the skin surface, and such delivery and distribution is on demand through an actuation device such as a button, trigger, or other mechanical/electromechanical method. The system may also control the duration of the spray to optimize the application of the fluid for proper coupling of the treatment head to the patient, and/or to avoid inadvertent draining of the tank.

Several embodiments of using the system on a patient for body sculpting are now described. In one embodiment a template for creating treatment lines on a patient body is provided. The template can be made of, e.g. a disposable, light weight material that is safe for clinical use. Any of a variety of plastic materials, bio-polymers, or other suitable material such as approved and/or safe for clinical use may be used. The template has at least one straight line drawn on it, and typically has multiple slot shaped apertures in the template that run perpendicular to the drawn straight line. In use the template is placed on a patient body, such as the abdomen or flank region, and a user takes a marking pen or similar device and creates lines on the patient body through the slot shaped apertures. The user then rotates the template 90 degrees (or an approximation thereto) so the template straight line is laid over one of the previously drawn lines on the patient skin. The user then draws additional lines through the slot shaped apertures so as to create a square grid approximately the same size as the slot shaped apertures of the template. The user repeats this process until the entire surface area desired to be treated is covered with grid lines.

The treatment head has alignment features on the sides of the treatment head. In one aspect the alignment features are on all four sides of the treatment head. In another aspect the alignment features are on adjacent sides or opposite sides. The alignment features are used to "eye ball" the position of the transducer over the drawn grid lines by placing the alignment features over the drawn lines. If only two alignment features are used, the features are either on opposing or adjacent side walls of the treatment head, and the treatment head can be aligned by using a single straight line, or the "right angle" created by two intersecting lines. This allows the placement of the treatment head on the intersection of the drawn grid lines and using the midlines as the reference marker(s) for treatment.

If a complete grid is drawn on the patient, then the spacing of the lines of the grid do not have to line up with the size of the treatment head face (as long as they are smaller than the treatable area of the treatment head if spaces between sites are not desired). In effect the alignment of the therapy head is placed on the center lines of the horizontal and vertical lines of the grid rather than centered on the area encompassed by the lines. This allows for a given treatment head with its physical treatment head area to not have to match the treatment area the user may want. In other words, a given treatment head area (size) can be used with multiple grid size templates based on the area and shape of the desired treatment region.

If we allow variable site areas and supply various templates to mark the lines, a verification feature is need to minimize the chance a user might make an error by marking one size grid on the patient and then setting up the system to treat a different size site. To minimize this chance a feature the system can read can be embedded into the template. In such an embodiment, after the user marks the patient, the user presents the template to the system to have it read the marked site area to set up the machine to match the patient markings This feature could be implemented with, e.g., an embedded barcode on the marking template or with radio frequency identification (RFID) type tags embedded into the template. In either case the user would "scan" the template into the system to allow entering the treatment screen to set up the system for the correct site area. A scan of the template refers to reading information from the template, such as a bard code, radio frequency identification (RFID), electronic code or other information containing device on the template.

In an embodiment, the system has a "scan" capability able to record the position of the grid lines on the patient body. The system ability to scan with reference to reading grid lines or the patient body may be taking a picture of the treatment area and using image recognition to find the lines on the patient body. Alternatively or in addition, the system may record the position of boundary lines created in the patient body that provide demarcation of safe treatment areas and non-treatment areas. Creation of the boundary lines is typically done prior to placing the therapy head on the patient body. Once the user has selected a particular treatment site (for instance near the edge of the treatment surface), the user may subdivide the area of the treatment surface of the treatment site under the therapy head into one or more treatment areas and one or more non-treatment areas. The system would then either create the treatment area control commands or use pre-defined tables generated off line to send to the control hardware to treat the user defined areas while avoiding the areas designated as a non-treatment area. In this embodiment, the display acts as a drawing tablet allowing the user to display either the actual grid line on the patient surface, or a representation of the gridline (in which case no system scanning of grid lines on a patient body capability is needed). The user can create dividing boundaries, either on the patient's skin or on the visual display that designated one or more sections as either safe for treatment or conversely, as non treatment regions. The image displayed can clearly indicate which of the sections, demarcated by the drawn lines, are to be used for treatment and which are not to be used for treatment. The boundary indications are not limited in shape, size or number. Indication of treatment safe or non treatment regions either on the display or on the patient may be made by using different color or pattern markers, designating the regions as treatment or non-treatment on the display. This application is helpful to treat around the umbilicus (belly button) and areas where the area of treatment may be smaller than the area of a complete grid square (such as under the cheek, arms or other spots of relatively low subcutaneous adipose tissue accumulation). The system has an enhanced software capability to convert the user defined safe and no treatment zones into operational instructions for controlling either the movement of the transducer assembly so the transducer does not move over the non-treatment areas, or a transducer control feature that allows the transducer to stop broadcasting ultrasound energy as it sweeps over the non-treatment areas. The display and subdividing of the treatment surface could also be applied to more than one site at a time, up to the entire treatment surface.

Generally, treatment of the body to produce the desired body contouring results, utilizes sufficient energy to produce a therapeutic effect. An Energy Flux value between 35-460 Joules per square centimeter at the skin surface ($J/cm^2$) is generally required. The energy flux (EF) value may be derived using the formula:

$$[(p) \times (l/v) \times (dc) \times (nl)]/(sa)$$

wherein
p=power,
l=line length,
v=velocity,
dc=duty cycle,
nl=number of lines
and
sa=scanned area.

The formulation provided provides for a calculation when the transducer is moving continuously while applying ultrasound energy. Alternatively for a treatment program where the transducer is not moving between therapy applications, the EF can be calculated using the following modified EF equation.

$$EF=[(p) \times (t) \times (dc) \times (ns)]/(sa)$$

wherein
p=power,
t=on-time per lesion,
dc=duty cycle,
ns=number of lesions,
and
sa=scanned area.

Further details are provided on in co-pending U.S. patent application Ser. No. 11/414,080 entitled Apparatus and Methods for the Destruction of Adipose Tissue, herein incorporated by reference.

In the description of the drawings below, multiple exemplary embodiments of the invention are described. For purposes of explanation, specific configurations and details are set forth in order to provide a thorough understanding of the embodiments. However, it will also be apparent to one skilled in the art that the present invention may be practices without the specific details. Furthermore, well-known features may be omitted or simplified in order not to obscure the embodiment being described. To preserve ease of reading, parts are labeled with the same number where they serve the same function from embodiment to embodiment. For instance, no less than five different versions of a cartridge (part number 600) are herein described. Each transducer cartridge is identified as part 600 even though numerous embodiments are described, with many more equivalents not described, but will be suggested or apparent to the reader skilled in the art. The use of a common numeral for the many parts detailed herein is not to be taken to indicate that the part is exactly the same physical part from embodiment to embodiment, but rather has the same function from described embodiment to embodiment. Items with the same part numbered are not necessarily structural equivalents, since various embodiments may be highly divergent physically from one another.

The nature of the systems and apparatus described herein are those of electronic devices. There are electrical signals being sent from various parts or sub systems to other parts and sub systems, as well as electrical power sent to those same parts (components) and sub systems. The transfer of electrons between any component with any other component is referred to herein as electrical communication. Electrical communication may be signals or power, used to direct, sense, control or simply turn on/off a component. The passage of electrons through any intended conduit for electrons, regardless of voltage, amperage or wattage is also electrical communication. Electrical communication includes signals sent and received by wireless systems or methods if incorporated to any part of the disclosure herein.

Furthermore, the nature of systems of the invention as described in the many embodiments involves the use of various liquids. These may be cooling liquids, coupling liquids, storage liquids or liquids used for any other purpose. Supply or transportation of any of these liquids from one of the various components to another component designed or intended to receive, use, transfer or touch any of these liquids is referred to herein as fluid communication.

A system of the prior art is shown in FIG. 1. The system P10 has a cart base P12 with a mechanical arm P14 supporting a therapy head P20 with a removable cap P22. The system also has a display screen P16. The entire system P10 weighs in excess of 300 pounds (136+ kg), and stands about 1.3 meters high, about 1.1 meters deep and about 62 cm wide. Individually the therapy head P20 weighs about 3.5-4.0 kg, and the arm P14 weighs about 32 kg. All weights excluding any fluid or liquid that is normally required for the system to operate. The size and weight of the system makes it difficult to transport, and it can be cumbersome and unwieldy.

Figure 2:
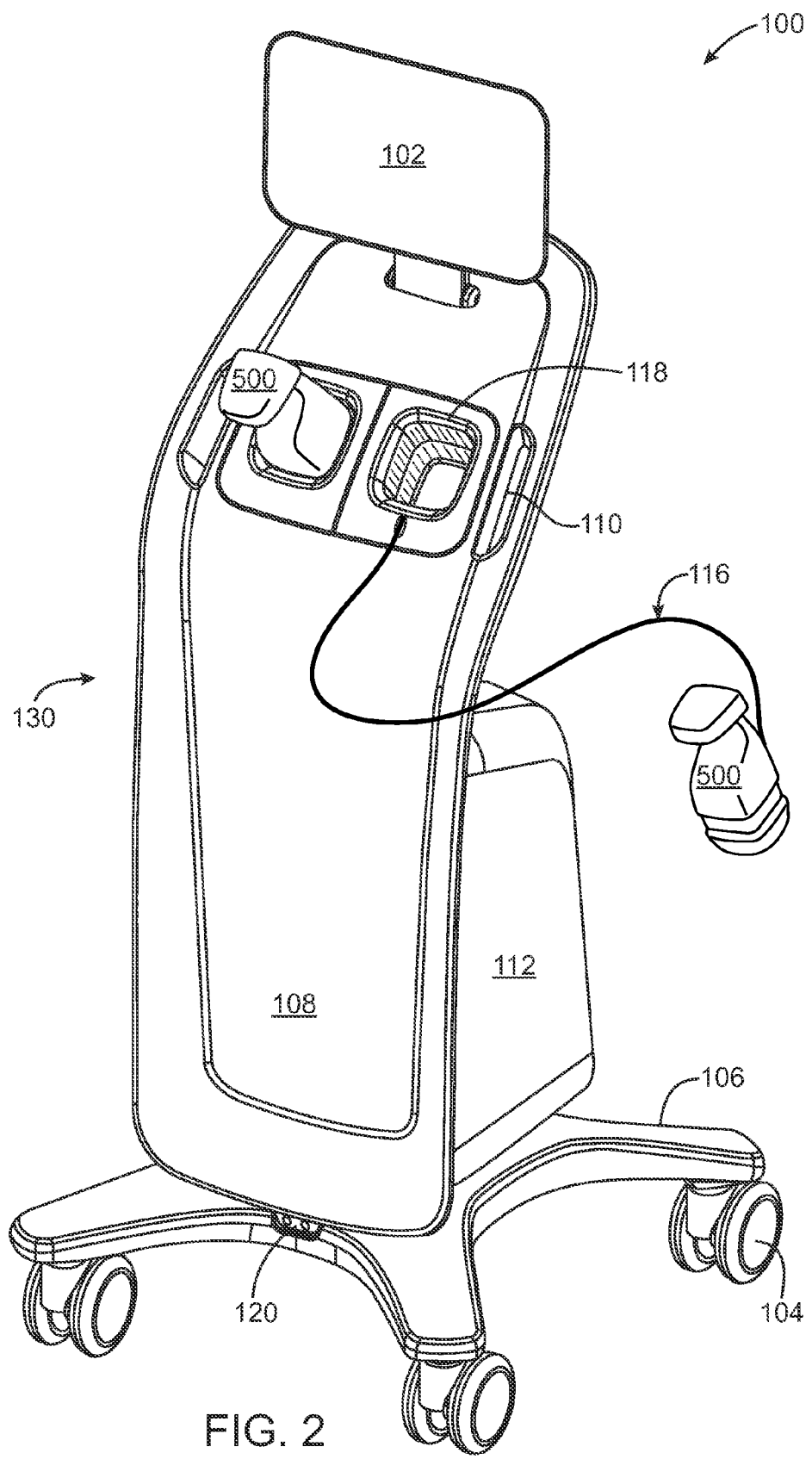
FIG. 2 is a perspective view of a medical ultrasound system in accordance with an embodiment.
Figure 3:
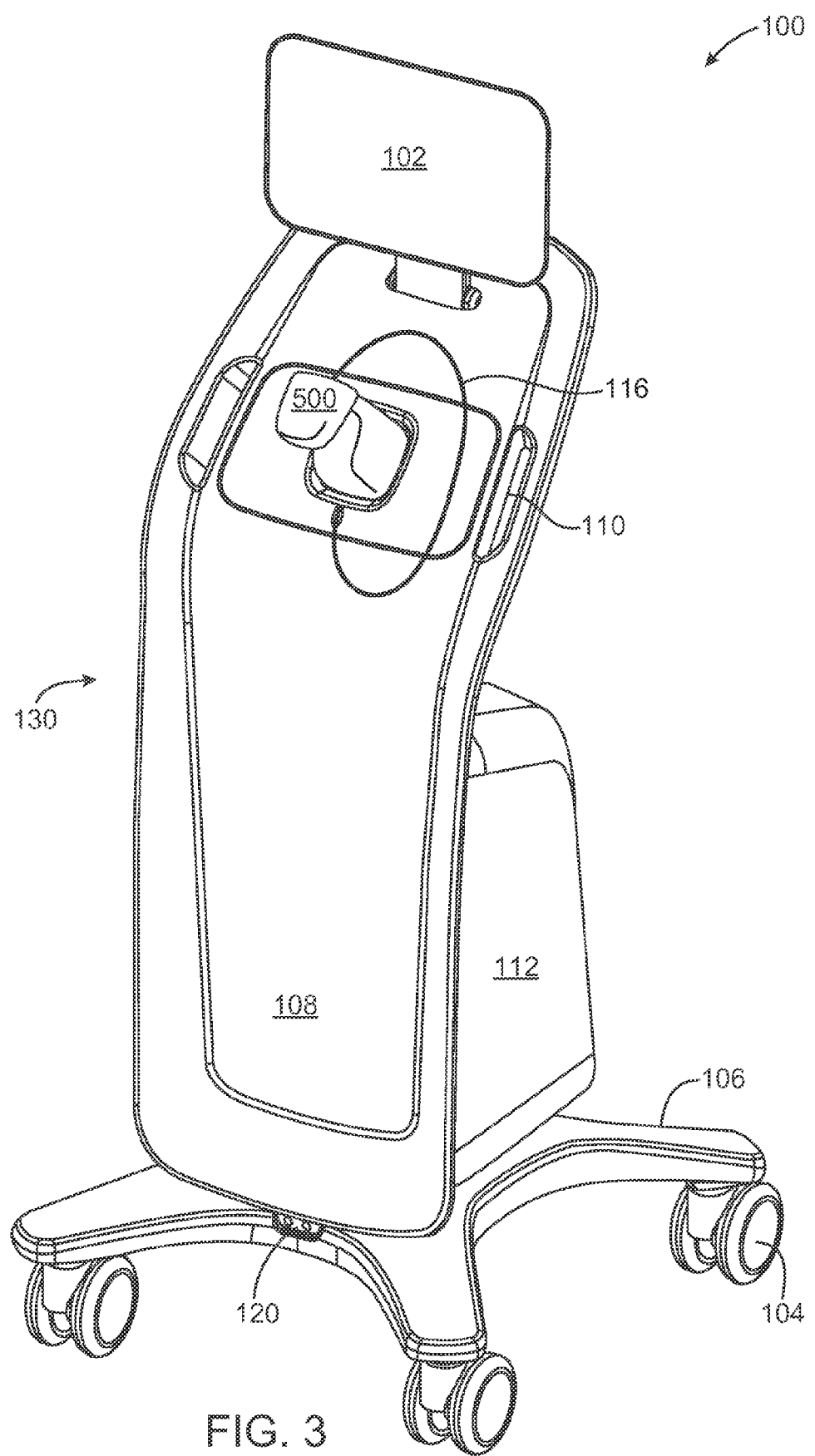
FIG. 3 is a perspective view of a medical ultrasound system in accordance with an embodiment.
Figure 4:
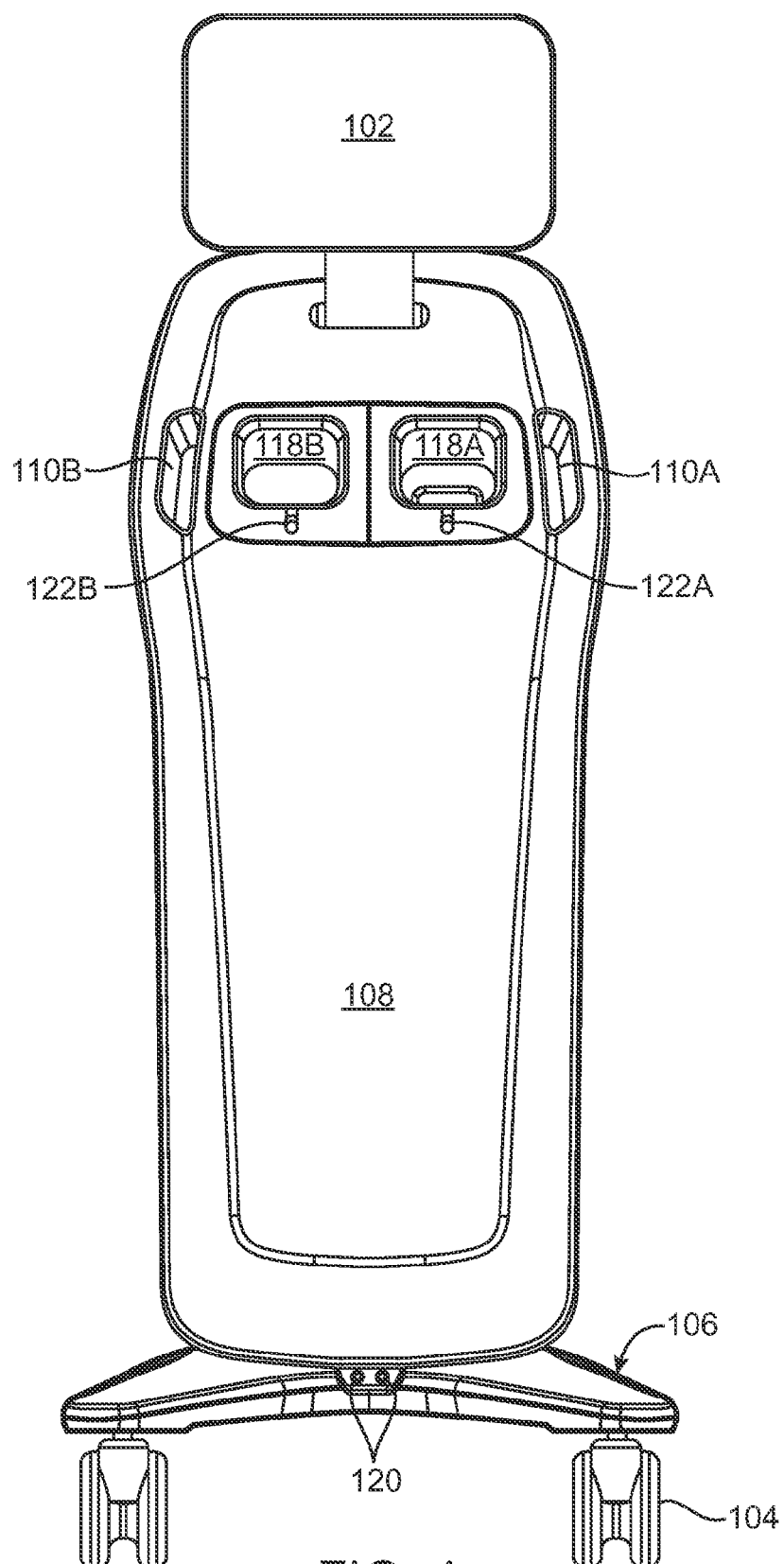
FIG. 4 is a front view of the base unit from FIG. 2.

An embodiment of the present invention is now shown in FIGS. 2-4. A medical ultrasound system 100 is shown having a display 102, a base/base unit or main body 130 with a front face 108 with one or more apertures 118 therein. The apertures 118 are receptacles for receiving a therapy head 500. The front face 108 may have one or more apertures 118 for a corresponding number of therapy heads 500. The main body 130 includes the front face 108 and a back face 132 (See FIG. 5). The main body 130 is attached to a base 106 which is fitted to receive casters 104. The base may be integrated into the main body, or separated as shown. The system 100 is shown having a main compartment 112 behind the face plate 108. The design of the system 100 can be such that the front face 108 is kept clear for aesthetic appearance. The location of the main compartment 112 containing system electronics is not crucial to the layout of the main body 130. The system 100 may include a handle or pair of handles 110 in order for a user to grasp the system and maneuver it on its castors 104. The system 100 can include one or more input jacks 120 for a foot pedal switch (not shown). A cable 116 connects the system 100 with a treatment head 500. The treatment head(s) 500 may rest in the treatment head apertures 118 where the cables 116 are plugged in, however it is not a limitation of the present invention that a treatment head must be inserted into the same receptacle as the cable which connects it to the main body 130. Indeed treatment heads 500 may be positioned in any available receptacle 118 regardless of whether they are plugged in to a cable or not.

Alternatively the treatment heads 500 of the medical ultrasound system 100 need not be stored in the receptacles 118 of the system 100 when not in use. The treatment heads 500 may be disconnected if desired and stored anywhere at the user's discretion. A single treatment head version is shown in FIG. 3. Where multiple treatment heads 500A, 500B are shown, there can be a corresponding number of receiving apertures 118A, 118B and cable plugs 122A, 122B (See FIG. 4). In an aspect of the treatment head, the treatment head may be about 80 mm on a side and have a generally rounded rectangular or circular foot print. The treatment head may be about 150-180 mm in height and weigh about 200 to 500 grams. In another aspect the treatment head may weigh between 300 and 400 grams, and in another aspect the treatment head may weigh about 330-360 grams.

Figure 5:
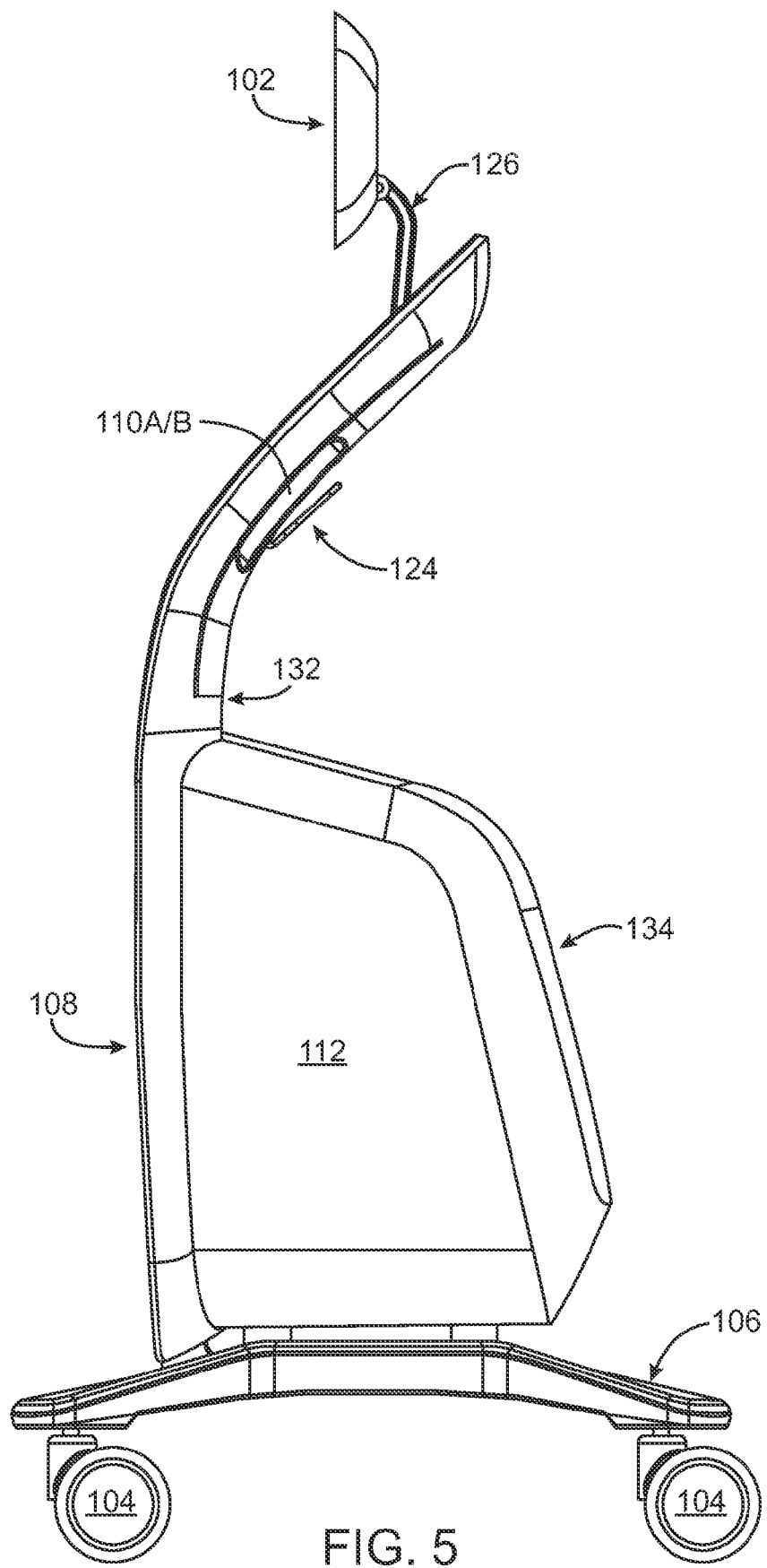
FIG. 5 is a side view of the base unit from FIG. 2.

A profile view of the main body 130 is shown in FIG. 5. The display 102 is supported by a neck 126 which can be folded down. The display 102 is also mounted to the neck via a moveable joint, the joint may allow the screen to tilt, rotate or swivel. The apertures 118 for the treatment heads have a catch or back plane 124 to prevent the treatment heads from sliding completely through the apertures. In one aspect the receptacles are formed to provide a snug fit for the treatment heads so the treatment heads are securely positioned on the main body when stored there. The system has a back plate 132, and main compartment 112 has a cover 134 that is removable. The base unit may weigh about 25-40 kilograms (kg), and in various aspects may weigh 28-35 kg (without liquid). The base unit may stand about 1.4 meters (m) in height, and be about 50-75 centimeters (cm) in width and depth. These dimensions do not count any cabling or peripherals that may be connected to the base unit.

Figure 6:
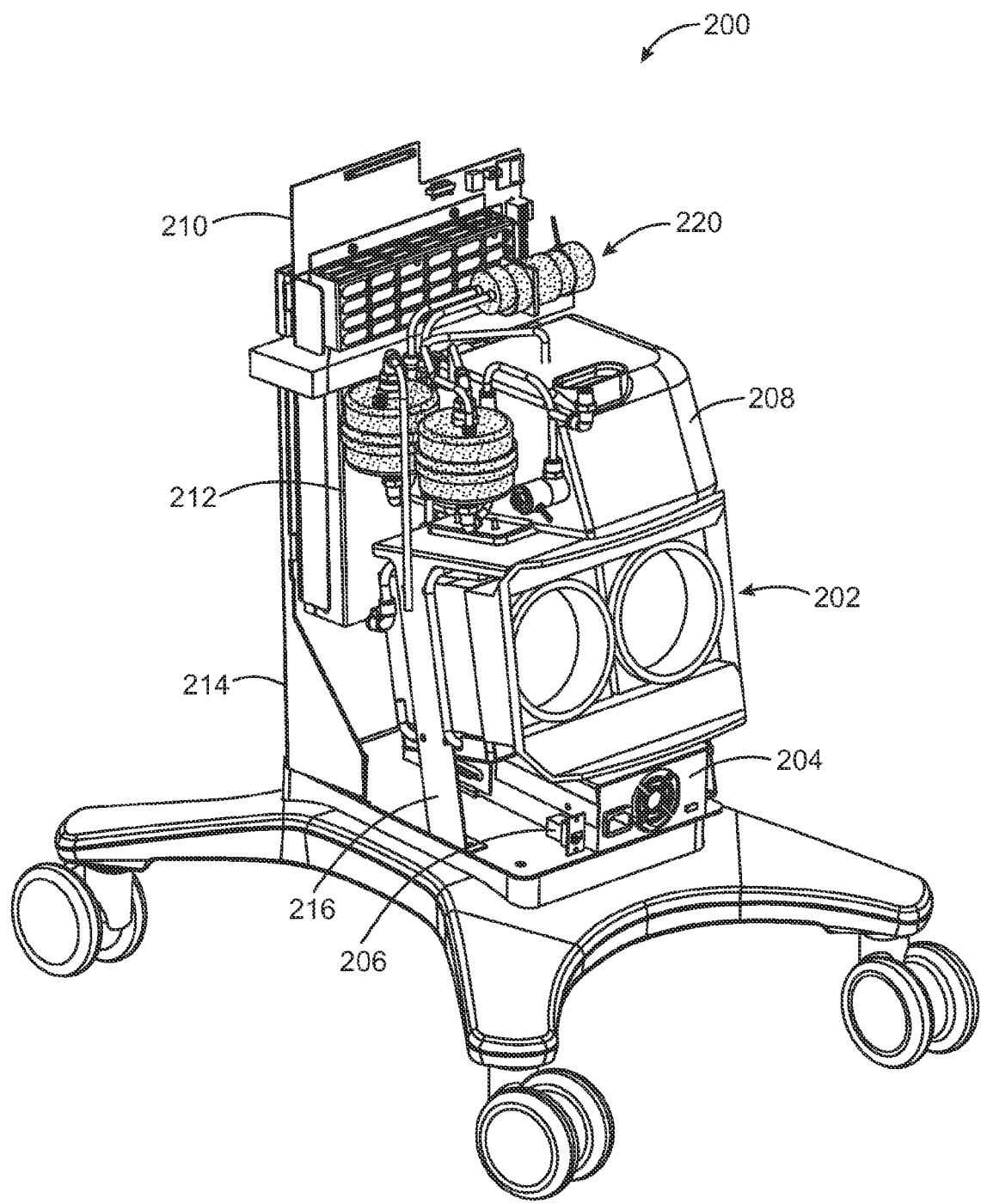
FIG. 6 is a interior perspective view of the main compartment according to an embodiment.

FIG. 6 provides a transparent view of the major system components of the main compartment 112 of an embodiment of the system. The bulk of the system electronics 200 are mounted within the main compartment 112. The internal electronics are supported by a set of structural supports 214, 216 that anchor the electronics in place while providing the orientation for air flow through the compartment. An air circulation system 202 is provided using one or more cooling fan(s). Air is drawn in by the fans and flows past a fluid chiller unit. Air flows into a cavity near the base of the unit, and then is channeled into one of two paths. One path goes through the main circuit board cage 212, along airflow path 254. The other paths flows through the power supply 204, along flow path 254 to help cool the power supply 204. The power supply may be positioned below the base 106, with the flow path 254 through the power supply adjusted to flow through an aperture (not shown) in the base 106. An Ethernet port 206 is provided to allow the system 100 to connect to an LAN or internet portal. The card cage 212 may have a back plane 210 that provides both structure to the card cage, and bus or plugs for system components. In one aspect the back plane is eliminated (excluded) by using a pair of printed circuit boards adapted to interface directly with each other. A fluid circulation system 208 is stacked on the support strut 216. The fluid circulation system has at least one pump and filter set 220 for moving the fluid through the system, and filtering the fluid to preserve fluid quality. The fluid for the system (not shown) can be a liquid having low viscosity and high thermal capacity. Liquid water can be used as a fluid for the circulation system. More particularly the fluid may be degassed liquid water, chilled liquid water. Other suitable fluids can be used. Alternatively, part or all of the air intake may be used to cool a water storage tank, or water cooling system.

Figure 7:
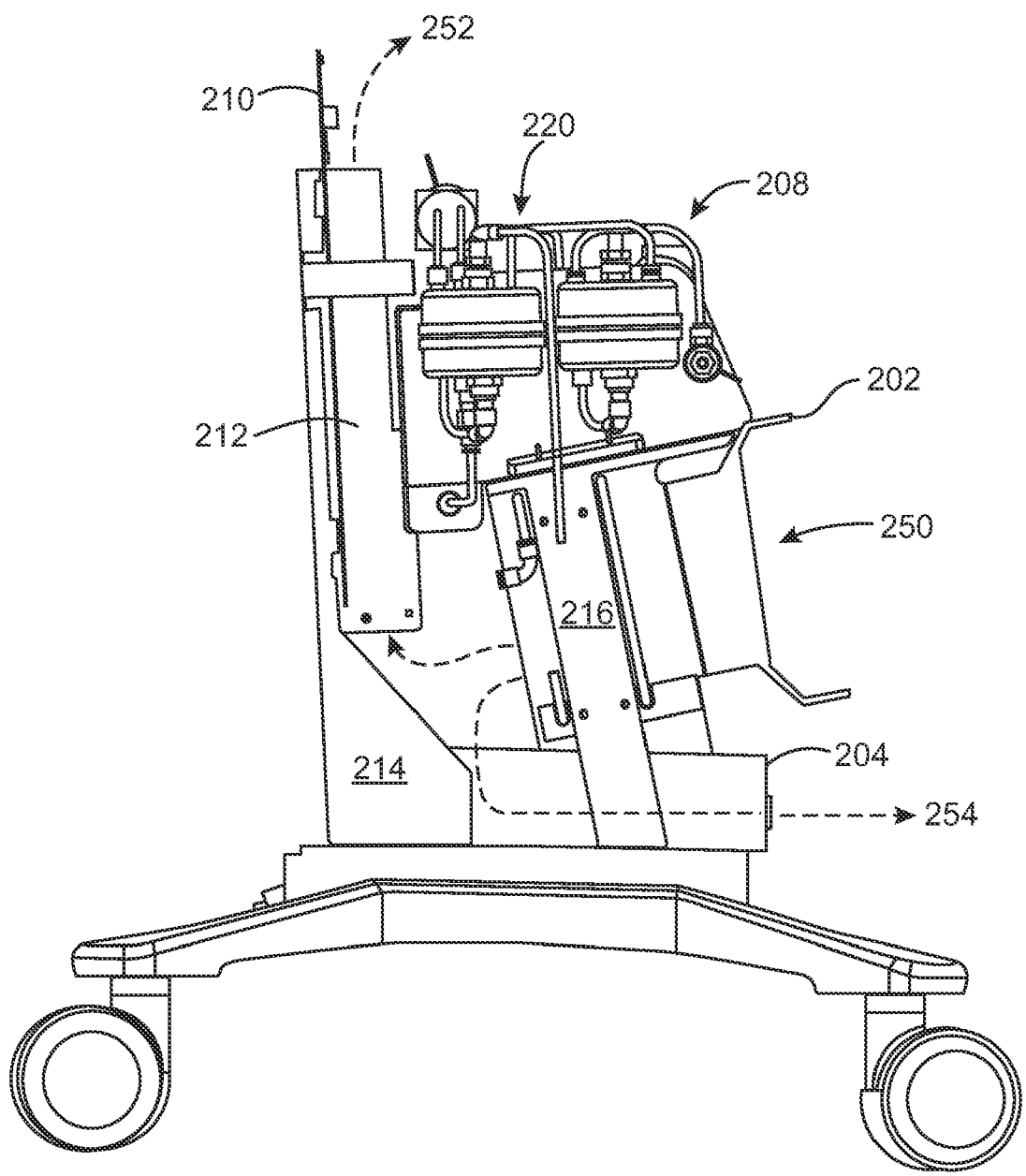
FIG. 7 is a interior profile view of the main compartment according to an embodiment.

A profile view of the main compartment system electronics of an embodiment of the system is shown in FIG. 7. The airflow path of the two air flow ducts are shown by the dotted arrows. The first air flow path 252 cools the card cage. The first duct draws air through the system cover, and drives the air into a hollow space below the card cage 212. The hollow space is defined by the support strut 214 and the components stacked on the strut 216. The card cage 212 is designed to orient cards in a generally vertical alignment with air flow space between the cards. Air is pushed into the hollow space, and drawn up into the card cage by thermal convection. Hot air from the card cage rises and flows out through a vent in the compartment cover. The second air flow path 254 helps cool the power supply 204. Air is drawn into the system through an input pathway 250 in the air circulation system 202. Once the air circulation system is active, the interior space of the main compartment becomes slightly pressurized. The power supply 204 has a fan for drawing in air from the system, while the card cage relies on forced convection to draw cool air from the bottom, while warm air rises out the top flow path 252. Alternatively the card cage may have a fan for drawing cool air into the card cage, or for venting warm air out through the exhaust vent. If the base has a water chiller, then the air flow can pass over a heat exchanger for the water chiller in addition to the other components described above. The air can flow over the various components in any suitable order.

Figure 8:
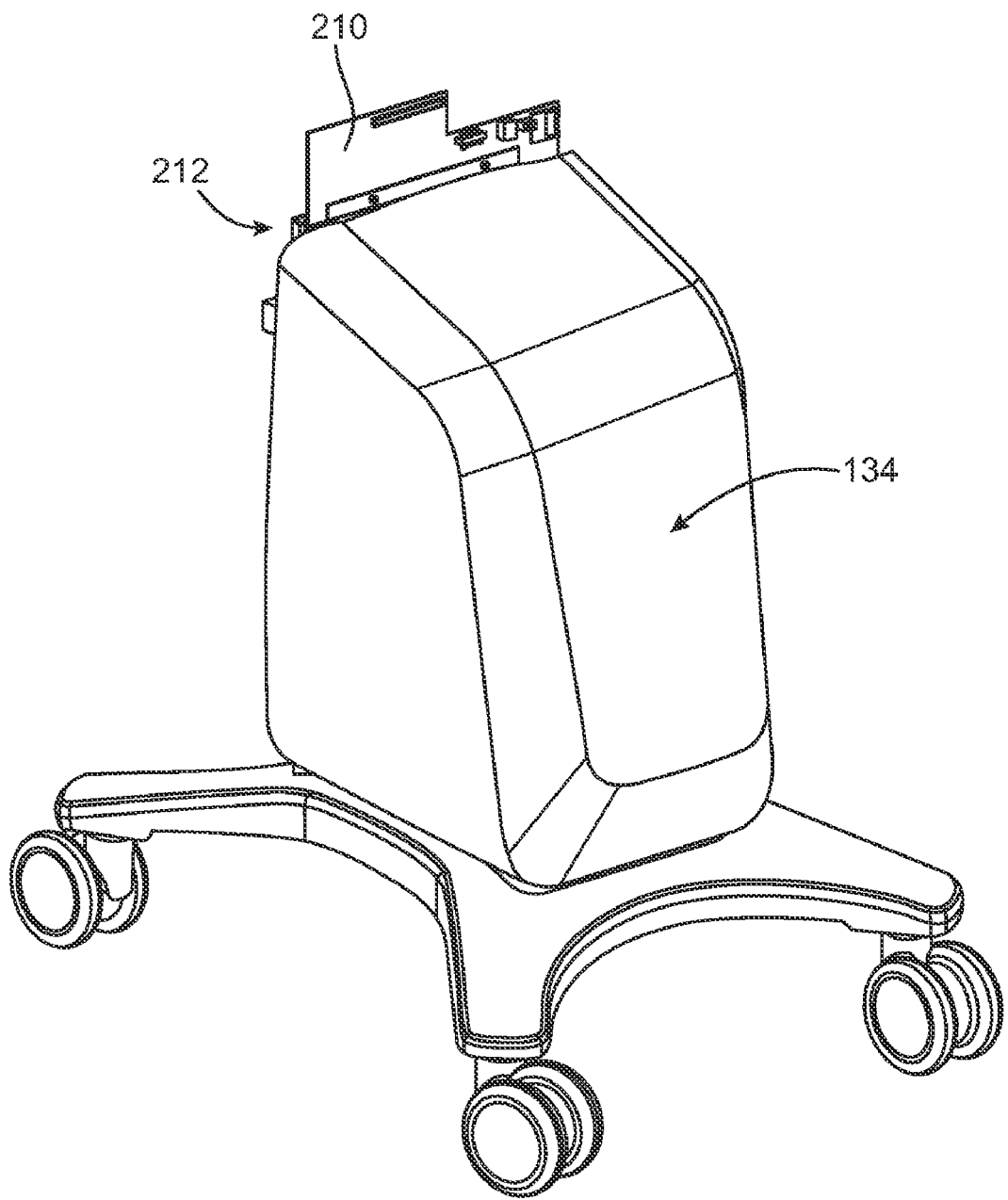
FIG. 8 is a perspective view of the main compartment with cover according to an embodiment.

A perspective view of the main compartment 112 with cover of an embodiment of the system is provided in FIG. 8. The back plane of the card cage 212 is shown extending from the top of the compartment. The front face 108 and back face 132 are not shown in this view.

One component of the fluid circulation system 208 may include a degas device used to extract dissolved gasses from the fluid in the fluid circulation system. The inclusion and use of a degas device may generally be avoided.

Figure 9:
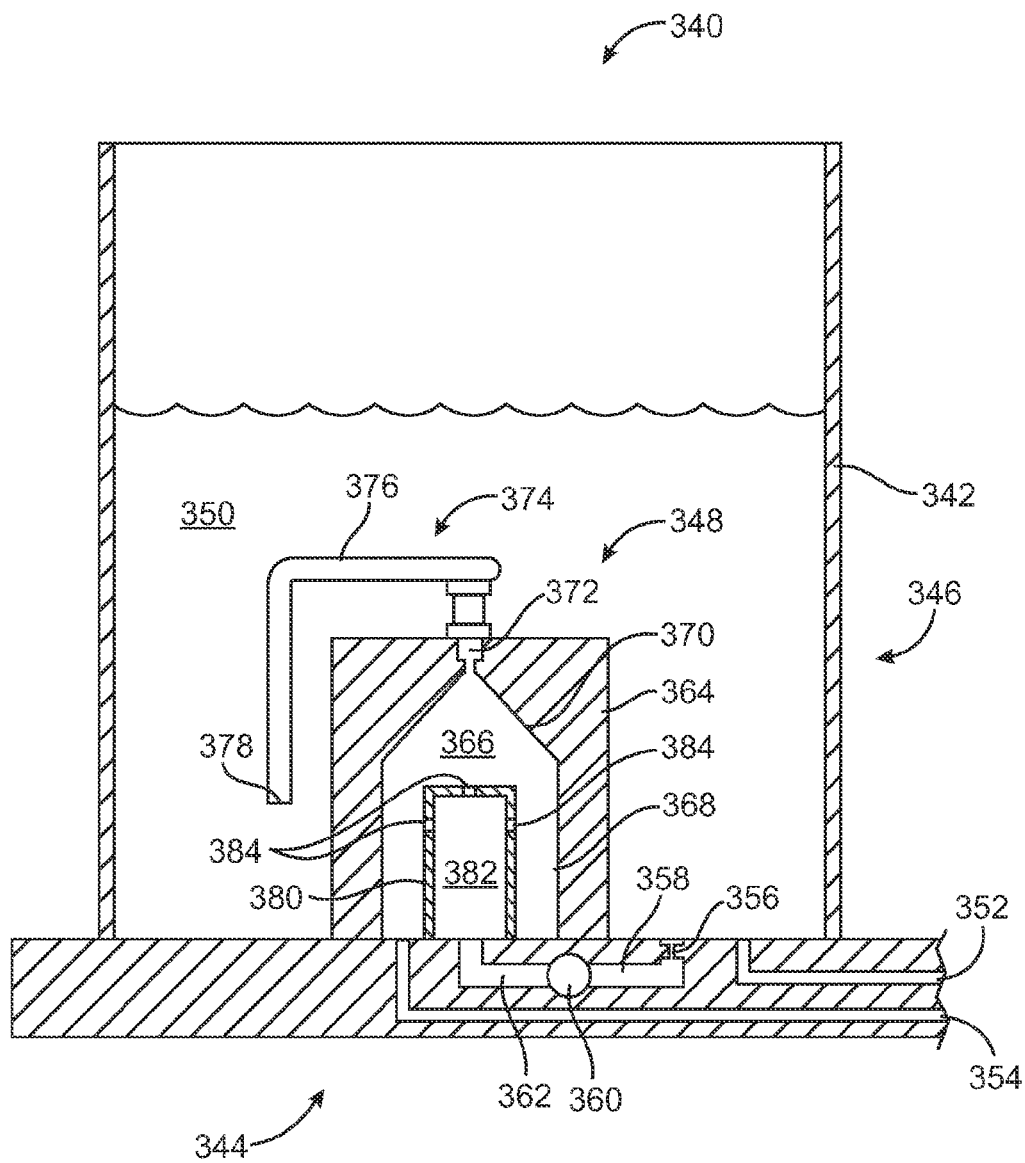
FIG. 9 shows a cross-section of a system for separating gas from a gas-containing liquid in accordance with an embodiment.

FIG. 9 shows a degassing system 340 in accordance with an embodiment. The degassing system 340 includes a retaining wall 342 connected with a base 344 that is below retaining wall 342. The combination of the side wall 342 and the base assembly 344 form a liquid reservoir 346 that is liquid tight. A separation device 348 is disposed within the reservoir 346 and connected with the base 344. The reservoir 346 holds a gas-containing liquid 350, such as those liquids described herein, that are to be degassed. The base 344 includes a supply duct or conduit 352 that can be used to add or remove the gas-containing liquid 350 to or from the reservoir 346. The base 344 may also include a separate drain line. The base includes a degas fluid carrying duct or conduit 354 for drawing degassed fluid from the ventilation chamber 366. The base 344 includes a liquid flow restriction component or device 356, a first fluid channel 358, a pump 360, and a second fluid channel 362. The flow restriction component 356 is located at the bottom of the fluid reservoir 346 and is in fluid communication with the reservoir 346. The first fluid channel 358 is positioned between the flow restriction device 356 and the pump 360 and places the flow restriction device 356 in fluid communication with the pump 360. The flow restriction device may be a nozzle, valve or other device that restricts the flow rate sufficiently for liquid flow to be sucked through the flow restriction device by a negative pressure created by the pump 360. By drawing water through the flow restriction device 356, dissolved gasses are brought out of solution by creating a negative pressure (about 1-2.5 PSI absolute) inside the first fluid channel 358. The fluid with air bubbles then passes through the pump 360, the second fluid channel 362, and into the separation chamber 382. Gas bubbles pass from the fluid chamber 382 into the chamber 366 and float upward, while degassed fluid is available to be drawn out through conduit 354. In one aspect the separation chamber is under positive pressure (approximately +10-20 PSI gauge pressure) forcing gas bubbles through the exit port 372. A pressure transducer (not shown) can be located to monitor the pressure within the first fluid channel 358. The second fluid channel 362 is positioned between the pump 360 and the separation device 348 and places the pump 360 in fluid communication with the separation device 348.

The separation device 348 includes an outer housing 364 that defines a separation or degas chamber 366. Outer housing 364 includes at least one side wall 368 connected with the base assembly 344 and at least one sloped upper wall 370 connected with the side wall 368. The sloped upper wall 370 is connected with an exit port 372 that is in fluid communication with the separation chamber 366. The exit port 372 is connected with, and is in fluid communication with, a gas bubble exhaust 374. The gas bubble exhaust 374 has an upper portion 376 that is disposed above an exit port 378. Exit port 378 places the exit port 372 in fluid communication with the fluid reservoir 346.

Disposed within separation chamber 366 is a distribution manifold 380 that is connected with the base assembly 344. The distribution manifold 380 defines an inner chamber within the degas chamber 366. The combination of the distribution manifold 380 and the base assembly 344 defines the inner chamber 382 that is disposed above, and is in fluid communication with, the second fluid channel 362. The distribution manifold 380 includes one or more orifices 384 that place the inner chamber 382 in fluid communication with the separation chamber 366. Orifices 384 are located in the upper portion of the distribution manifold 380.

Figure 10A:
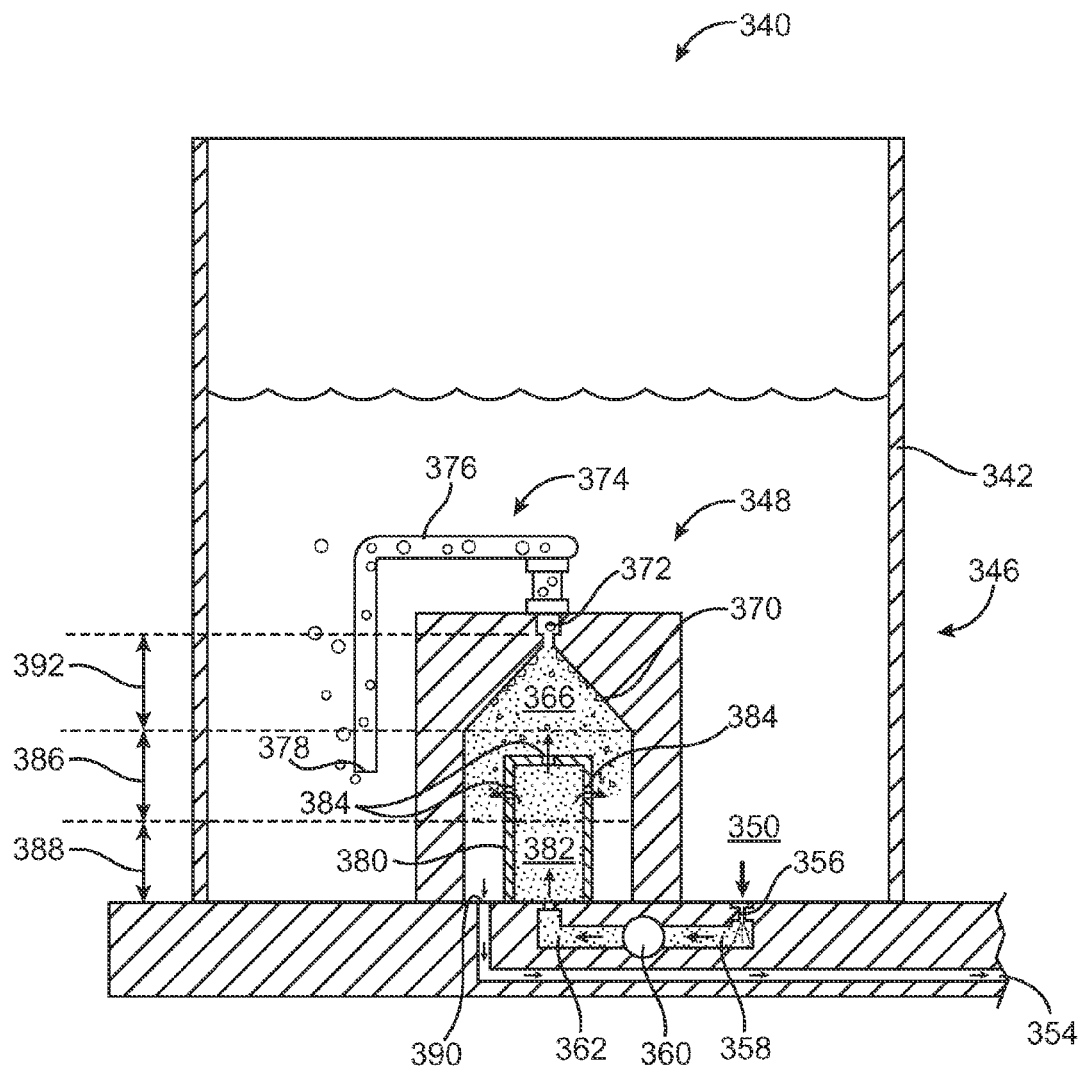
FIG. 10A illustrates the operation of the degassing system of FIG. 9.

FIG. 10 illustrates the operation of the degassing system 340 of FIG. 9. Gas-containing liquid 350 is drawn from the fluid reservoir 346 through flow restriction device 356 into the first fluid channel 358 by the operation of pump 360 such that gas dissolved within the liquid comes out of solution and forms gas bubbles. The flow of fluid through the pump generates a strong negative pressure which reduces the pressure level within the first fluid channel 358 relative to the fluid reservoir 346. The flow restriction component can be about a 0.039 inch diameter orifice (such as a drilled hole, nozzle or similar component). The pressure drop helps to bring dissolved gas out of solution thereby forming bubbles in the fluid (361 in FIG. 34). In some embodiments, the flow restriction is chosen and the flow rate is selected and/or controlled to reduce the pressure in the first fluid channel 358 to between about 1.0 to about 2.5 PSI absolute. When the gas-containing liquid is water, further reduction in the pressure (e.g., below 0.9 to 0.95 PSI absolute) in the first fluid channel 358 may cause cavitations, which can damage system components such as the pump 360. A pressure level of above about 1.0 PSI absolute has been found to be a good comprise between achieving maximum degassing while maintaining a pressure margin so as to generally avoid cavitation. A balance of negative pressure in the first fluid channel 358 and pump integrity can reduce or prevent damage to the system and/or pump. The pump flow rate is not fixed, but depends on the relation of the size of the flow restriction device 356 and the desired level of negative pressure. A weaker pump may be used with a smaller flow restriction, while a stronger pump is typically desirable with a larger flow restriction diameter device. Balancing pump capability and restriction size can also be matched with the physical integrity of the pump to withstand cavitation damage. The flow restriction typically generates turbulent flow, which may further encourage the formation of gas bubbles. A pressure transducer can be integrated into the first fluid channel 358 and the output from the transducer used to regulate the speed of the pump 360 so as to maintain the desired pressure level within the first fluid channel 358.

The liquid and gas bubbles are then transferred to the separation device 348. The pump 360 transfers the liquid and gas bubbles from the first fluid channel 358 to the inner chamber 382 of the distribution manifold 380. From the inner chamber 382, the liquid and gas bubbles are transferred to the middle portion 386 of the separation chamber 366 through the orifices 384.

The separation chamber 366 is configured for gravity induced separation between the gas bubbles and the liquid. The distribution manifold 380 introduces the liquid and gas bubbles in such as way as to minimize the amount of circulation and/or mixing of the previously separated bubbles and liquid within the separation chamber 366. The orifices 384 are small, thereby inducing slow flow, which reduces the amount of circulation and associated mixing that occurs within the separation chamber 366. The orifices 384 are located in a middle portion 386 of the separation chamber 366, which keeps the bubbles from entering a lower portion 388 of the separation chamber 366. By reducing the amount of circulation and/or mixing, the bubbles, due to their reduced density as compared to the surrounding liquid, can rise towards the top of the separation chamber without being carried lower by downward flow. The distribution manifold 380 introduces the liquid and gas bubbles in the middle portion 386 of the separation chamber 366, thereby isolating the degassed liquid disposed in the lower portion 388 of the separation chamber 366 by not causing circulation within the lower portion 388. This isolation helps to keep any gas bubbles from being carried into the lower portion 388 so that the degassed liquid extracted from the separation chamber by a degassed fluid outlet 390 can be substantially free from any gas bubbles. The degassed fluid outlet 390 is in fluid communication with the degassed fluid conduit 354, which is used to transfer the degassed fluid from the system.

The rising gas bubbles are removed from the separation chamber 366 through the exit port 372 located at the top of the upper portion 392 of the separation chamber 366. The separation chamber 366 can be configured to direct the gas bubbles to the exit port 372, such as by using conically shaped upper sloped walls 370 in the upper portion 392 as shown. The gas bubbles are forced to the gas bubble exhaust 374, which serves to prevent the surrounding gas-containing liquid 350 from entering the separation chamber 366 through the exit port 372 while the system is operating. The gas bubble exhaust 374 includes an upper portion 376 and an isolator exit port 378. The gas separated from the gas-containing liquid is transferred to the gas bubble exhaust 374 from which it exits at the exhaust exit port 378. The gas bubble exhaust 374 can be any number of isolating devices. The bubble exhaust 378 may be directed downward into the bottom of the reservoir to assist in draining the reservoir when the pump is operated in reverse.

The configuration of the degassing system 340 provides for simplified flow rate control. During operation, the pump 360 can be run at a constant speed or the speed of the pump 360 can be controlled by a closed control loop so as to maintain a desired pressure within the first fluid channel 358. With a flow restriction component 356 of a set size, the resulting pump operating speed will typically not vary to any large extent, which produces a substantially constant flow of liquid and gas bubbles to the separation device. The substantially constant flow of liquid and gas bubbles to the separation device provides a supply of degassed liquid to replace degassed liquid extracted from the separation chamber. As long as the degassed liquid is extracted at an equal or lower rate than it is generated, any excess degassed liquid flows out of the separation chamber via the exit port 372 and the isolator 374 along with the removed gas. For example, degassed liquid can be extracted from the separation chamber at a rate of 300 ml/min while a 500 ml/min flow of liquid and gas bubbles can be supplied to the separation device 348. The extracted degassed liquid (e.g., water) can be circulated for use as a coupling agent in an ultrasound therapy head, such as for use in the lower compartment 320 of the therapy head 318 as shown in FIG. 2.

An inflatable bladder or other pressure regulating device (not shown) can be used to maintain and/or regulate the pressure of the fluid reservoir 346.

Figure 10B:
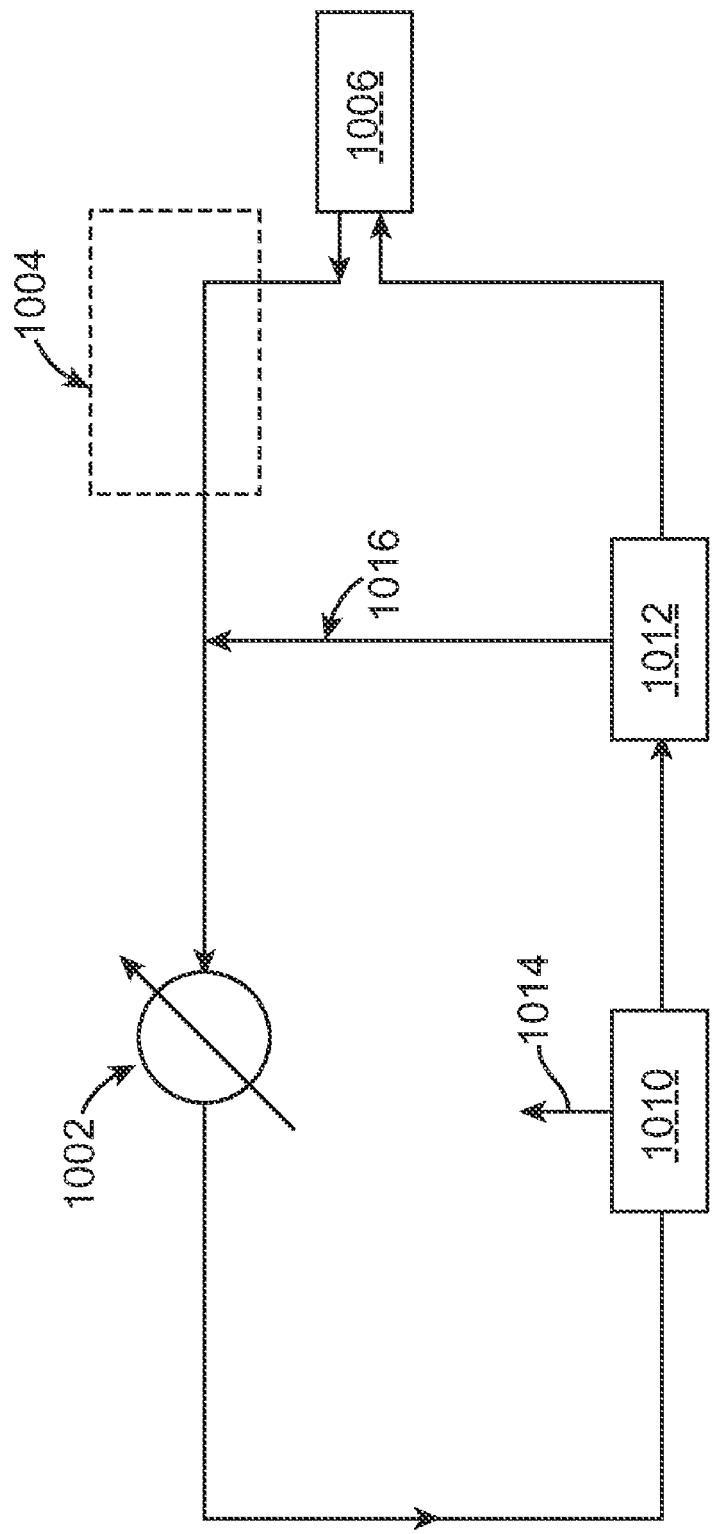
FIG. 10B illustrates an alternative embodiment of a degas system.

In an embodiment, the degas system may use two degas filters in series (FIG. 10B). The degas system utilizes a single pump 1002 to move the fluid through the entire fluidics system, and produce the pressure environments necessary to degas the liquid within the system. The liquid may be contained in a reservoir 1004 and can be drawn through a pump 1002. The liquid then is pushed into a first degas filter 1010 where bubbles are vented to the atmosphere (alternatively the bubbles may be vented into the reservoir, not shown). The liquid then flows into a second degas filter that has a vent line going into the input line that is drawn into the pump. The pump creates a negative pressure (vacuum) in the degas filter 1012 and helps to removed dissolved gases from the liquid. The liquid then goes through a fluid circuit 1006, such as to a therapy head for an ultrasound transducer, or the like. The liquid returns from the fluid circuit 1006 and either goes to a reservoir 1004, or back toward the pump 1002. As the fluid circuit operates, air bubble from the return line, reservoir or vent line 1014 move through the pump and go to the first degas filter 1010, where the bubble percolate and vent out of the degas liquid line. Degassing of the liquid occurs in the second filter 1012 which is under vacuum through the second vent line 1016.

Figure 11:
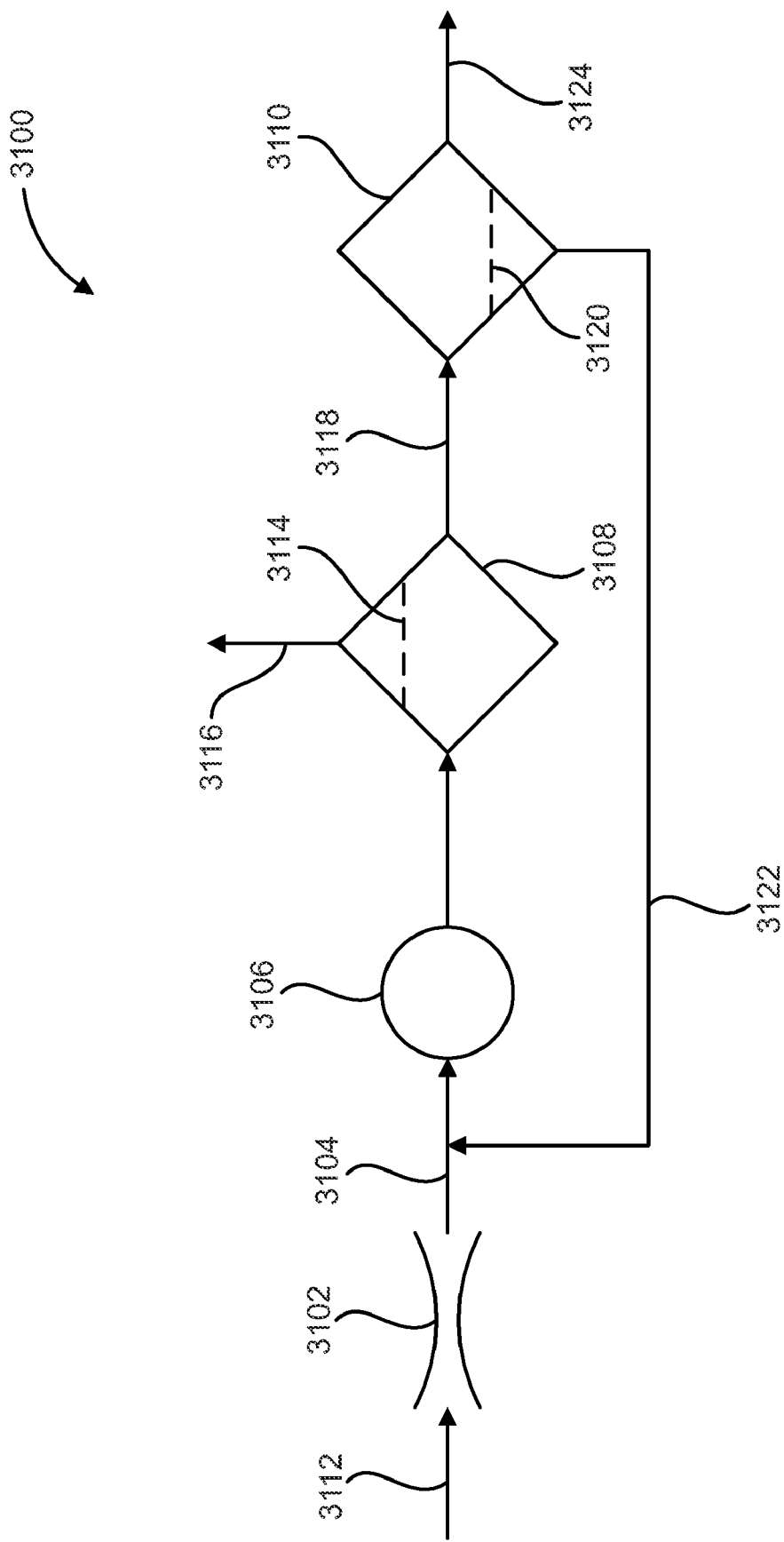
FIG. 11 is a schematic diagram illustrating a system for separating gas from a gas-containing liquid in accordance with another embodiment.

FIG. 11 is a schematic diagram illustrating a degassing system 3100 in accordance with another embodiment. Similar to the degassing system 340 discussed above, the degassing system 3100 includes a flow restriction 3102. The degassing system 3100 further includes a first fluid channel 3104, a pump 3106, a first degas filter 3108, and an optional second degas filter 3110. The flow restriction 3102 is in fluid communication with a source of gas-containing liquid 3112. The first fluid channel 3104 places the flow restriction in fluid communication with the pump 3106. An output of the pump 3106 is in fluid communication with the first degas filter 3108. The first degas filter 3108 includes a gas permeable membrane 3114 that allows the passage of gas while substantially preventing the passage of liquid. A vacuum is required on the gas side of the gas permeable membrane 3114 thereby creating a pressure differential across the gas permeable membrane 3114. The gas side may vent to the atmosphere via a vent 3116 that may include a pressure valve. The optional second degas filter 3110 includes a gas permeable membrane 3120 that allows the passage of gas while substantially preventing the passage of liquid. The gas side of the gas permeable membrane 3120 is vented to the first fluid channel 3104 via conduit 3122.

In operation, a gas-containing liquid is drawn through the flow restriction 3102 into the first fluid channel 3104 by the action of pump 3106, which causes the gas dissolved within the liquid to come out of solution as discussed above with reference to degassing system 340. The generation of the gas bubbles in the degassing system 3100 can be substantially the same as in the degassing system 340 discussed above.

The liquid and gas bubbles are then transferred to the first degas filter 3108. The pressure of the combination of the liquid and gas bubbles within the first degas filter 3108 is greater than atmospheric pressure due to the action of pump 3106. Because the gas side of the gas permeable membrane 3114 is under a negative pressure relative to the combination of the liquid and gas side, causing gas to pass through the filter to the gas side. Gas removed from the fluid in this way may be vented out of the system through a one way valve. The pressure differential serves to force gas from the liquid and gas bubbles side of the permeable membrane to the gas side of the permeable membrane, where it can be vented to the atmosphere or collected. Degassed liquid 3118 exits the first degas filter 3108.

The degassed liquid 3118 exiting the first degas filter 3108 can be further processed via the optional second degas filter 3110 so as to further reduce the amount of gas contained within the liquid. The reduced pressure level within the first fluid channel 3104, together with the pressure of the degassed liquid 3118 within the second degas filter 3110, creates a pressure differential across the gas permeable membrane 3120. The pressure differential serves to force gas from the liquid and gas bubbles side of the permeable membrane 3120 to the gas side of the permeable membrane 3120, where it is transferred to the first fluid channel 3104 via conduit 3122. The additionally degassed liquid 3124 exits the second degas filter 3110.

Figure 12:
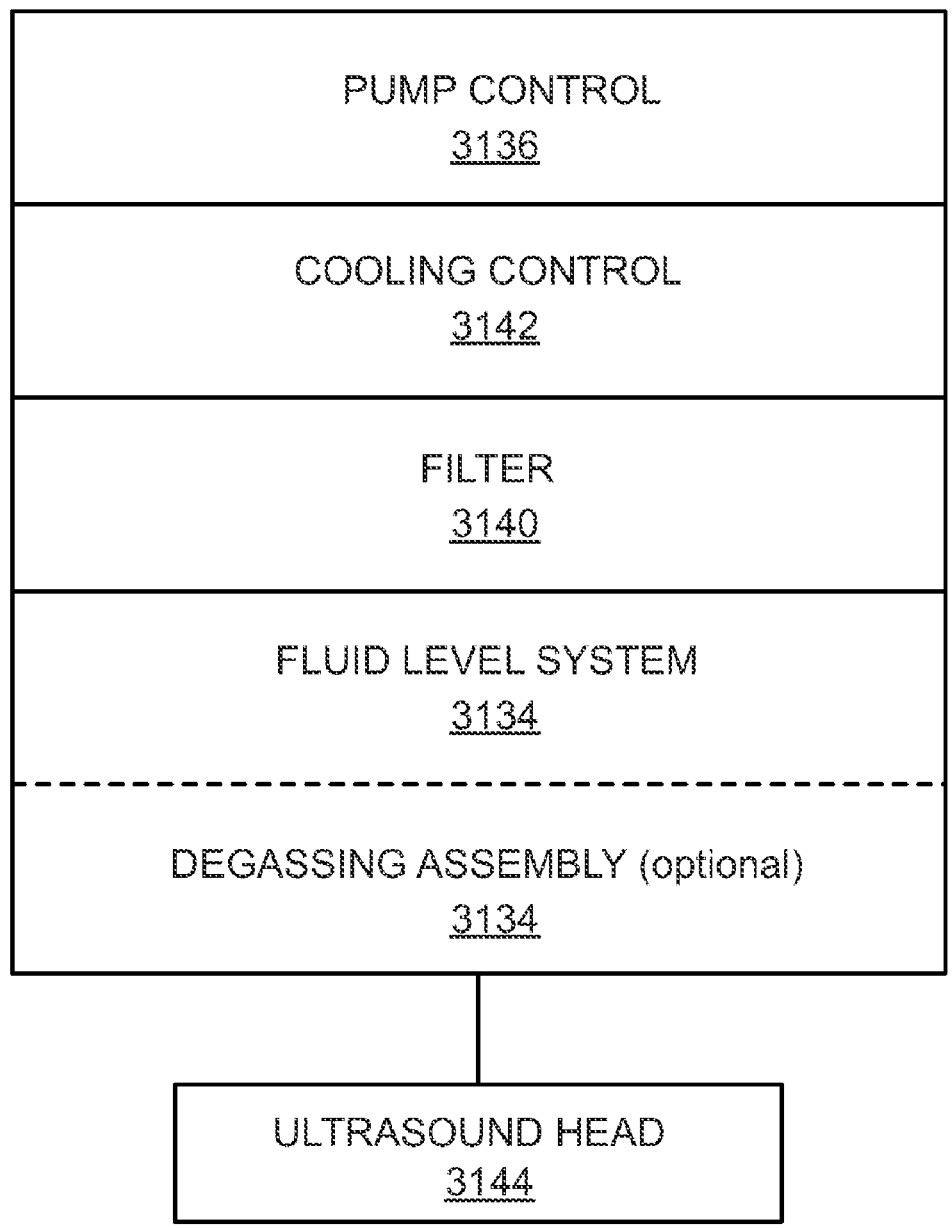
FIG. 12 is a block diagram of a medical ultrasound system having a degassing unit in accordance with an embodiment.

FIG. 12 is a block diagram of the fluidics subsystem of a medical ultrasound system in accordance with an embodiment. The fluidics system has a pump control 3136, an optional cooling control 3142, a filter 3140 and a fluid level system 3134. The fluid level system 3134 monitors the level of fluid in the fluidics system and ensures sufficient fluid is present for all fluidic system operations. The filter serves to remove particulate matter that might clog or negatively impact the system. The pump circulates the fluid through out the fluidics system. The pump control 3136 may be the same pump used in an optional degassing assembly 3138. Fluid is moved from the base unit to the ultrasound head 3144, and generally returns to the base unit in a complete fluid circuit.

The disclosed systems provide a number of advantages. For example, in some embodiments, the disclosed systems can function without a vacuum pump, which avoids the initial and ongoing expenses associated with vacuum pumps (i.e., initial cost of vacuum pump system components and related ongoing maintenance/repair costs). It further allows those systems to operate without the associated components required to maintain a degassed fluid environment for the fluid circulation system, further reducing costs and complexity of the fluidics system.

Figure 13:
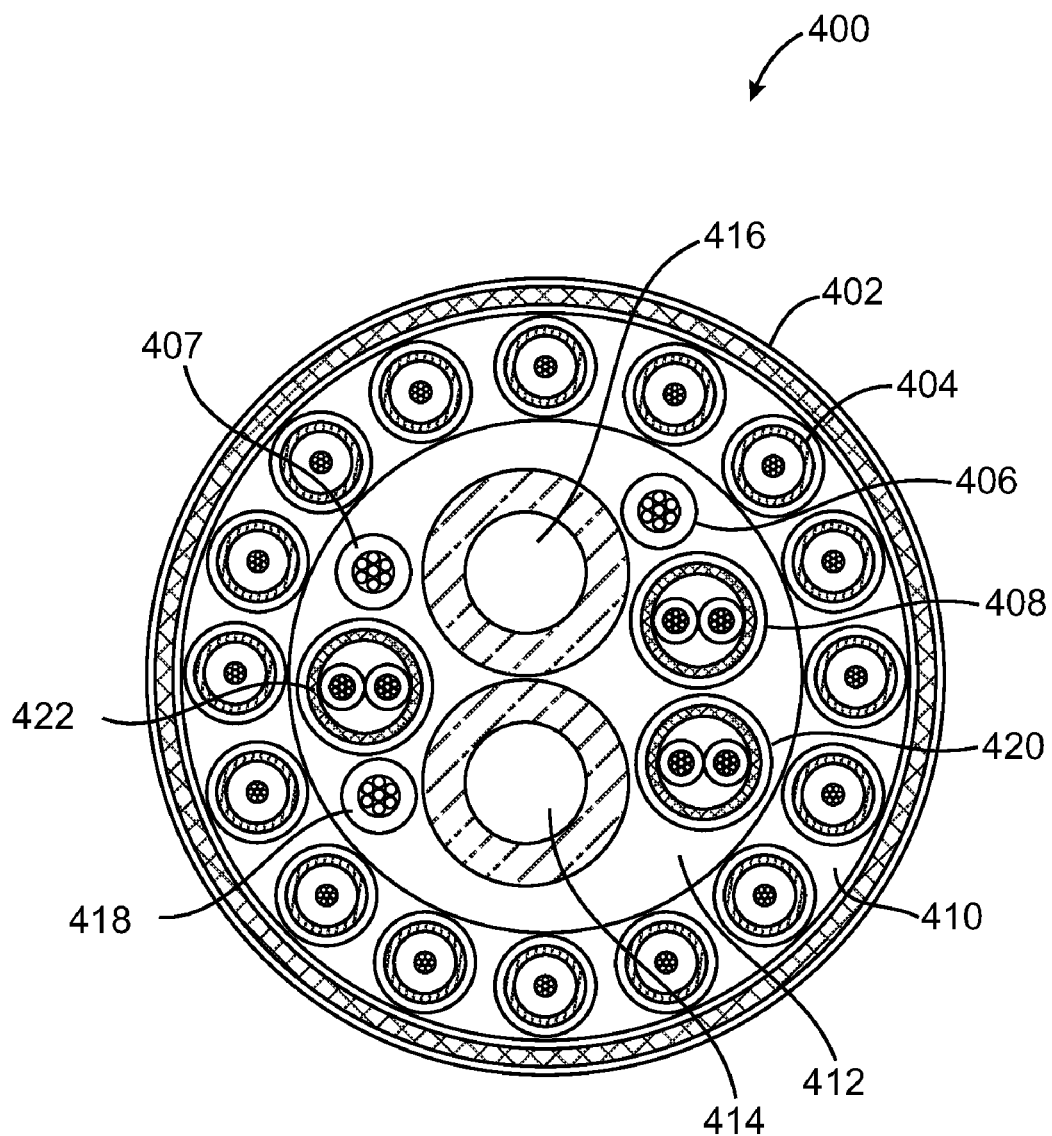
FIG. 13 is a cross section of a cable according to an embodiment.
Figure 35:
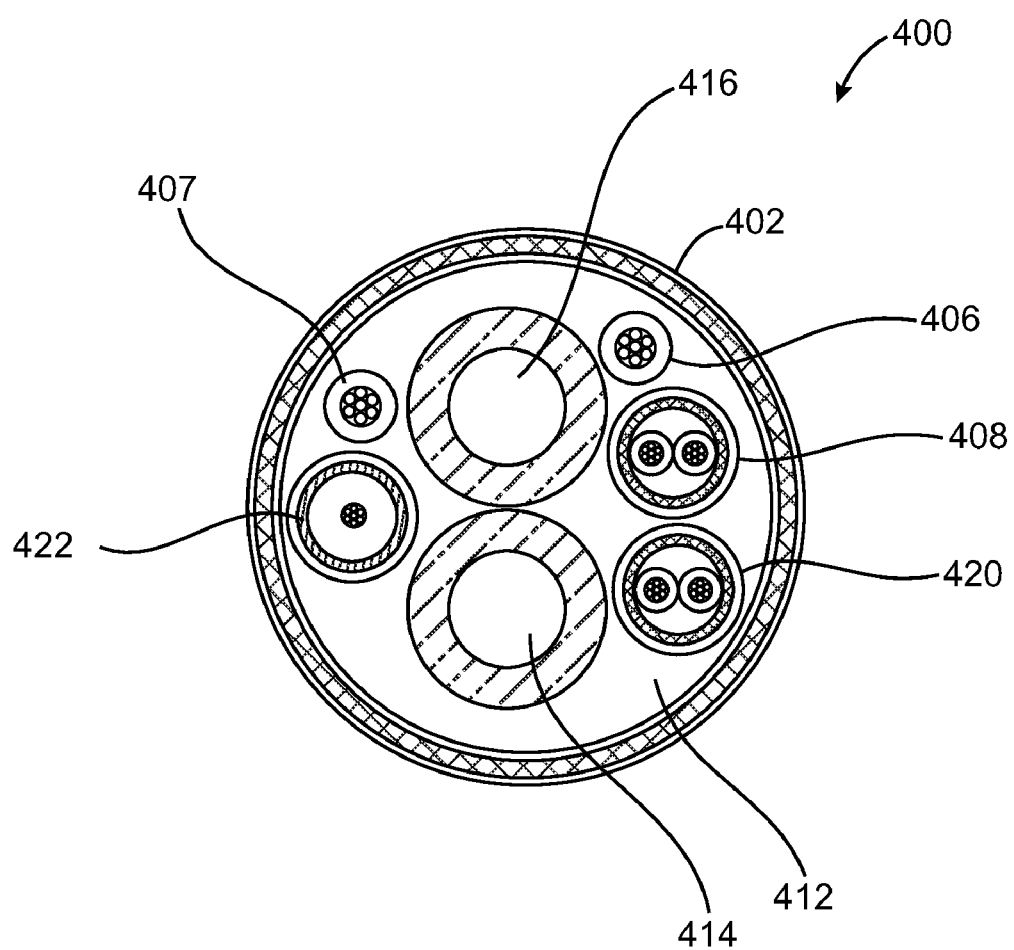
FIG. 35 shows an alternative embodiment of an interface cable.

A cross section of a interface cable 400 in accordance with an embodiment is shown in FIG. 13, with an alternate embodiment shown in FIG. 35, the alternate embodiment having similar components. The cable 400 has an outer sheath 402. This outer sheath may also provide shielding to the cable to prevent EM radiation from the cable, and physically protecting the cable. The outer sheath 402 surrounds a first ring of coaxial cables 404 arranged in a circular orientation and surrounded with an insulation layer 410. A filler layer 412 in the interior of the interface cable helps with both electrical shielding and water containment in case of a leak from water lines 414, 416. The coaxial cables 404 are used to provide drive signals and receive signals to/from each element of an array transducer in the treatment head in real time. If the treatment head does not utilize an array transducer, the coaxial cables 404 are assigned predetermined priority for driving a single element transducer. In the interior there are power lines 406, 407 carrying voltage from the main system 130 to the treatment head 500. The power lines 406, 407 can carry different voltages, while the electrical components within the therapy head 500 draw power based on one of the two voltages. A ground wire 418 is provided and serves as electrical ground return for all the electrical components in the treatment head regardless of the electrical voltage the component requires. Information can be relayed between the system base and the treatment head using two or more twisted pair wires 408, 420. A single twisted pair can be used (not shown) by multiplexed communication. In one aspect, the interface cable and the twisted pair wires are EM shielded, to eliminate EM radiation.

Figure 34:
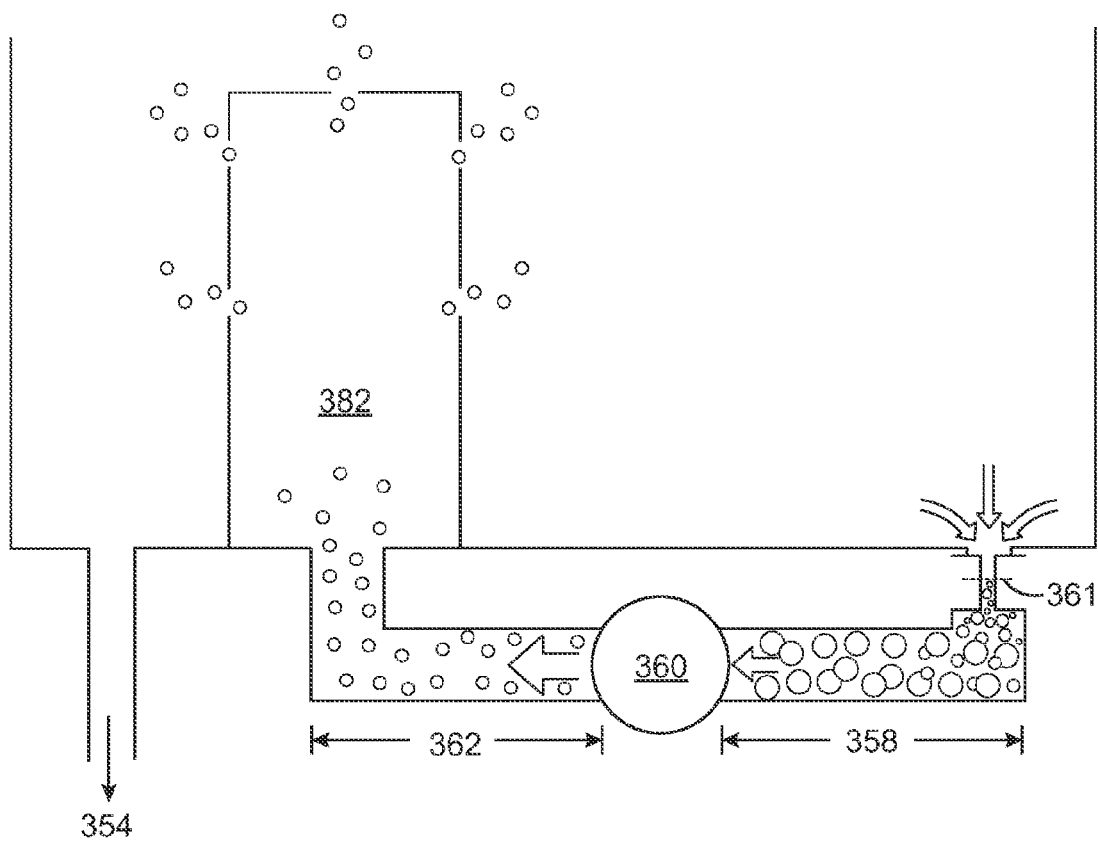
FIG. 34 illustrates the vacuum assembly of FIG. 9.

Alternatively the interface cable may use two power lines, one for power and the other for ground. In this embodiment, all components within the treatment head would use a single voltage, or have an adapter to allow use of a common voltage. The use of two twisted pair wires are retained for serialization of data from base to therapy head, and therapy head to base (FIG. 34). Alternatively a third two twisted pair may be used to reset/restart the therapy head by cycling power on and off (not shown).

Figure 14:
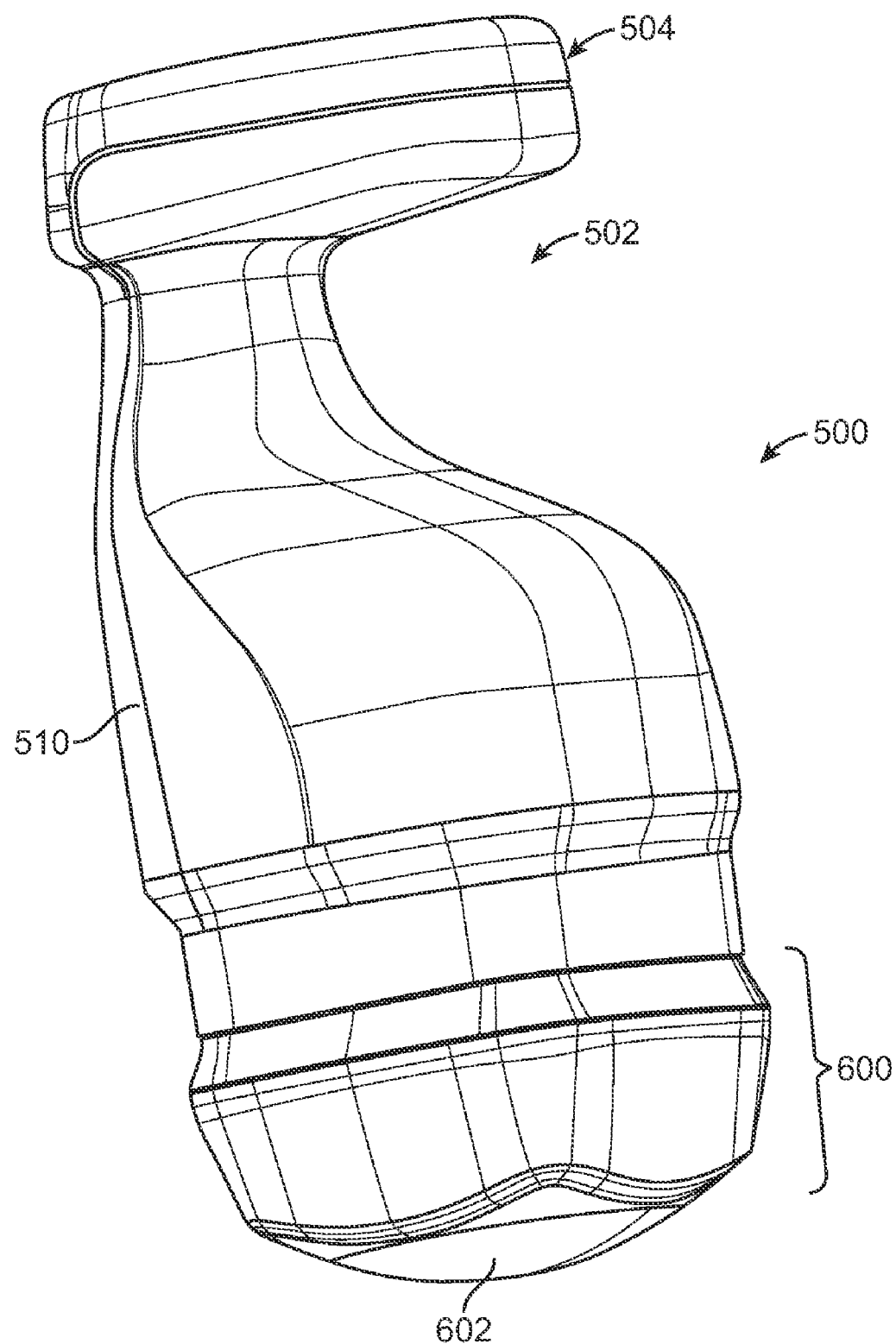
FIG. 14 is a perspective view of the treatment head according to an embodiment.

An embodiment of the treatment head 500 is now shown in FIG. 14, note the form factor and layout of the treatment head may take many forms. The treatment head 500 has an upper section 510 and a removable lower section 600. The upper section 510 has an indented grip area 502, which may be designed for being gripped by left or right handed persons with equal ease. The top of the upper section 510 has a handle guard 504. The bottom of the lower section 600 has an ultrasound transmission window 602. Generally the upper section contains a driver, such as a motor drive unit, and a variety of electronics necessary for the operation of the treatment head. The lower section contains an ultrasound transducer. The lower section is considered a "wet" environment, having a fluid surrounding the transducer, to provide an ultrasound coupling medium between the transducer and the transmission window. The fluid in the lower section may be any low molecular weight solution or liquid having the properties of low ultrasound impedance, high thermal mass. The fluid can be, e.g., water. In one aspect, the liquid is water that is substantially degassed, chilled and free of impurities (as described herein). Examples of water solutions for the lower section include, but are not limited to, degassed deionized water, degassed distilled water or de-gassed filtered water. In an aspect the lower section 600 is detachable, in the form of a cartridge.

Figure 15:
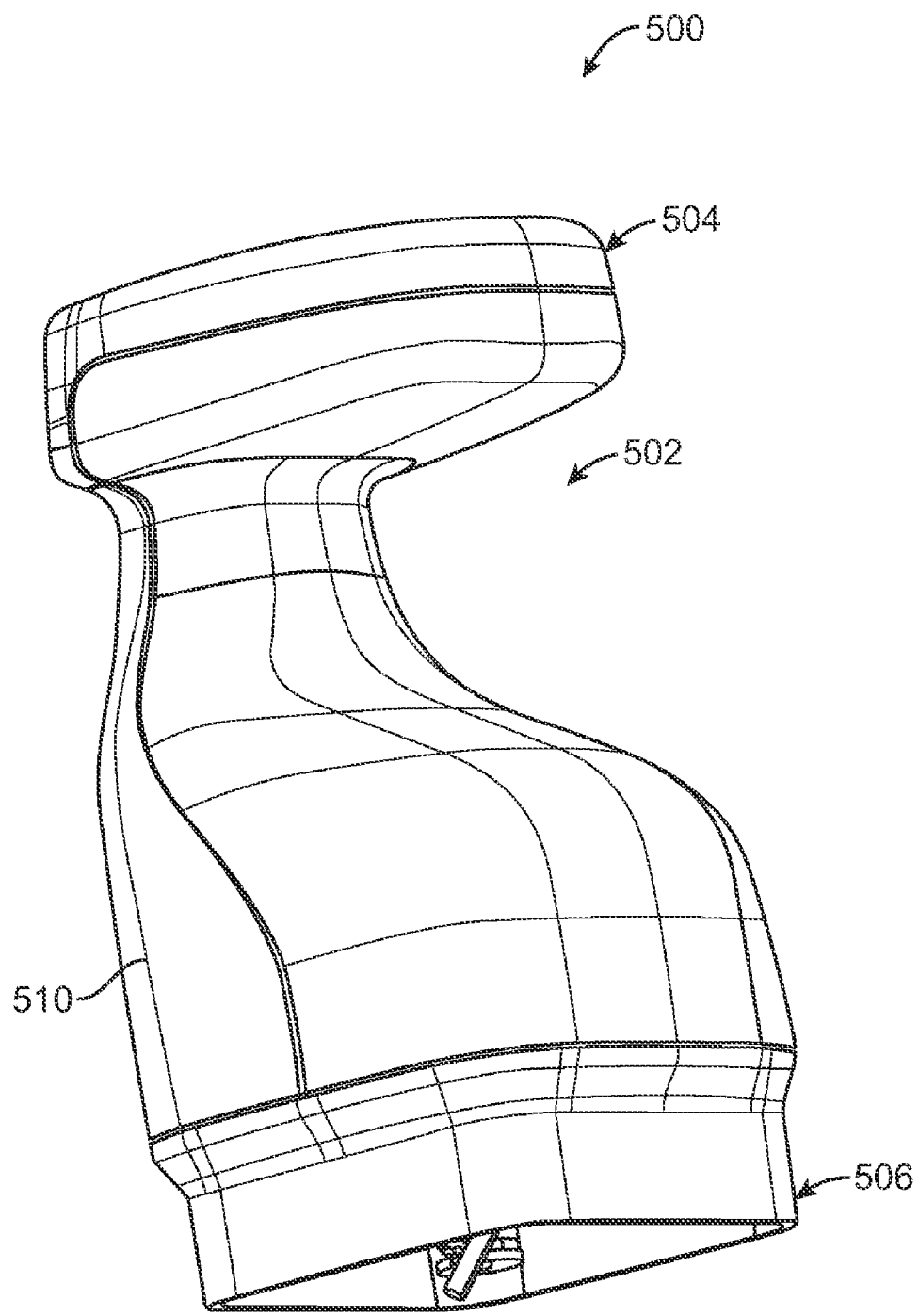
FIG. 15 is a perspective view of the treatment head according to an embodiment.

FIG. 15 provides a perspective view of the upper section 510 of an exemplary therapy head 500 with lower section detached. In this view the engagement collar 506 of the upper section is more evident.

Figure 16:
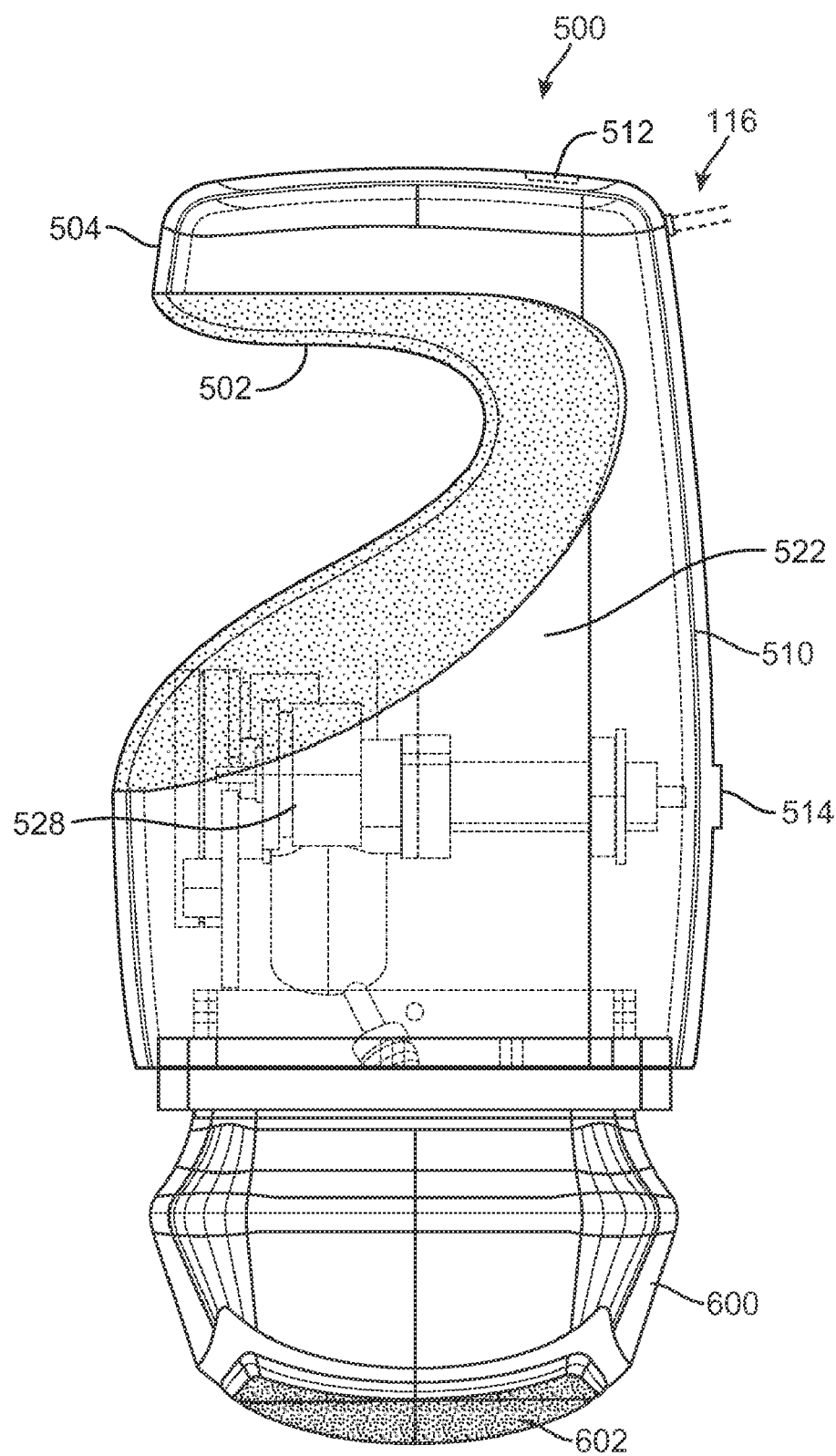
FIG. 16 is a transparent profile view with internal components of the treatment head according to an embodiment.

An example of one embodiment is shown in FIG. 16. The ultrasound head 500 has one or more cables 116 extending from it and going to the main body 130. The upper section 510 has a compartment 522 that typically is dry and houses wires, cables, a motor assembly, and/or other features for a transducer, which is mounted in the lower compartment 600. The lower compartment 600 preferably contains a coupling fluid, such as degassed water, which allows the transmission of ultrasound energy from the transducer to and through a window 602 located near the bottom of the lower compartment. Disposed within the upper compartment 510 is an actuation assembly 528. The actuation assembly 528 provides for control over the position/orientation of the transducer 900 located within the lower compartment 600.

The cable 116 can connect to the top portion 504 of the upper section 510. A treatment head controller board is positioned within the upper section 510 and receives the inputs from the interface cable 116. The treatment head control board also has the SERDES chip, and any other electronic components needed for the proper operation of the therapy head. An optional LED or other signal device 512 is provided to indicate the treatment head 500 is active. An optional trigger 514 is provided so a user may actuate an optional coupling liquid applicator device. The top section (the treatment head) has a grip section 502 can be adapted to be held in either a user's left or right hand.

In operation, a technician rolls the medical ultrasound system 100 adjacent to a patient. The technician grasps and moves the ultrasound treatment head 500 into the desired position. The ultrasound treatment head 500 is aligned so that the window 602 is in contact with the patient. The user interface device 102 may be operated to generate an appropriate treatment or diagnostic test. During use, the transducer mounted in the lower compartment 600 generates ultrasound energy, which may be used, for example, for the destruction of adipose tissue, as described in U.S. Published Application No. 2006/0122509, incorporated herein by reference. The actuation assembly 528 can be used to provide for simplified treatment procedures. For example, the ultrasound head 500 can be held in stationary contact with the patient while the actuation assembly 528 varies the position/orientation of the ultrasound transducer so as to apply therapeutic treatment to a local region of the patient using a scan pattern that provides a desired coverage, duration, spacing, etc.

As shown in FIG. 16, the therapy head 500 includes a lower compartment 600, or cartridge, and a therapy head body, or upper compartment 510. Although the upper compartment 510 is described as a "compartment," suggesting a hollow body, the compartment may contain many structures. In an embodiment, the upper compartment 510 houses operational components of the therapy head 500. The inside of the upper compartment 510 is usually dry and houses wires, cables, a motor assembly, electronics, and/or other features for a transducer 900 (FIG. 17), which is mounted in the lower compartment 600. In addition to the transducer 900, the lower compartment 600 preferably contains a fluid, such as degassed water 604, used to couple ultrasound energy from the transducer 900 to and through a flexible window 602 located near the bottom of the lower compartment.

The transducer 900 mounted in the lower compartment 600 may take various different forms and, in an embodiment, is movable so that it may focus toward various different locations of the window 602. An example of a transducer and movement system are described in commonly owned U.S. patent application Ser. No. 12/364,327, filed Feb. 2, 2009, and entitled "Therapy Head For Use With Ultrasound System." Other transducers and/or movement systems may be used. A transducer may also be fixed in the lower compartment 600.

Figure 17:
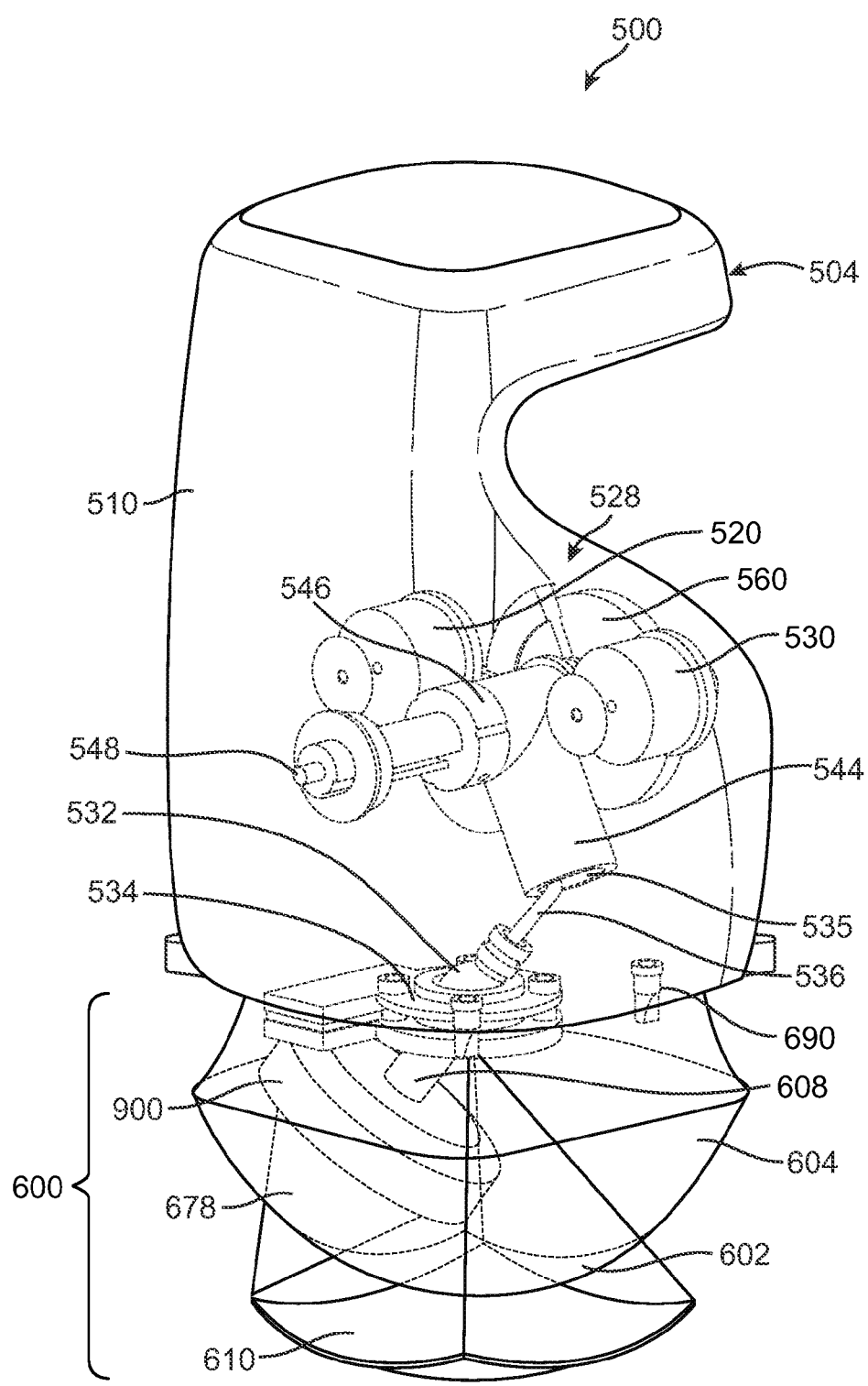
FIG. 17 is a transparent perspective view of FIG. 16.

FIG. 17 illustrates internal assemblies of a therapy head 500 similar to that shown in FIG. 16. Mounted within the upper compartment 510 is the actuation assembly 528. The actuation assembly 528 is coupled with an ultrasound transducer assembly 900 by way of a control arm 532. The control arm 532 may be configured to interface with and pivot within a receptacle 534 that is coupled with a partition that separates the upper compartment 510 from the lower compartment 600. In one aspect, the lower compartment 600 can be disengaged from the upper compartment 510. The lower compartment 600 is typically a sealed assembly that contains a coupling fluid, such as degassed water, that is used to transfer ultrasound energy transmitted by the transducer assembly 900. The receptacle 534 includes at least one fluid seal to prevent fluid from entering the upper compartment 510 from the lower compartment 600 when the two compartments are joined together. The seal may be one or more O-ring(s) around a spherical joint of the control arm 532. The control arm 532 includes a control arm upper end 536 disposed within the upper compartment 510. In the position/orientation shown, the ultrasound transducer assembly 900 is shown as transmitting focused ultrasound energy through the window 602 as illustrated by the ultrasound energy profile 610.

The actuation assembly 528 is operable to move the control arm upper end 536 so as to pivot the control arm 532 within the receptacle 534. The range of motion of the actuation assembly and the control arm 532 produces a coverage area 610 within which focused ultrasound energy can be directed in a controlled fashion (e.g., by using scanning patterns, scanning rates, energy transmission levels, etc.). When the lower compartment 600 is engaged to the upper compartment 510, the transducer assembly 900 is mechanically engaged to the control arm 532 through a control arm receptacle 548. Thus as the control arm 532 is moved by the actuation assembly 528, the transducer is moved in direct relation to the control arm 532.

In an embodiment, it is also possible for the receptacle 548 to move in a reciprocal fashion relative to the movement of the control arm 532. The movement of the receptacle 548 relative to the control arm 532 is merely a design choice feature which may be adjusted according to desire based on the intended range of motion, and adapting any position tracking and/or position sensor information gathered about the position of the transducer assembly 900.

The actuation assembly 528 according to an embodiment has a modified lead screw 548 (available from Haydon Kerk Motion Solutions, Inc., Kerk Products Division, 1 Kerk Drive, Hollis, N.H. 03049) with a pair of motors 556, 558 working to drive a carriage nut 546 over the screw rail. The motors 520, 530 may operate through a set of gears 560 to drive the screw rail. A carriage nut coupler 544 is moved by the actuation assembly 528 to drive the motion of the upper arm 536. The motion may be direct, reciprocal or any relation suitable for the movement of the transducer assembly 540. A union joint 535 connects the control arm 536 to the carriage nut coupler 544.

The lower compartment 600 may also feature a pressure compensator 690 to adapt the fluid pressure in the lower compartment 600 to variations in atmospheric pressure during use or shipment.

Figure 18:
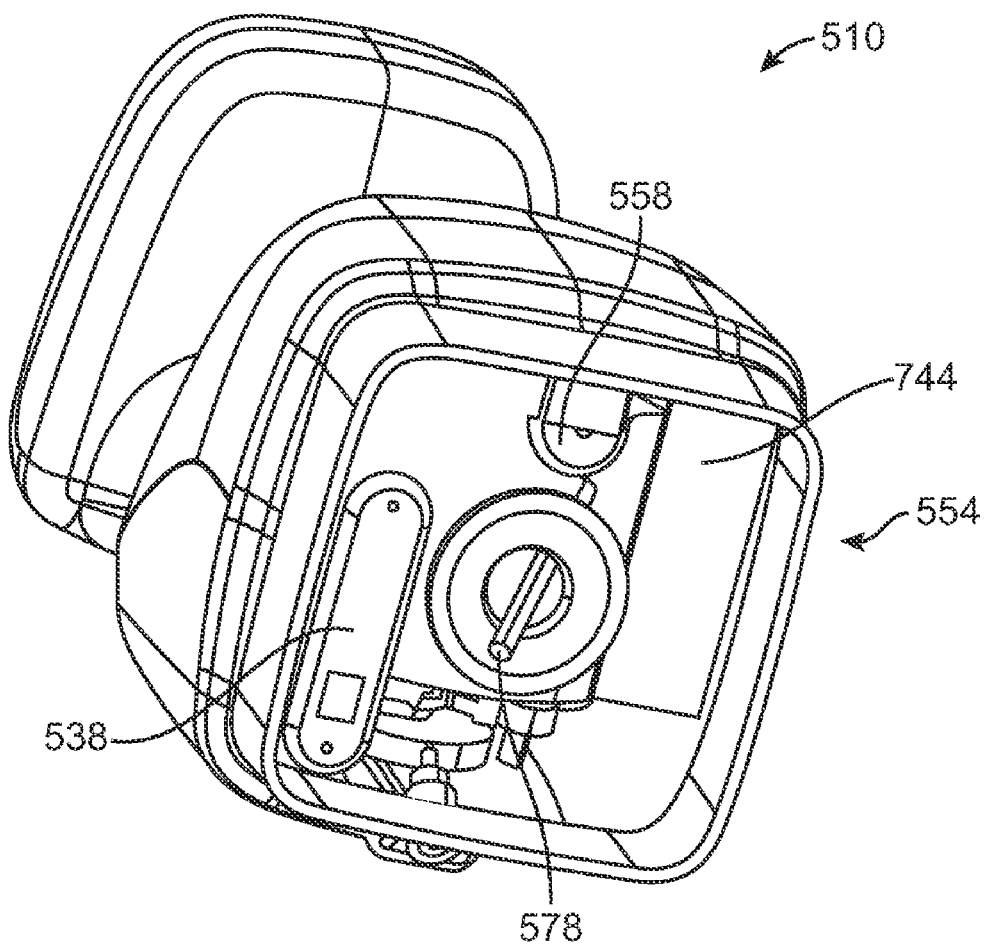
FIG. 18 is a bottom isometric view of the therapy head of FIG. 15.

A perspective view of the upper compartment 510 or treatment head with focus on the connector for the upper compartment and lower compartment is shown in FIG. 18. The upper compartment 510 has a recess 554 for mechanically engaging the cartridge. The TEC layer 744 is shown where it will abut the corresponding section of the lower compartment having the riser 772 or heat transfer plate 748. A control arm 578 for engaging and controlling the corresponding cartridge component for moving the transducer assembly is also shown. An electrical interface 638 is also provided for handling the various electrical interfaces required to properly control the transducer assembly, and monitor any sensors desired in the cartridge.

Figure 19:
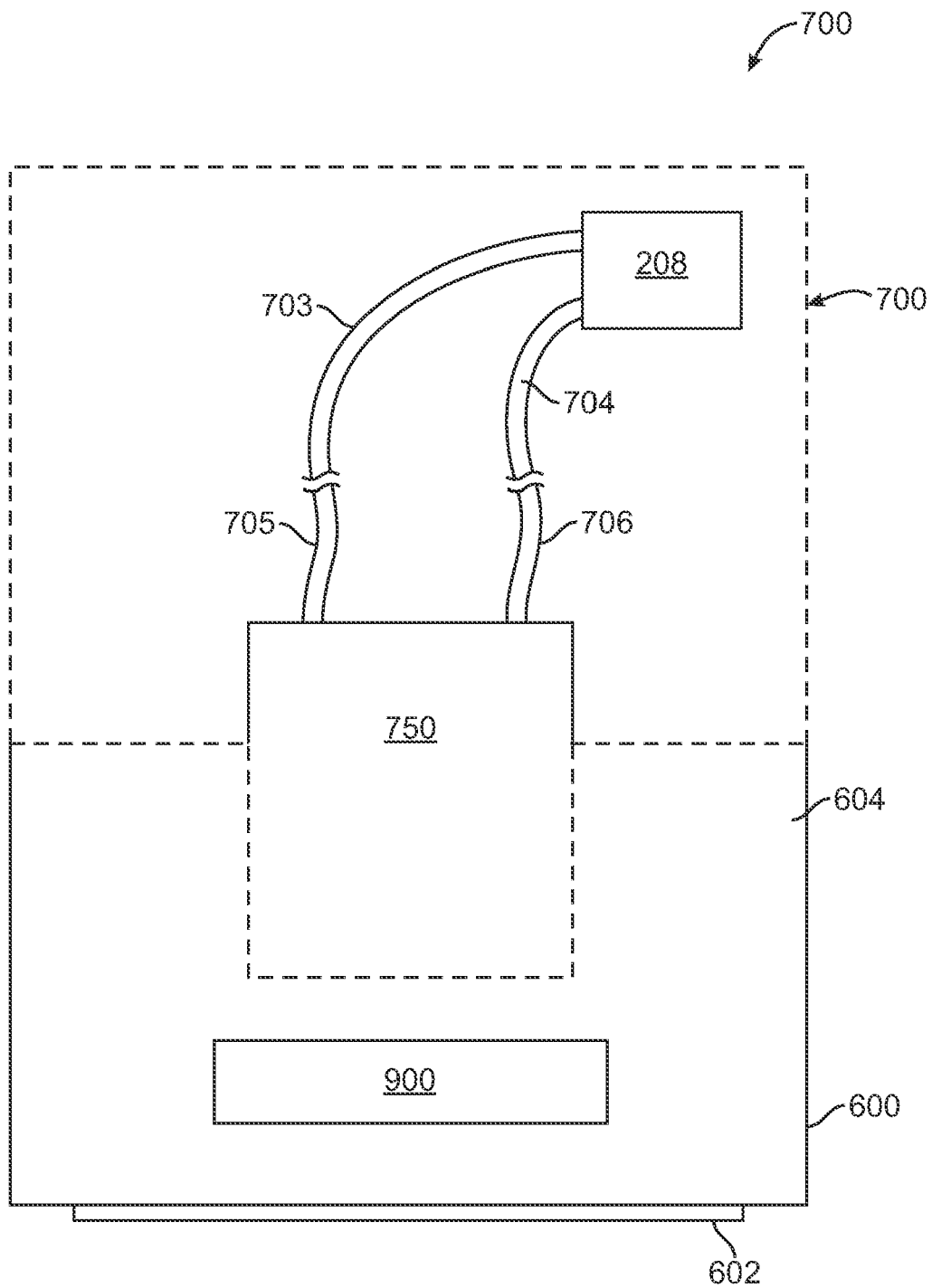
FIG. 19 is a schematic diagram representing some components of a medical ultrasound system in accordance with an embodiment.

In an embodiment, a cooling device 750 is affixed directly to the lower compartment 600 of the treatment head (See FIG. 19). A cooling device 750 is positioned to remove heat from the lower compartment 600 and dissipate heat either into the upper compartment 510, or to the exterior environment (outside the system). The cooling device 750 typically has a high capacity for heat transfer, and is also typically able to absorb and dissipate heat quickly. The cooling device 750 may be a stand alone device in the treatment head, or work in conjunction with a system in the base unit, such as a fluid circulations system 208. The fluid circulation system 208 may form a circuit with the cooling device 750 to form a cooling circuit 700, and have conduits for sending fluid to the treatment head 704, 706 and conduits for receiving fluid from the treatment head 703, 705. In one aspect the cooling circuit 700 also includes a chiller for removing heat from the fluid as it circulates into the system base from the treatment head. The fluid circulation system 700 may also have a fluid degas unit 300 as previously described.

In accordance with an embodiment, instead of circulating water through a cartridge of a therapy head, the lower compartment 600 is a sealed structure that includes the transducer 900 mounted therein. A compartment fluid 604, such as degassed water, surrounds the transducer assembly 900, and is sealed in the lower compartment 600 with the transducer assembly 900. The sealed lower compartment 600 is removable and replaceable, as a single unit with the coupling fluid 604 and the transducer 900. Thus, a technician does not have to break a seal or remove a transducer 900 from the fluid 604. Instead, a user may remove the cartridge 600 at any time, such as at the end of the useful life of the transducer assembly 900, then a new lower compartment 600 with a new transducer 900 sealed inside fluid 604 replaces the previous lower compartment cartridge 600.

In one aspect the fluid in a sealed cartridge may be degassed down to a level of 10 PPM dissolved oxygen or less. Dissolved oxygen may be used to measure the concentration of dissolved gasses because degassing operations tend to remove all dissolved gasses in equal proportion. The ratio of oxygen to other gasses is fairly constant, so reducing the oxygen content of a fluid also reduces the gas content of all other gases in the same ratio or proportion. The actual level of dissolved gas content that the fluid in the cartridge can tolerate before the acoustic path is adversely affected depends on the intensity of the ultrasound energy, the focal length of the transducer (either mechanically or electronically focused), the pulse repetition frequency (PRF) as well as other components of determining the transducers operation. Generally the combination of these electronic and power considerations can be balanced to allow a higher level of dissolved gases. If the transducer is operating at power and performance factors where dissolved gases are more likely to cause problems in the sealed environment (for example, by producing cavitation or micro streaming effects) then the dissolved gas level may be lowered to reduce or eliminate these negative effects. Generally a desired level of dissolved oxygen to achieve in a sealed transducer cartridge is less than 10 PPM. In many aspects, levels may be maintained at around 5 PPM.

The lower compartment 600 includes a profile that fits to a profile of the upper compartment 510 so that the two components may be removably attached to one another. If desired, a latch or other lock may be provided to releasably lock the two attached components. A tool may be used to assist in the removal of the cartridge 600 and the upper section 510 of the treatment head 500, or to assemble the two components into a working treatment head 500.

Figure 20:
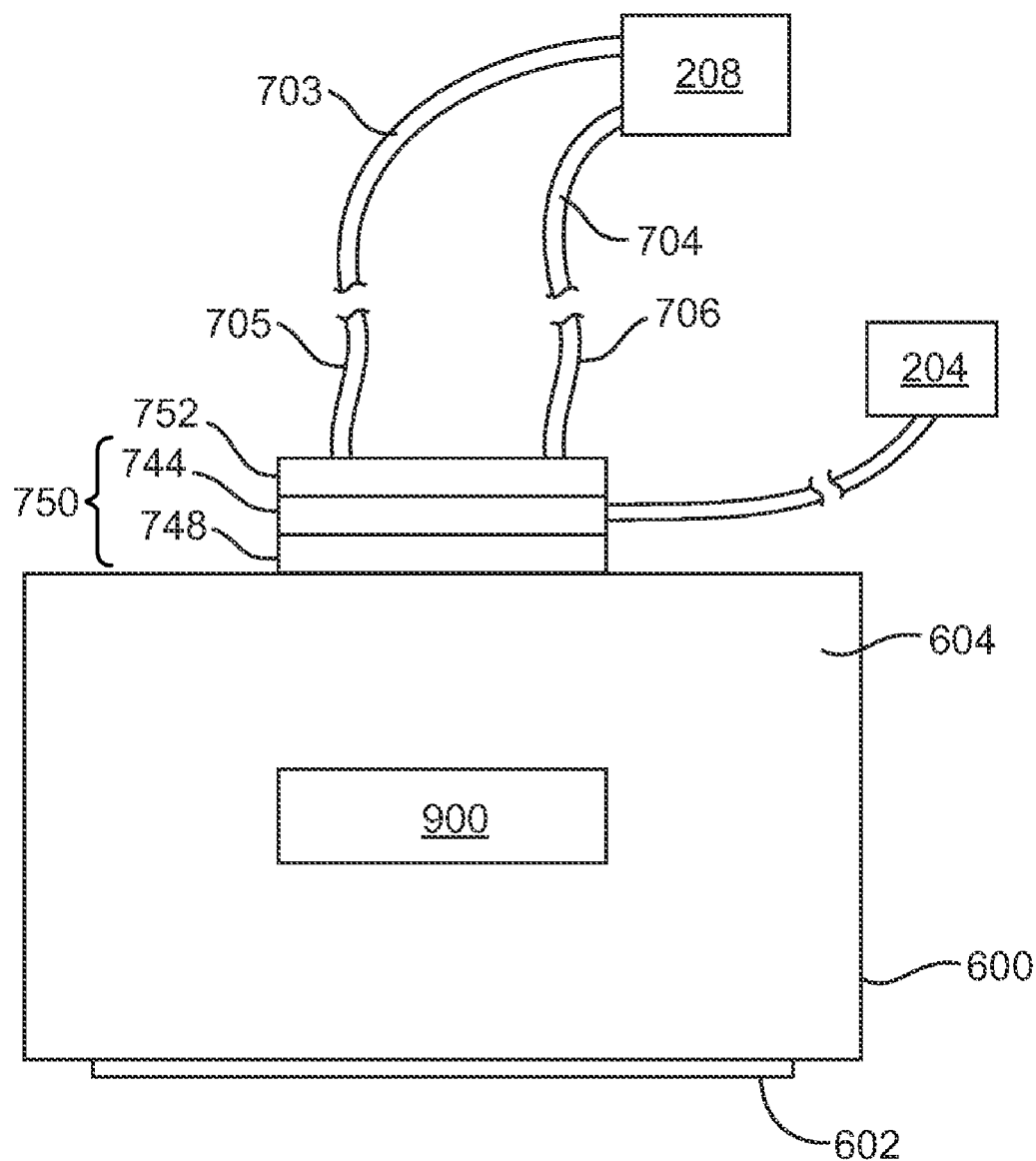
FIG. 20 is a schematic diagram representing some components of a medical ultrasound system in accordance with an embodiment.

The transducer assembly 900 may generate heat during use, heating the fluid 604 (FIG. 20). In accordance with an embodiment, a cooling device 750 is provided for cooling of the fluid 604 sealed in the lower compartment 600. In an embodiment, the cooling device 750 includes a thermoelectric device 744, but other devices may be used. As is known, a thermoelectric device, such as the thermoelectric device 744, is designed so that electric voltage is converted to a temperature difference across the thermoelectric device. The temperature difference results in a cold side and hot side of the thermoelectric device 744. In the diagram shown in FIG. 20, the bottom side of the thermoelectric device 744 is a cold side, and the top side is a hot side. The thermoelectric device 744 is connected to a power source 204, such as a battery, an AC/DC converter, or another suitable power source, for providing voltage to the thermoelectric device 744. The power source 204 may be mounted within the therapy head or may be connected via wires from another location, such as the base unit 130. As electric voltage is provided by the power source 204, a temperature differential is created across the thermoelectric device 744, creating the cold and hot sides.

In the embodiment shown in FIG. 20, a heat transfer plate 748 is positioned between a cold side of the thermoelectric device 744 and the fluid 604. The heat transfer plate 748 is utilized to remove heat from the fluid 604 and transfer the heat to the cold side of the thermoelectric device 744.

A structure for removing heat from the thermoelectric device 744 may be attached to the hot side of the thermoelectric device 744. In the embodiment shown in the drawings, this structure is a heat exchanger 752. The heat exchanger 752 includes at least one fluid in conduit 706 and at least one fluid out conduit 705. The heat exchanger 752 may be, for example, a manifold with a serpentine or parallel fluid path through, although other structures or methods for heat removal may be used.

In an embodiment, the thermoelectric chip layer 744 includes one or more thermal electric chip(s) (TEC). Multiple chips may be placed in an array to transfer heat from the lower compartment 600 (for example, TEC chips may include MELCORE CP1.0-63-05L 16.6 watt TECs (Melcore, 1040 Spruce St., Trenton, N.J. 08648)). As described below, these TECs may be permanently or releasably attached to the components that remove heat from the lower compartment 600. A lower heat transfer plate 748 can be bonded to the lower compartment 600, and absorbs heat from the lower compartment 600 either by thermal convection from the lower compartment 600, as through a heat sink or heat transfer plate 748, or by being in direct physical contact with the fluid solution 604 within the lower compartment 600. In the latter case, the heat transfer plate 748 is fitted into the compartment wall of the lower compartment 600. When the lower compartment 600 is attached to the upper compartment 510, the lower heat transfer plate 748 is releasably connected to the TEC layer 744. The TEC layer 744 has power from a power supply 204. Proper use of the TEC allows a thermal gradient to be established in the TEC so the cool side of the TEC faces the lower heat transfer plate 748. Heat absorbed from the lower compartment fluid 604 is transferred to the TEC through the coupling agent between the lower heat transfer plate 748 and the TEC layer 744. The thermal coupling material between the TEC and lower compartment heat transfer plate is a material such as grease or gel that allows for good thermal contact between the two layers, but does not form any permanent bond, thus allowing for releasable engagement of the TEC from the lower compartment on demand.

The TEC layer 744 can be bonded in a more permanent fashion to the upper heat transfer layer 752, by way of a thermally conductive epoxy or resin. The upper heat transfer layer 752 has a water basin for water circulation from the base unit. A fluid circulation system 208 pumps water through the fluid conduits 704, 706, with at least one line coming from the base unit 130 and going into the upper thermal transfer layer 752, while the other conduit brings warm fluid back to the fluid circulation system 208. As previously described, the fluid circulation system can include a chiller, so the warm fluid returning to the base unit is chilled prior to being pumped back to the thermal transfer layer 752. The heat exchanger 752 may be a manifold that is arranged to permit a cooling fluid, such as water, to flow through. The fluid enters the inlet conduit 706 and exits via the outlet conduit 705. The flow of fluid through the heat exchanger removes heat from the heat exchanger 752, which in turn removes heat from the hot side of the thermoelectric device 744.

Figure 21:
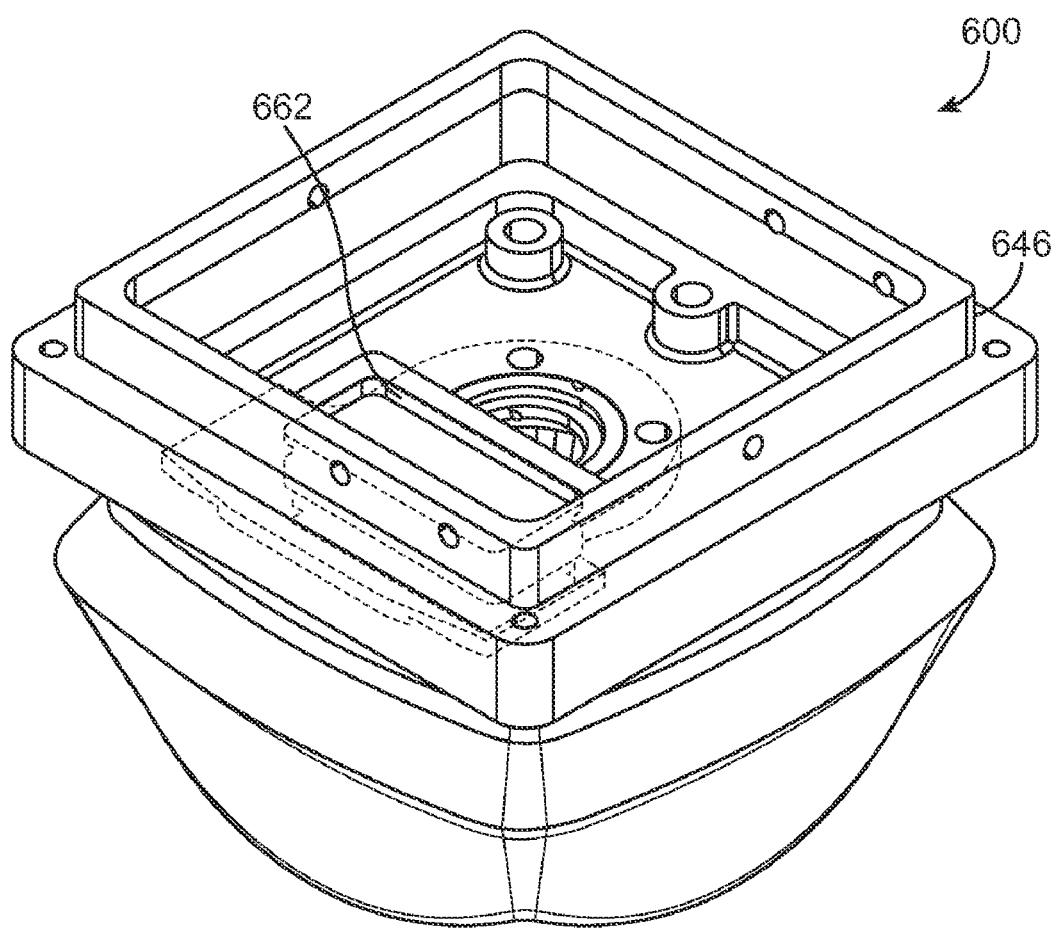
FIG. 21 is a perspective view of a lower compartment, or cartridge, for the therapy head of FIG. 16 in accordance with an embodiment.

As discussed above, the lower compartment 600 may be replaceable as a unit, with the fluid 604 of the lower compartment being in a closed system that is never opened by a user, even during replacement of the cartridge/lower compartment 600. An example of the removable lower compartment 600 is shown in FIG. 21. In this embodiment, a flange 646 extends upward from the lower compartment 600 and is removably attachable to a lower surface of the upper compartment. The portion of the lower compartment 600 used to engage the upper compartment is shown having a recess 662 where the lower compartment heat transfer plate 748 is fitted with a form fitting riser 772 to fit in the recess 662. The form fitting riser 772 may form a flush or recessed fit in the recess 662 when assembled. When the lower compartment 600 is attached to the upper compartment, the TEC layer lines up with and is coupled to the heat transfer layer 748 via the form fitting riser 772. In the embodiments shown in FIGS. 21-25, the thermoelectric device is connected directly to the heat exchanger using a releasable heat transfer material, such as heat transfer grease, pad or gels. Note the lower compartment heat transfer plate may be permanently bonded to the TEC layer using an epoxy if the lower compartment is adapted to fit to the lower heat transfer plate instead of the TEC layer when the lower compartment and upper compartment are engaged.

Figure 22:
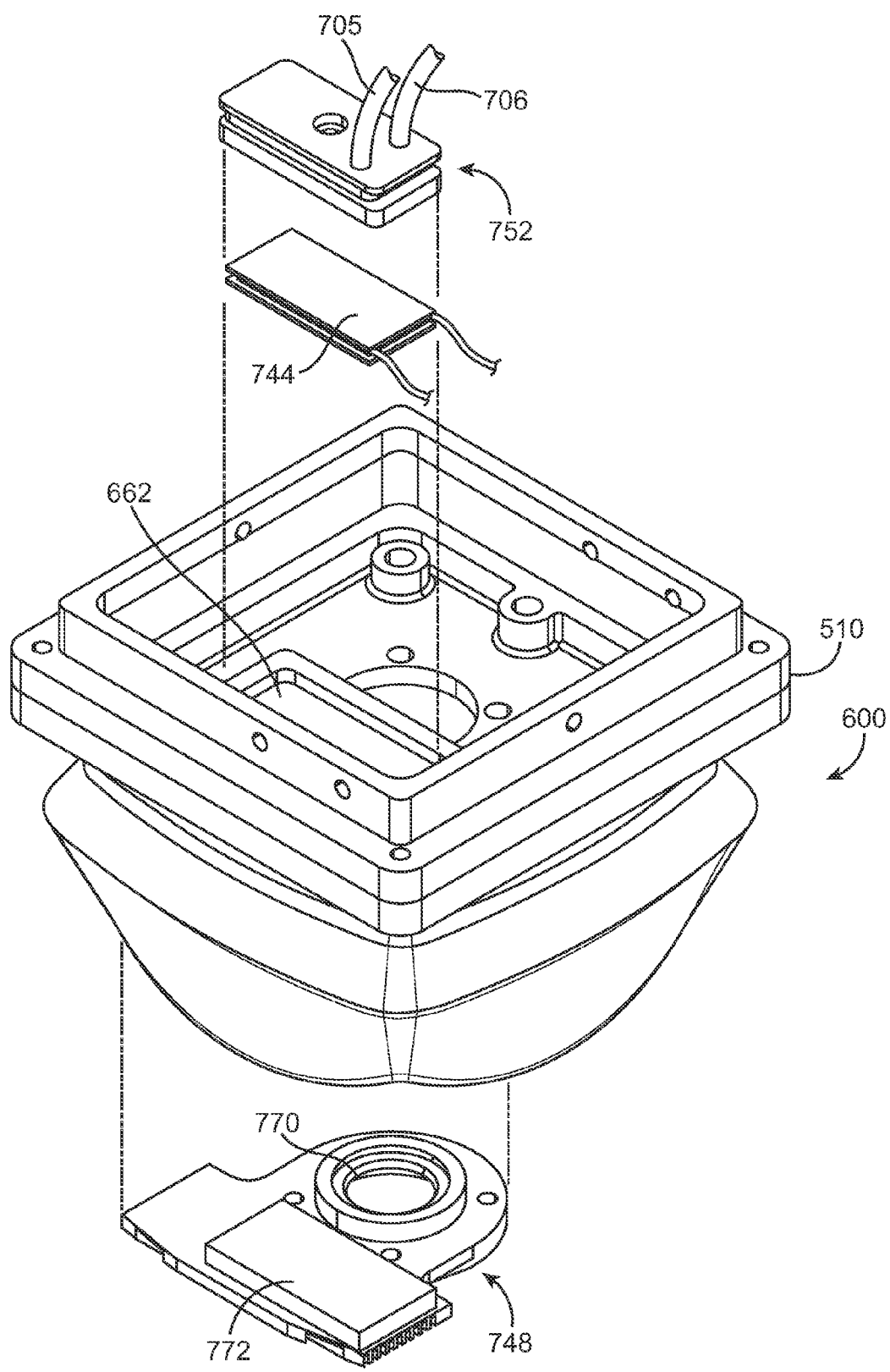
FIG. 22 is an exploded perspective view of the lower compartment of FIG. 21.
Figure 23:
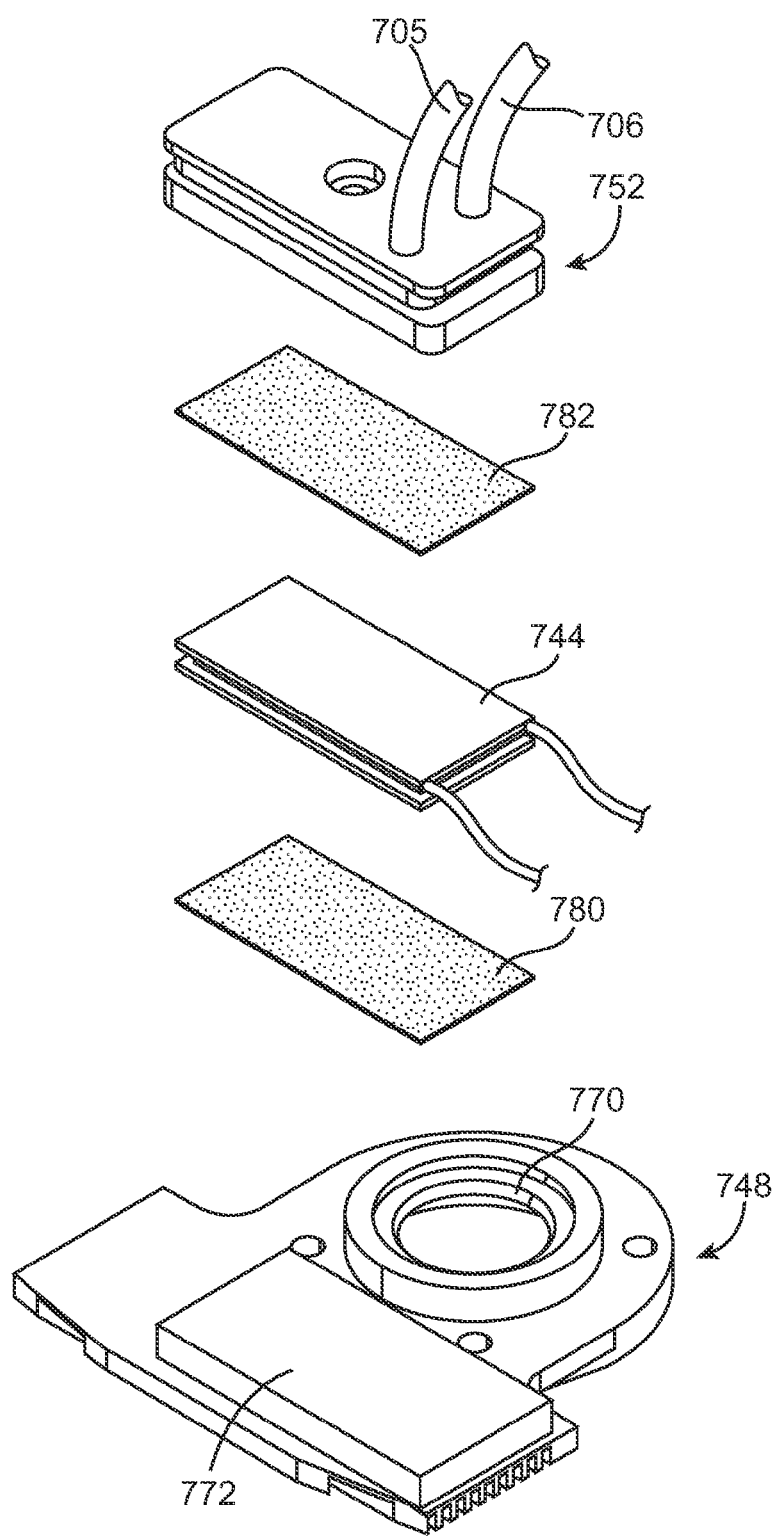
FIG. 23 an exploded perspective view of a thermoelectric device stack and related components for the therapy head of FIG. 22.

An exploded view of the major component stacks of an exemplary system are shown in FIG. 22. Here the TEC layer 744 is integrated into the bottom section of the upper compartment. The heat transfer plate 748 may extend along a top surface of the fluid 604 to provide large area of contact between the heat transfer plate and the fluid 604. The heat transfer plate 748 includes a central opening 770. The opening 770 is designed to receive a controller mechanism for movement of the transducer assembly 900, as described in application Ser. No. 12/364,327, cited above. A heat transfer plate riser 772 is included on one side of the heat transfer plate 748 and extends upward into the aperture 662.

The thermoelectric device 744 is attached to the top of the riser 772, for example, as described above, by a heat transfer material (shown by the reference numeral 780 in FIG. 23) or other suitable adhesive or structure that is thermally conductive. The heat transfer material 780 between the thermoelectric device 744 and the top of the heat transfer plate riser 772 maintains a thermally conductive bond between the riser 772 and the thermoelectric device 744 but, in an embodiment, is releasable. As an example, the heat transfer material 780 may be held in place through capillary attraction when the lower compartment is connected to the upper compartment. Some adhesion may be provided to make a solid bond between the components, but the bond is preferably releasable. If a permanent bond is desired, the heat transfer material may be an epoxy. If a releasable option is desired, the heat transfer material can be a pad or grease.

Similarly, the heat exchanger 752 is attached to the hot side of the thermoelectric device 744 by a second heat transfer material 782 or other suitable heat conductive connecting structure. The bond here is also thermally conductive. The heat transfer material 782 in the upper section 510 can be an epoxy or other permanent bonding material.

The fluid circulation system 208 (FIG. 20) is positioned, for example, in the base 130. The fluid circulation system 208 pumps a fluid, such as temperature controlled water, in a circuit between the pump and the heat exchanger 752. The fluid from the pump flows in the inlet 706 and out of the outlet 705. In an embodiment, conduits 703, 705 between the fluid circulation system 208 and the heat exchanger 752 are thermally conductive so that heat removed by the water from the heat exchanger 752 dissipates as the water travels on the round trip from the heat exchanger, through the pump, and back to the heat exchanger. As such, a chiller may not be needed to remove heat from the water. Instead, the thermal loss of the system results in the water being cooled before returning to the heat exchanger 752. If the fluid is chilled, the outlet route 705 and pump input line 703 may be thermally conductive, while outflow pump line 704 and treatment head inlet 706 are thermally insulated. Note that while one pair of conduits is designated as the inlet pair and the other as the outlet pair, the conduits are generic in the sense that the flow direction can be reversed, so long as fluid flows in a circuit between the water circulation system in the base and the treatment head.

The use of a chiller or thermally conductive lines will depend largely on the amount of heat needed to be removed from the cartridge 600. If the transducer assembly operates in a mode where virtually no heat is generated (for instance, in a low pulse repetition frequency diagnostic mode), then thermally conductive conduits would be amply sufficient to keep the temperature state of the cartridge at a desired constant level. However if the transducer were operated in a very high power therapeutic mode, the amount of heat build up in the cartridge 600, and thus the cartridge internal degassed water 604 would be high enough to require the use of chilled fluid to help draw off the heat through the cooling device 750. In one aspect the system is equipped with both thermally conductive fluid conduits where needed, and a chiller as part of the fluid circulation system 208. That way the system may automatically regulate the use of the chiller based on thermal temperatures detected in the lower compartment 600. Detection could be achieved through the use of heat sensors in the lower compartment 600, bathed in the coupling fluid 604, or able to sense the temperature of the heat transfer plate 748. Optionally the chiller in the fluid circulation system may be manually controlled.

The temperature of the lower compartment/cartridge 600 may also be used to reduce a patient's skin sensation. Similar to the use of a cold pack to reduce pain, the cartridge may be regulated to achieve a low enough temperature to reduce skin sensitivity to therapeutic ultrasound treatments.

As described above, the lower compartment 600 is a sealed system that contains the transducer assembly 900, the transducer fluid 604, and the heat transfer plate 748. This sealed system may be removed by removing the lower compartment 600 from the therapy head 500. During removal, the temporary or releasable adhesive (e.g., the heat transfer material 780), allows release of the heat transfer plate 748 from the thermoelectric device 744. In this manner, the heat transfer plate 748 releases from the thermoelectric device 744 when the lower compartment 600 is removed from the upper compartment 510, allowing the thermoelectric device 744 and the heat exchanger 752 to remain in the upper compartment 510 when the lower compartment 600 is removed and replaced. Alternatively, these pieces may remain attached to the lower compartment 600 and may be replaced as well, but, by leaving the thermoelectric device 744 and the heat exchanger 752 within the upper compartment 510, no detachment or other reconfiguration of wiring for the thermoelectric device 744 or fluid input or output for the heat exchanger 752 is required. In addition, because these components remain in the upper compartment, the expense of replacing them is avoided.

During the treatment process, the transducer assembly 900 generates heat. If the transducer assembly 900 is overheated, damage to the transducer may occur. In the embodiment of the therapy head 500 shown in the drawings, the heat of the transducer assembly 900 is dissipated in the fluid 604. This heat, in turn, is removed so that cooling may continue and/or so that the therapy head 500 does not become too hot to damage the transducer or to be placed against a patient. In accordance with an embodiment, the thermoelectric device 744 is used to remove heat from the fluid 604 so that overheating is not an issue.

During operation of the therapy head, the power supply 204 supplies voltage to the thermoelectric device 744, which generates a heat differential between the thermoelectric device's hot side (upper side in FIG. 20) and its cold side (the downward side). The thermal electric device can be selected based on the amount of cooling wattage desired to be removed from the system, and the capacity for the fluid cooling system to remove the corresponding cooling wattage from the thermal electric device representing the cooling wattage cooled from the lower compartment 600, and the amount of electrical wattage put into the thermal electric device to achieve the desired cooling from the lower compartment. Because thermal electric device cooling is not 100% efficient, the fluid cooling heat exchanger connected to the thermal electric cooling device in the upper compartment 510 of the therapy head 500, typically is able to remove the combined thermal wattage of the cooling wattage from the lower compartment 600 and electrical wattage input into the thermal electric device to achieve the desired cooling wattage. For example, if in application the thermal electric device requires 10 electrical watts to achieve 6 cooling watts then the heat exchanger cooling system should be capable of removing 16 thermal watts through the hot side of the thermoelectric device to achieve the desired 6 watts of cooling. While this system is not as efficient as direct cooling of the lower compartment, it does allow the lower compartment to remain completely sealed, which provides additional benefits and ease of use.

In an embodiment using TEC devices, multiple TECs can be desirable to remove more heat rather than a single large TEC. Larger devices may have a diminishing return on efficiency, higher thermal transfer efficiency may be maintained by using smaller wattage drawing TECs. Thus the TEC layer may have numerous TEC devices arranged in a flat pattern. The heat transfer plate 748 could abut all the TEC devices arranged in the TEC layer. Likewise the heat transfer device 752 of the upper compartment would abut all the upper surfaces of the TEC layer simultaneously. The size, pattern and energy draw of the TEC layer 744 may vary substantially. Though a rectangular recess 662 is shown for receiving the TEC layer, the recess may be any size or shape to accommodate the TEC layer. The layer (and recess) orientation need not be horizontal, and a combination of multiple recess/aperture ports may be used to mate with multiple TEC layers distributed around the interface between the upper compartment 510 and the cartridge 600. The physical limit of the upper compartment 510 that interfaces with the recess 662 can be the TEC layer 744.

To remove heat from the hot side of the thermoelectric device 744, the fluid circulation system 208 has a pump to pump a fluid, such as water, through the heat exchanger 752. The water takes a serpentine path or parallel path through the heat exchanger 752 and removes heat as it flows through the heat exchanger. As such, the cold side of the thermoelectric device 744 constantly removes heat from the sealed degassed water 604 in the lower compartment 600. In this manner, the lower compartment 600 may be maintained at a desired temperature. The heat in the heat exchanger water is removed through the thermal losses in the system, or may be removed in another manner, such as a downstream chiller. However, by using thermal losses in the conduits, passive cooling occurs, and additional heat removal devices are not required. As such, the passive cooling by the conduits to and from the circulation system 208 reduces expense and eliminates maintenance issues with respect to a chiller or other active cooling system.

When a user desires to replace the lower compartment 600, the heat transfer plate 748 is removed with the lower compartment 600, and the thermoelectric device 744 and everything above it remain attached to the upper compartment 510. Another lower compartment 600 may then be attached to the upper compartment 510, and then the therapy head 500 is ready for use again.

Figure 24:
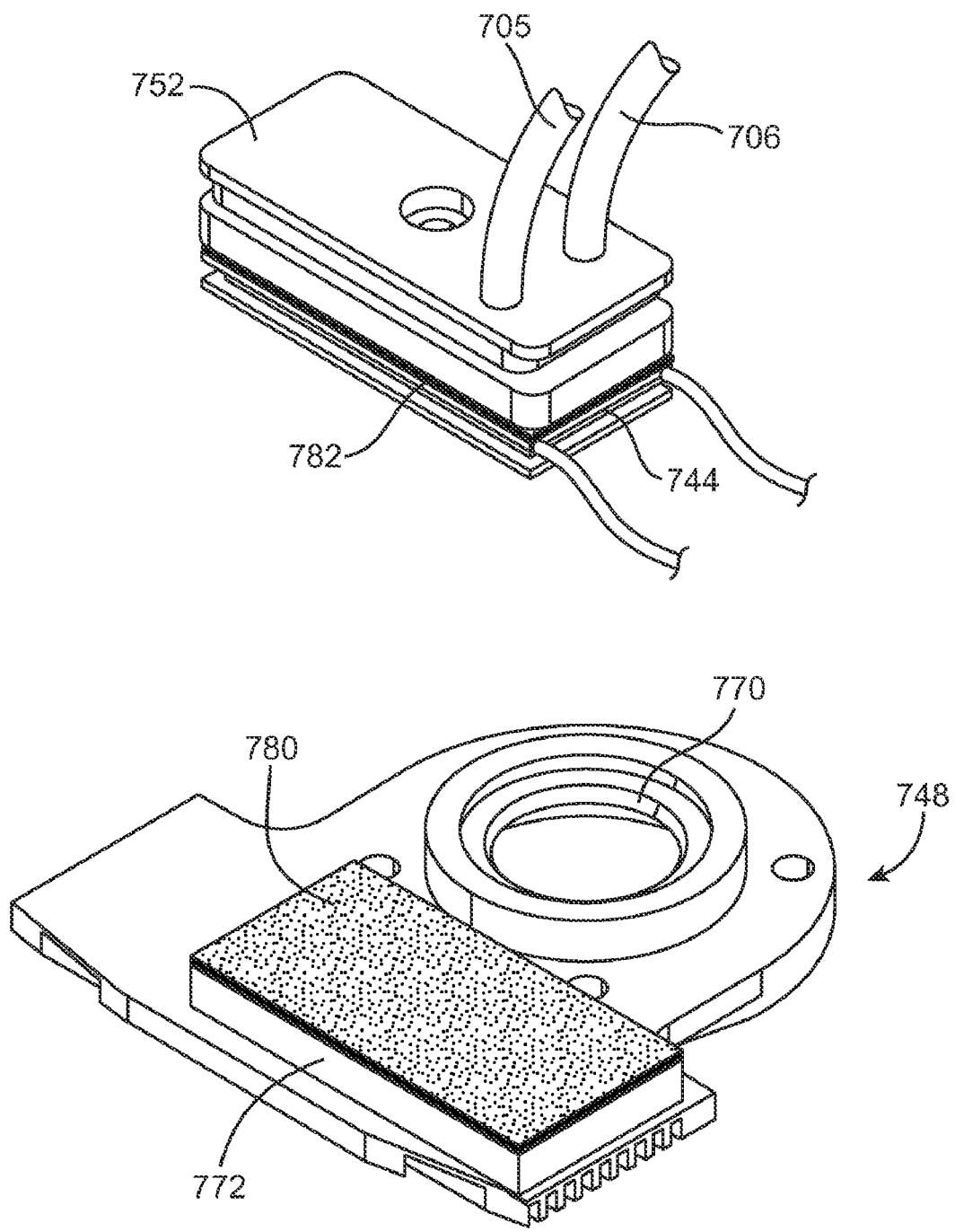
FIG. 24 is a perspective view of the upper and lower compartment thermoelectric device stacks.
Figure 25:
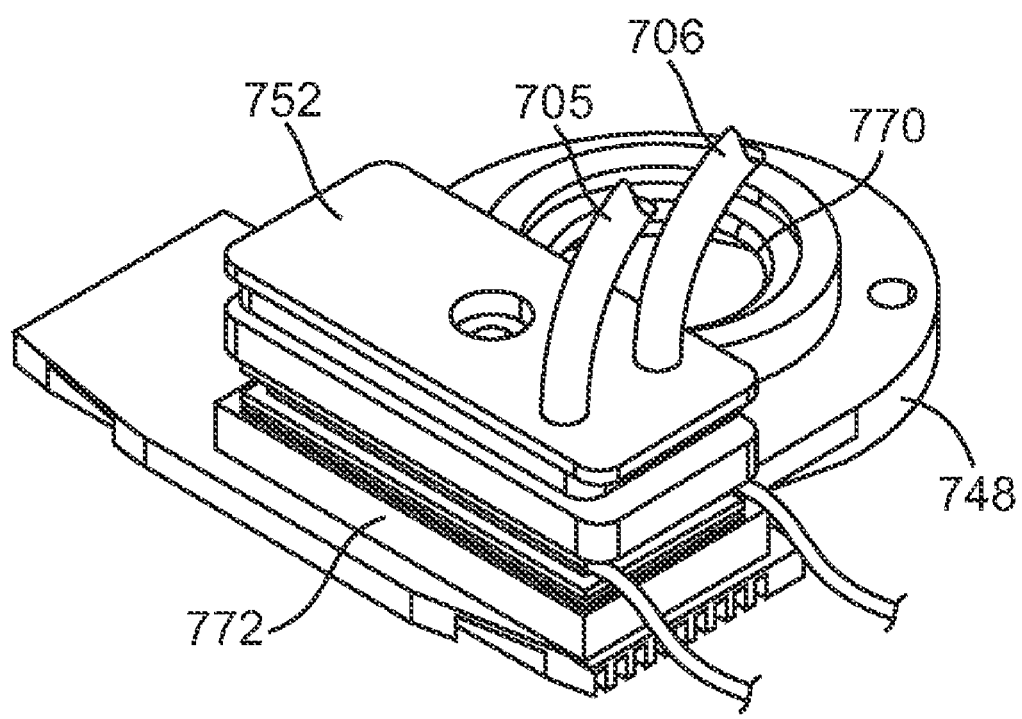
FIG. 25 is a perspective view of the combined thermoelectric device stack.

An illustration showing the fully assembled lower compartment heat transfer stack with heat transfer plate 748, riser 772 and thermal conductive material 780 is shown on the bottom of FIG. 24. The top of FIG. 24 shows the fully assembled upper compartment heat absorbing and liquid heat sink stack. FIG. 25 provides an illustration of the entire heat transfer stack using a TEC layer.

Figure 26:
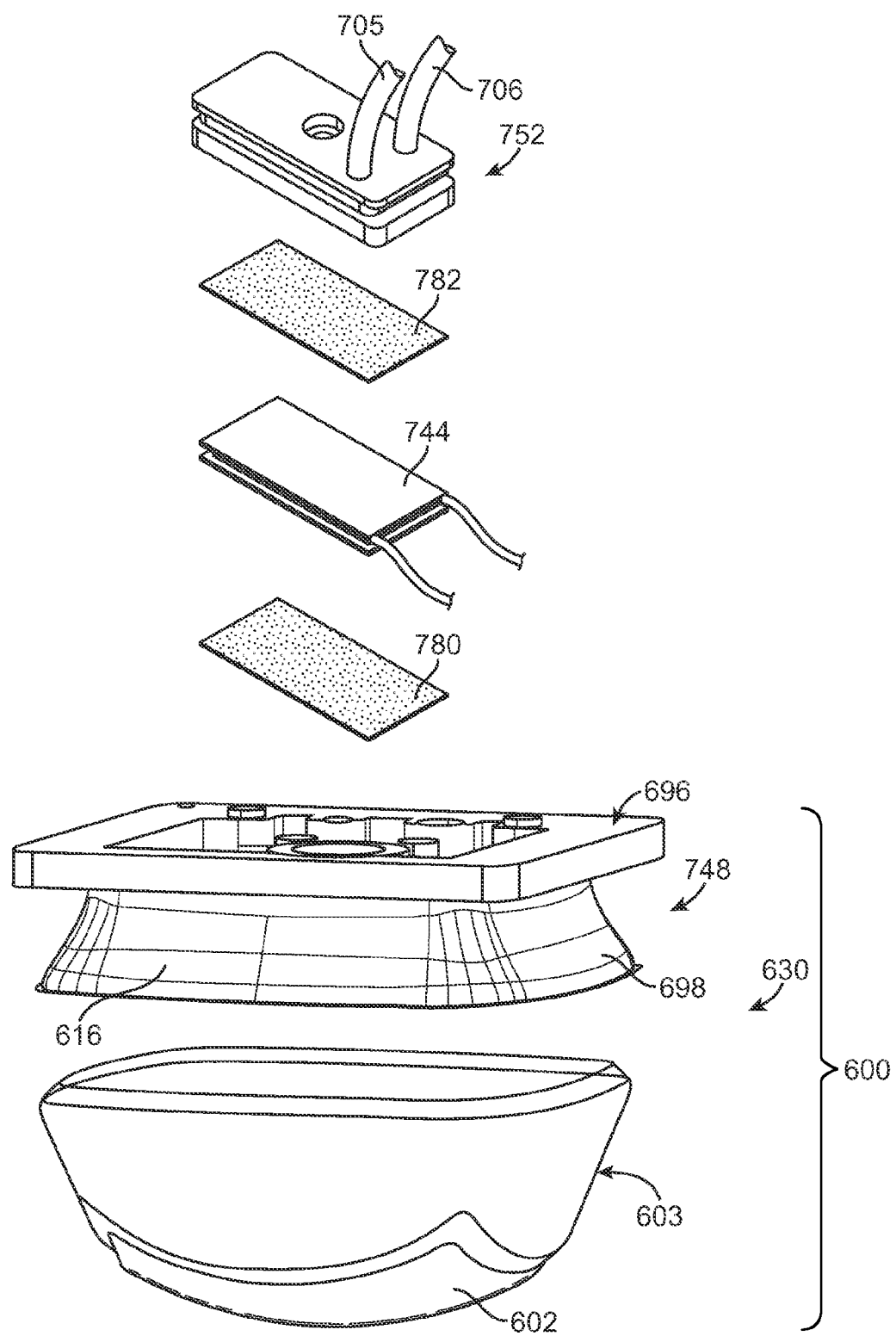
FIG. 26 is a perspective view of the exploded components of FIG. 21.

In an embodiment (FIG. 26), a heat transfer plate 748 extends across the top and part of the way down the sides of a lower compartment 600, forming an inverted bowl structure. In this embodiment, the heat transfer plate 748 is in contact with a lower-compartment fluid, such as degassed water (disposed within the lower compartment 600), across the top and part way down the sides of the lower compartment 600, thereby increasing the surface area through which heat can be transferred from the lower-compartment fluid into the heat transfer plate 748. The inverted bowl shaped heat transfer plate 748 may be a component of a removable/replaceable lower compartment 600. In the embodiment shown, the heat transfer plate 748 has a top surface 695 that is in contact with the lower-compartment fluid, and peripheral exterior plates 698 that are in contact with the lower-compartment fluid and form part of the exterior of the lower compartment 600. Top surface 695 and exterior plates 698 can be thermally conductive so that they may transfer heat to the surrounding air, or they can be externally insulated to avoid presenting a hot external surface. In an embodiment, the heat transfer plate 748 includes a top surface and partial side plates (not shown) disposed within the lower-compartment fluid. With partial side plates disposed within the lower-compartment fluid, the lower-compartment fluid is contacted with both surfaces of the partial side plates, which results in increased contact surface area between the heat transfer plate 748 and the lower-compartment fluid. This increased contact surface area may help to increase the heat transfer rate between the heat transfer plate 748 and the lower-compartment fluid. Partial side plates disposed within the lower-compartment fluid can include fluid openings and/or channels to facilitate the flow of the lower-compartment fluid over these submerged partial side plates. The cold side of a thermoelectric device 744 can be attached to the top of the heat transfer plate 748 by a heat transfer material 780 and a heat exchanger 752 can be attached to the hot side of the thermoelectric device 744 by a heat transfer material 782.

The lower-compartment fluid is "stirred" by acoustic pressure when the transducer (disposed within the lower compartment 600) is active. This "stirring" may be sufficient to constantly circulate within the cartridge, and thereby make contact with the heat exchanging components. The cooled lower-compartment fluid tends to sink into the lower portion of the lower compartment 600. The combination of the rising fluid heated by the transducer and the sinking fluid cooled by the heat transfer plate may result in a convective current that helps to enhance the rate of heat transfer between the transducer and the lower-compartment fluid and between the lower-compartment fluid and the heat transfer plate 748. This convection current may be further enhanced by the cooling of the lower-compartment fluid that occurs due to contact with the partial sidewalls of the heat transfer plate 748 on account of resulting peripheral sinking of the cooled lower-compartment fluid, which may complement the central rising of the lower-compartment fluid that is heated by a centrally located transducer. Additionally, the increased contact area between the heat transfer plate 748 and the lower-compartment fluid may also help to maintain the lower-compartment fluid at a lower equilibrium temperature.

Figure 27A:
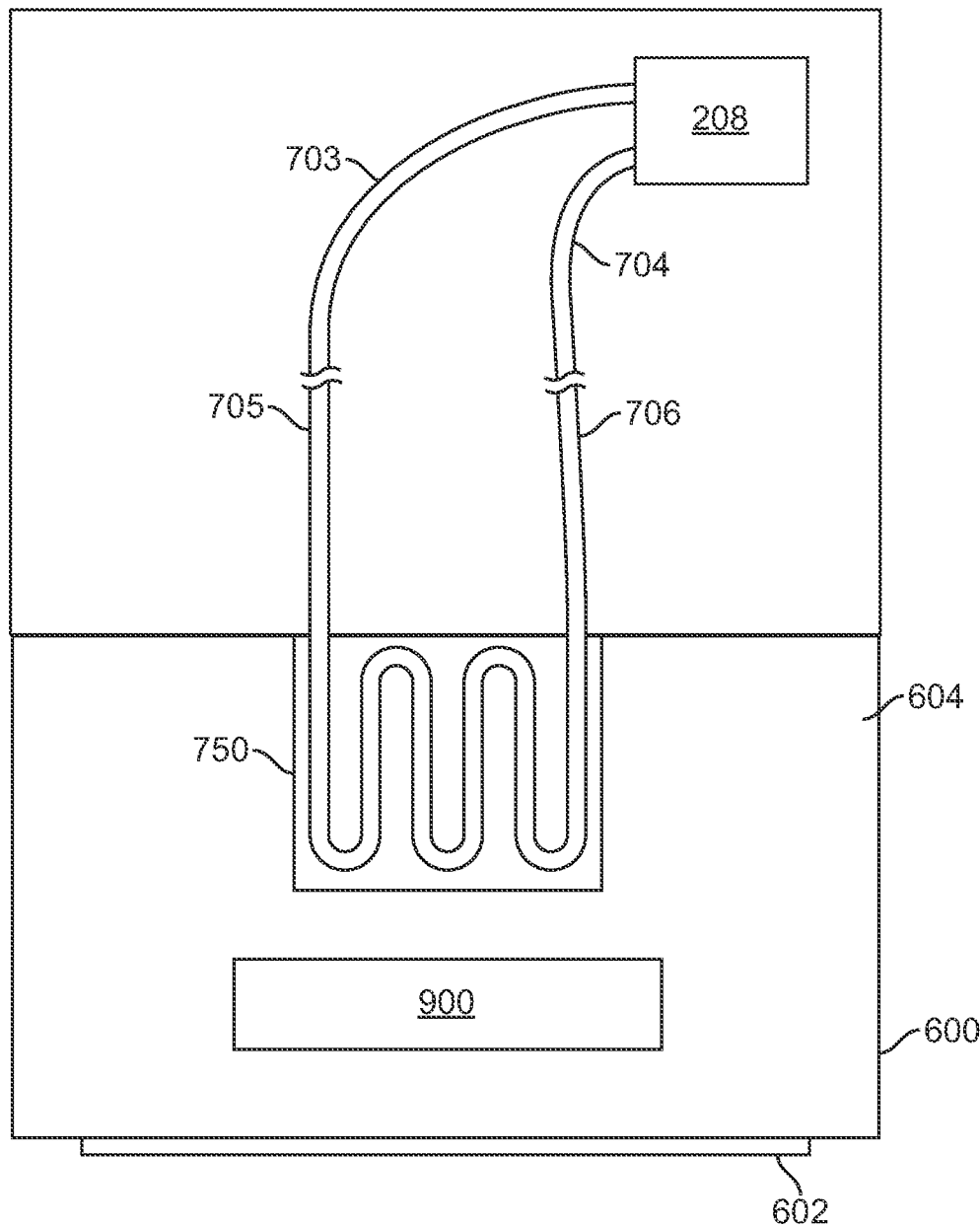
FIG. 27A is a schematic diagram representing components of a medical ultrasound system in accordance with another embodiment.

In an embodiment, the heat exchange process is done by circulating fluid from the fluid circulation system 208 into the cartridge 600 without compromising the integrity of the fluid sealed in the cartridge (FIG. 27A). A heat exchanger 750 can be positioned within the lower compartment 600 so as to absorb heat from a lower-compartment fluid 604. The first heat exchanger 750 is physically connected to a fluid circuit 706, 705 so temperature controlled fluid from the fluid control circuit 208 can take heat from the lower compartment fluid 604.

The first heat exchanger 750 is a fluid-circulating heat exchanger that is in fluid communication with the fluid circulation circuit 208 which contains a fluid chiller (not shown). In an embodiment, the first heat exchanger 750 are removed with, the lower compartment 600. A pump (not shown) can be used to circulate a fluid (e.g., water) between the first heat exchanger 750 and the chiller in the fluid circulation system 208.

Various configurations can be used for the first heat exchanger 750. The first heat exchanger 750 can be made from a thermally conductive metal (e.g., brass, copper, aluminum, etc.). The first heat exchanger 750 can also be shaped to maximize its surface area for more effective heat transfer. Such shapes are well known in the art for cooling, and include common shapes like baffles, coils or other repeating patterns.

The use of a first heat exchanger 750 can provide a number of advantages. For example, as described above, the first heat exchanger 750 can be located so as to facilitate circulation of the lower-compartment fluid, thereby helping to increase heat transfer. Additionally, the first heat exchanger 750 can be configured to increase and/or maximize the amount of surface area contact with the lower-compartment fluid, thereby helping to increase heat transfer.

The chiller can be located at a variety of locations within the base unit. In one aspect the chiller is located along with the rest of the fluid circulation system 208. If the chiller is not positioned in physical proximity to the fluid circulation system, it is still considered part of the system 208. Alternatively, the heat exchanger 750 may be positioned within the upper compartment 510 in a manner that allows for cooling in a circuit involving components only inside the therapy head 500. Such an embodiment may include a air cooled heat sink and fans to ensure air flow moves over the heat sink in a continuous manner.

Figure 28:
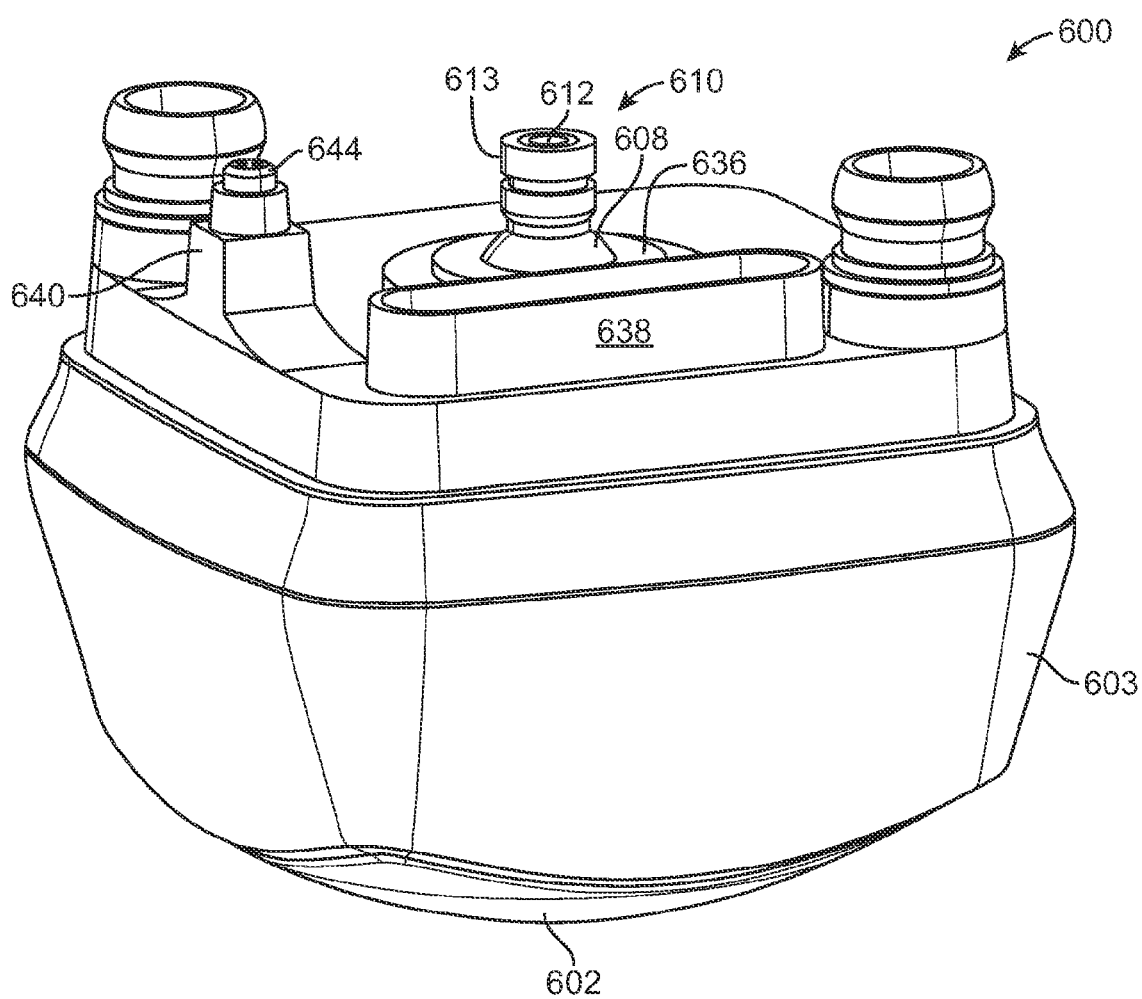
FIG. 28 is an isometric view of a transducer cartridge for a therapy head in accordance with an embodiment.
Figure 29A:
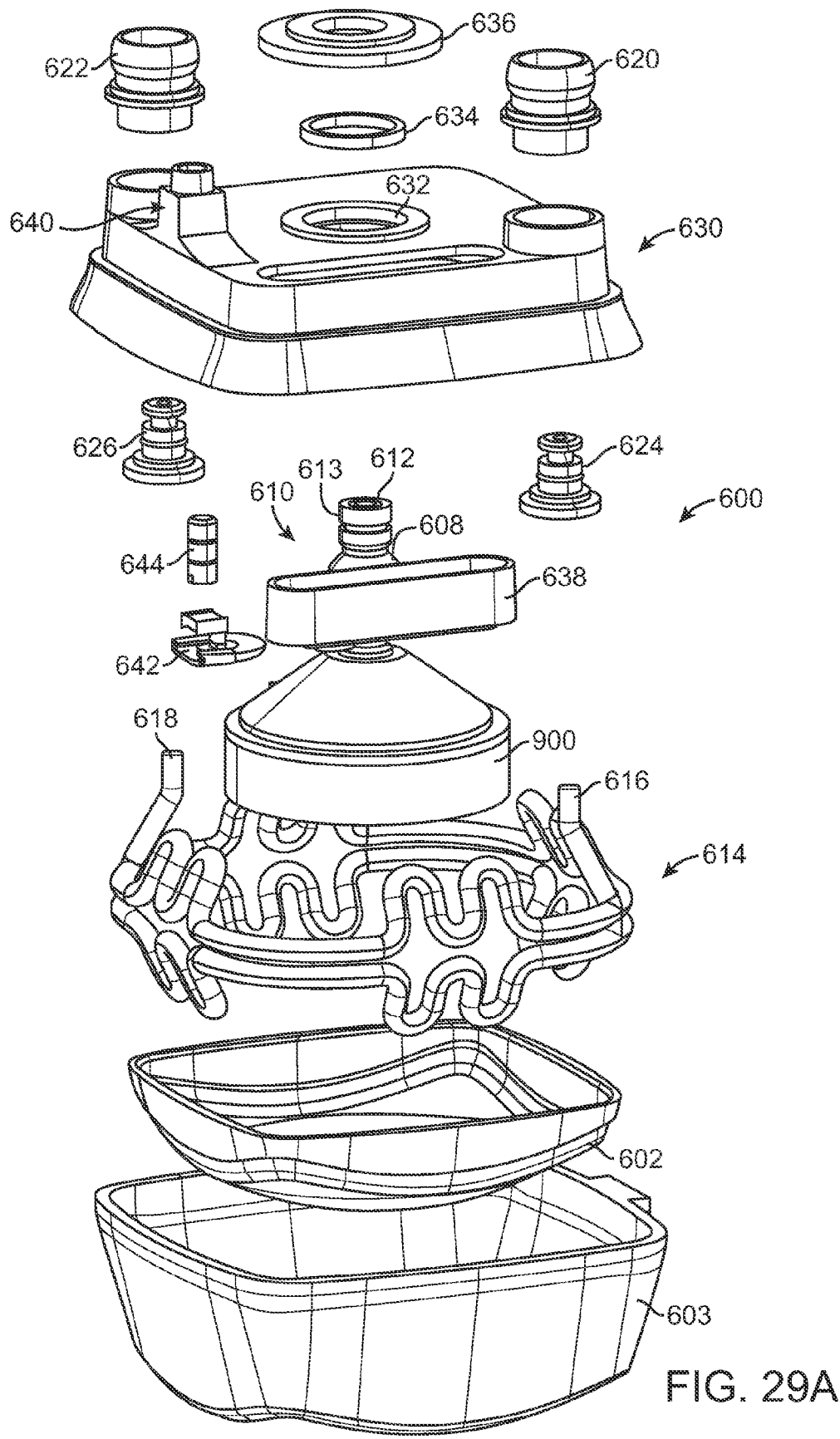
FIG. 29A is an exploded isometric view of the transducer cartridge of FIG. 28.

FIG. 28 shows a lower compartment 600 for a therapy head 500 (FIG. 14) in accordance with an alternative embodiment. The front or lower lens includes a window 602 (best shown in FIG. 29A) and sides 614.

Figure 30:
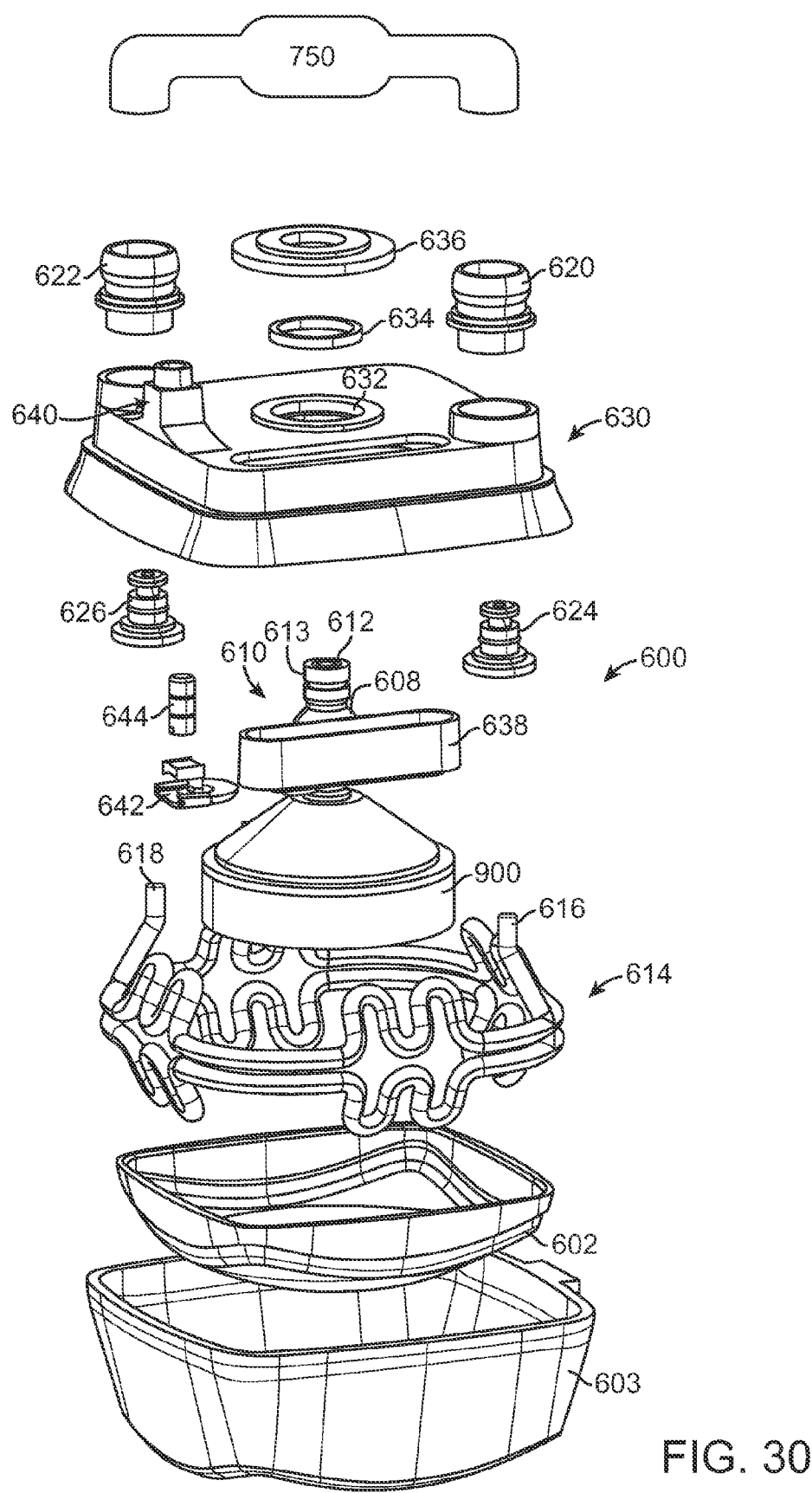
FIG. 30 is an exploded isometric view of the transducer cartridge having a thermal regulating device according to an embodiment.

FIG. 30 shows another embodiment where the fluid from the lower compartment is circulated into the upper compartment to a heat dissipating unit 750 which may include a heat sink with a plurality of heat radiating elements (similar to heat sinks used for computer central processor unit (CPU) chips). The heat sink may have a fan for directing air over the heat sink, or be encased in a fluid bath and cooled using fluid from the fluid circulation system 208. In one aspect the fluid used for cooling purposes is water.

The lower compartment 600 includes a transducer assembly 900 mounted therein and having a ball joint 608. The ball joint 608 is part of a pivot mechanism 610, such as is described in U.S. patent application Ser. No. 12/364,327, cited above. An opening 612 is located at the end of a shaft 613 for the transducer assembly 900.

The lower compartment 600 includes a heat exchanger 614 that extends along the inside of the side walls 603 for the lower compartment 600. The heat exchanger 614 is preferably formed of a highly thermally conductive material, such as copper. In the embodiment shown in the drawings, the heat exchanger 614 includes two sets of tubes that extend in a serpentine path around a perimeter of the lower compartment 600, inside the side walls 603. In an embodiment, the heat exchanger 614 is arranged so that it maximizes space on the outer portions of the lower compartment 600, but is outside the range of movement of the transducer assembly 600. In one aspect, the cooling system 700 is able to remove as many cooling watts from the cartridge 600 as necessary to maintain a desired operational temperature. If the transducer assembly is operating at high power and the transducer fluid 604 gets hot, the cooling watts to remove may be as high as 60 cooling watts. The desired temperature in the cartridge and the arrangement and type of TEC devices are balanced to ensure the cooling range is obtained. Although some instances may require high cooling watts, the system can operate by removing 15-20 cooling watts. In this case both chilled water and an appropriate flow rate may be used to maintain the cartridge temperature between 1-37° C. The temperature in the cartridge may be adjusted by the user. If desired, a TEC configuration can be used in combination with a fluid baffle configuration (not shown).

The heat exchanger 614 includes an inlet conduit 616 and an outlet conduit 618. The inlet and outlet conduits 616, 618 are mounted to ball seals 620, 622 and include valve fittings 624, 626. The seals 620, 622 are mounted in a top-plate 630 of the lower compartment 600. The top-plate 630 includes a central opening 632 through which the shaft 613 extends. An O-ring 634 is mounted in the opening and seats against the ball joint 608. The shaft 613 and the ball joint form a bearing member that fits in the central opening 632. The O-ring 634 permits the transducer assembly 900 to pivot as described in U.S. patent application Ser. No. 12/364,327, and prevents leaking of fluid out of the lower compartment 600 at the opening 632. A pivot top 636 fits over the O-ring 634. The ball joint 608 is captured between the pivot top 636 and the inner rim of the opening 632.

An electrical connector 638 is positioned on one side of the top plate 630. Wires may run from the electrical connector 638 to the transducer assembly 900. In addition, the electrical connector 638 may be configured to receive a wiring harness or other electrical connections that lead from the upper compartment. In an alternate embodiment, the wires for the transducer assembly 900 may extend along or down the shaft 613, or may be routed in another manner. The electrical connector 638 is preferably a quick disconnect connector and connects to a wiring harness or other connector (not shown) that is attached to the therapy head. When the wiring harness is attached to the connector 638, power, such as for the HIFU transducer drive or for other electronics in the transducer assembly, or communication signals may be supplied to the transducer assembly 900 via the wiring circuit.

Optionally, an alignment post 640 is positioned on one location of the top plate 630. The alignment post 640 permits an installer to properly align the lower compartment 600 with an upper compartment of the therapy head during installation. A bubble trap 642 may be provided for the capture of bubbles formed inside the lower compartment 600. In an embodiment, a micro valve 644 is attached to the bubble trap 642 to isolate bubbles away from the acoustic path of the transducer. The micro valve may be mounted in the alignment post 640.

The lower compartment 600 can be sealed, with the acoustic window 602, the sides 603, and the top-plate 630 forming an enclosure. A coupling fluid, such as water is captured in the enclosure, and the enclosure is permanently sealed. To prevent gas seepage, the portions forming the enclosure can be treated with a material to prevent gas leakage into the lower compartment. The enclosure interior may be treated with a sealant, or metallization layer, such as sputtered titanium. The heat exchanger 614 extends around the perimeter of this enclosure and provides optimal heat convection because of its serpentine or parallel path configuration, the large amount of surface area provided by extending the heat exchanger 614 around the perimeter, and by utilizing the dual conduit arrangement.

As with earlier embodiments, water is circulated through the heat exchanger 614 via the inlet conduit 616 and the outlet conduit 618. This water may be circulated, for example, to a base unit for cooling, or may be attached to a thermoelectric cooler for cooling, or may be routed through a conduit with inefficient heat retention that results in heat loss, as described in earlier embodiments.

Figure 29B:
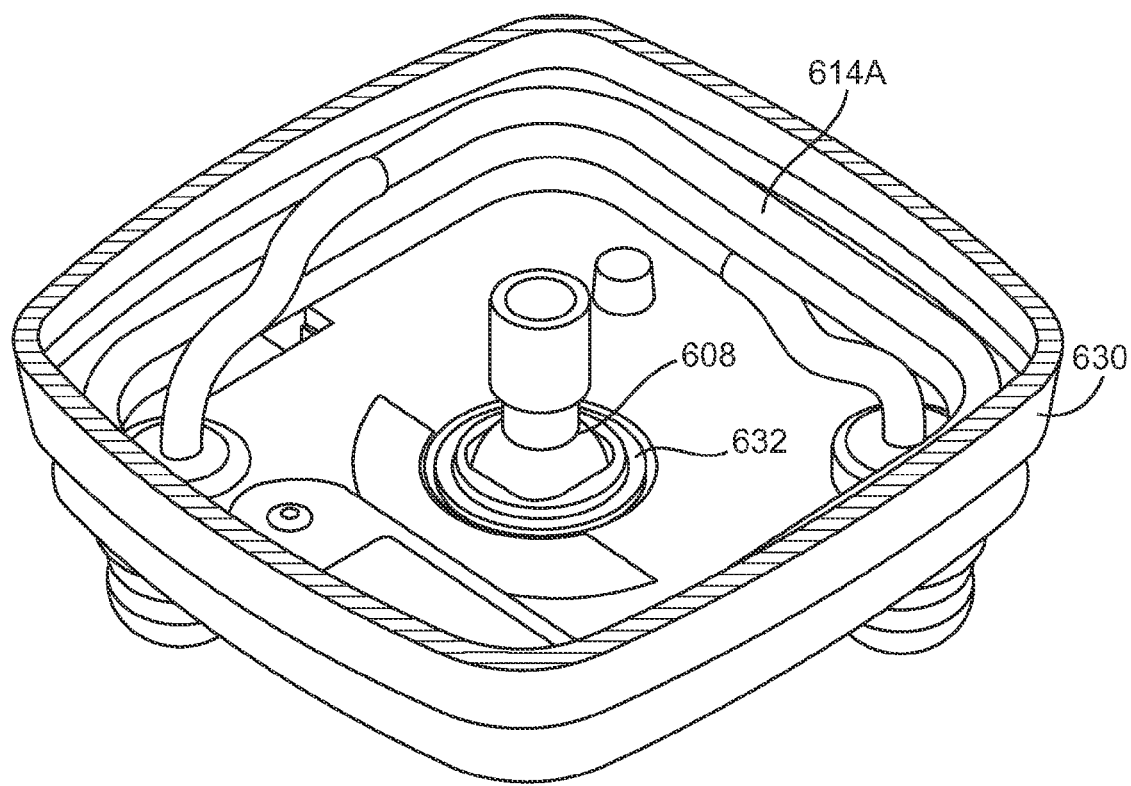
FIG. 29B is an isometric view of a bottom portion of a transducer cartridge displaying an alternative fluid conduit in accordance with an embodiment.

FIG. 29B is an bottom, isometric view of a top portion of a transducer cartridge displaying an alternative fluid conduit 614A in accordance with an embodiment. Instead of the serpentine shape that is used for the conduit 614, the conduit wraps around an inside portion of the top plate 630. Otherwise, the cartridge is the same in configuration. Many other shapes can be used for the conduit.

Figure 37:
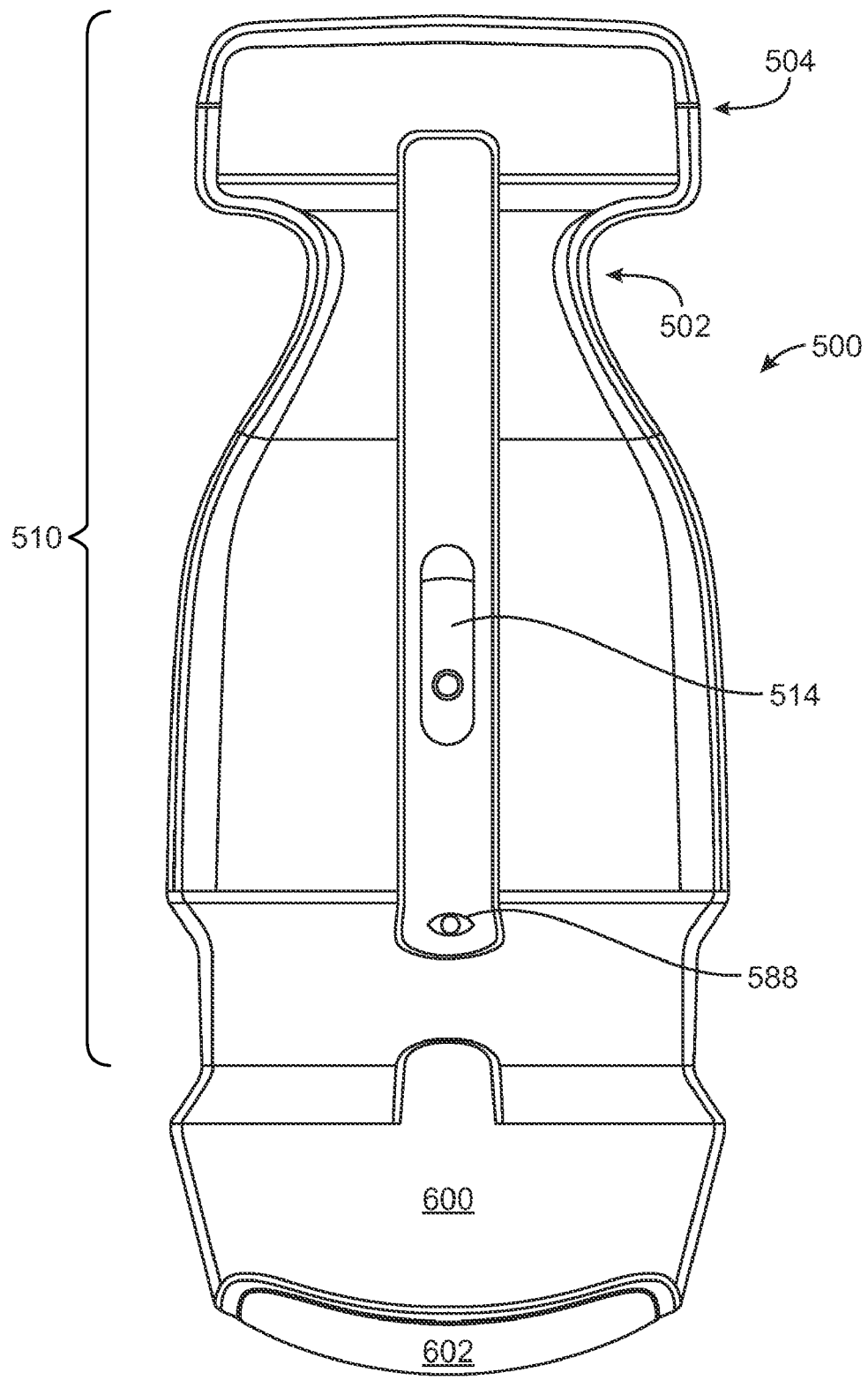
FIG. 37 shows a unigrip handle according to an embodiment.

The therapy head 500 includes a body, such as an upper compartment 510, including an indentation 502 for fitting a user's hand (FIG. 37). The upper compartment 510 may be attached to an arm and/or may include wires or conduits that lead to a base unit.

Figure 27B:
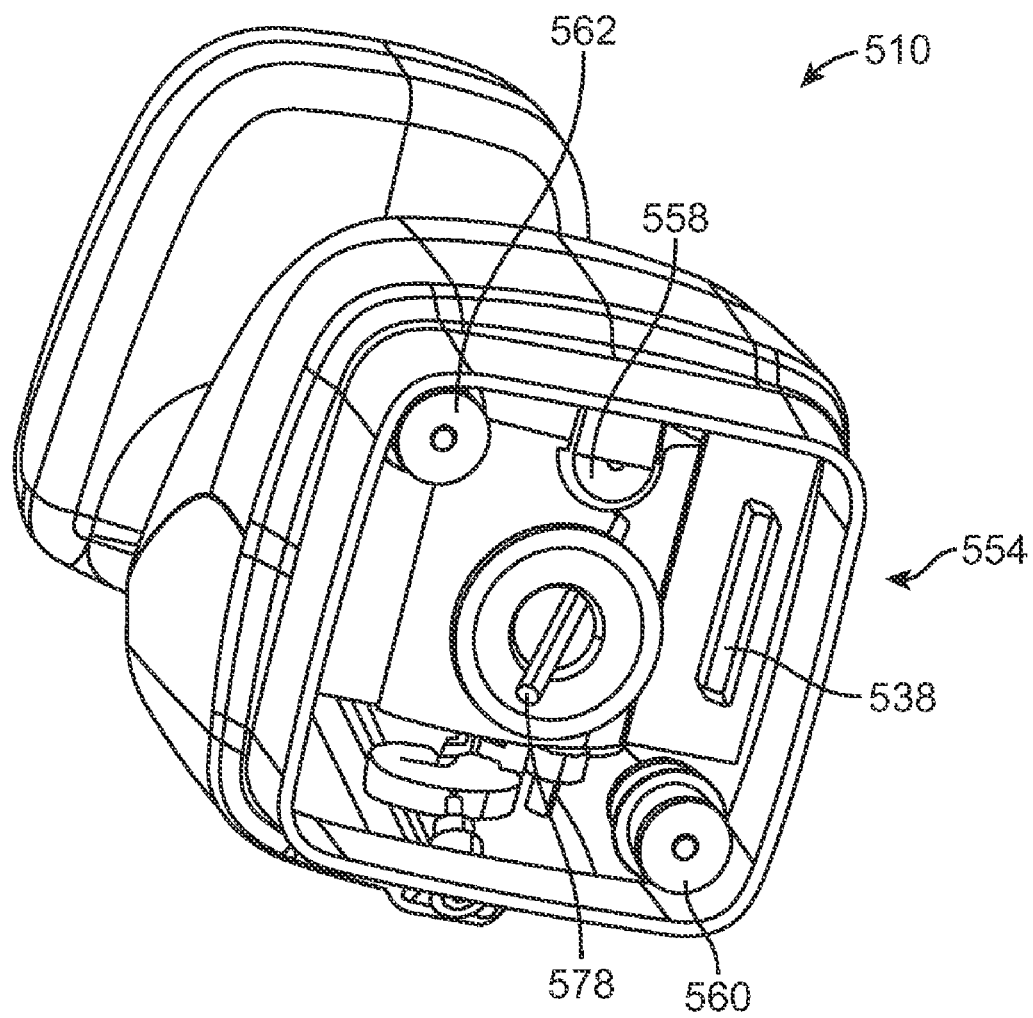
FIG. 27B is an isometric view of the bottom of the upper section in accordance with an embodiment.

FIG. 27B is a bottom perspective view of an exemplary upper compartment 510, with the lower compartment 600 removed. The upper compartment 510 includes a recess 554 for receiving the lower compartment 600. An electrical connector 538 is positioned in the recess 554.

An opening 558 is located in the recess 554. Two fluid connectors 560, 562 are positioned on opposite corners of the recess 554. These fluid connectors 560, 562 lead, for example, to a thermoelectric cooler, a chiller in the base unit, conduits that provide a cooling effect by being thermally inefficient, or some other cooling structure or configuration.

A control arm 578 for a driving mechanism, such as is described in U.S. patent application Ser. No. 12/364,327, is centrally positioned in the recess 554. The angle of the control arm 578 may be determined by the position of the driving mechanism.

To attach the lower compartment 600 to an upper compartment 510 of a therapy head, the wiring harness or recess 554 that is connected to the upper compartment is connected to the electrical connector 538. If a wiring harness is used, it is connected first. If a stationary connector, such as the recess 554, is used, then the connector is connected to the electrical connector 538 as the lower compartment 600 is attached to the upper compartment 510.

In any event, to attach the lower compartment 600 to the upper compartment 510, the top plate 630 of the lower compartment 600 is fitted into the recess 554 of the upper compartment. To allow this fitting, two fluid ports 620, 622 are aligned to the corresponding fluid ports 560, 562 in the upper compartment 510. An optional guide post 640 is aligned with the corresponding female structure in the upper compartment, for example the opening 558. The fluid ports 620, 622 may use seals to align with and connect to the fluid connectors 560, 562 on the upper compartment 510. During alignment, the opening 612 on the shaft 613 is aligned with the control arm 578 on the bottom of the upper compartment 510. The control arm 578 may have to be centered for proper alignment. To this end, a "home" operation may be provided for centering the control arm 578. This control arm 578 is connected to the actuator assembly in the upper compartment, and the transducer assembly 900 in the lower compartment (when the upper and lower compartments are properly combined) such that, once installed, the movement of the control arm causes the desired movement of the transducer assembly 900.

After alignment, lower compartment 600 is pressed into the upper compartment 510. The two profiles of the lower compartment top plate 630 and the upper compartment recess 554 fit together. The electrical connector 538 seats onto the corresponding lower compartment electrical connector 638. The mechanical linkage 578 engages the transducer arm assembly 612. If fluid connectors are used, the fluid lines 560, 562 connect to the seals 620, 622. Appropriate valves are provided to open or close the fluid connectors. The nub 578 fits into the opening 612 of the shaft 613. The therapy head 500 is now ready for operation.

Once connected, cooling water may flow into and out of the heat exchanger 614 via the fluid connectors 560, 562. The direction of the transducer assembly 900 may be changed by using the drive mechanism, via the attachment of the nub 578 and the opening 612. The transducer assembly 900 may be provided power via the connectors 538, 638.

Disconnecting the lower compartment 600 is done in reverse order. That is, the lower compartment 600 is disconnected from the upper compartment. If desired, a latch or other lock mechanism may be provided for maintaining connection of the lower compartment 600 to the upper compartment 510. As an alternative, the connection of the various components of the lower compartment 600 to the appropriate components of the upper compartment, such as the seals 620, 622 to the fluid connectors 560, 562, may provide a sufficient holding force to keep the lower compartment 600 in place. Connecting and disconnecting the lower compartment from the upper compartment may be facilitated by the use of a tool.

In accordance with an embodiment, a mechanical compensator may be provided for the lower compartment 600 as shown in FIGS. 32A-B, 33A-B. This mechanical compensator can be configured to offset pressure changes in the environment in which the therapy head is operated, for example, changes in pressure due to altitude, and to accommodate pressure changes in shipping the cartridge and/or accommodate any water loss over time.

The mechanical compensator may take a variety of forms. Any device that adjusts for changes in pressure and maintains the desired degas state of the internal fluid may be used. In an embodiment, a passive compensator has a body 680 containing closed piston face 686 and a spring 684 (FIG. 32A). The closed piston face 686 has an opening 688 exposed to the fluid filled interior of the lower compartment/transducer cartridge 600. The cartridge ships with the full water volume and as the internal water volume expands (due to internal temperature increase or external pressure decrease) the piston face 686 deflects backwards against the spring 684 allowing the internal volume to expand (FIG. 32B). Once the temperature or pressure returns to normal, the spring force pushes the piston forward returning the volume back to initial equilibrium. The back of the piston is vented to the atmosphere. Other examples of passive compensators include metal bellows, an air filled bladder (having the air sealed from the fluid), a compressible material like foam or soft durometer rubber component, or an expandable outer housing.

Figures 33A, 33B:
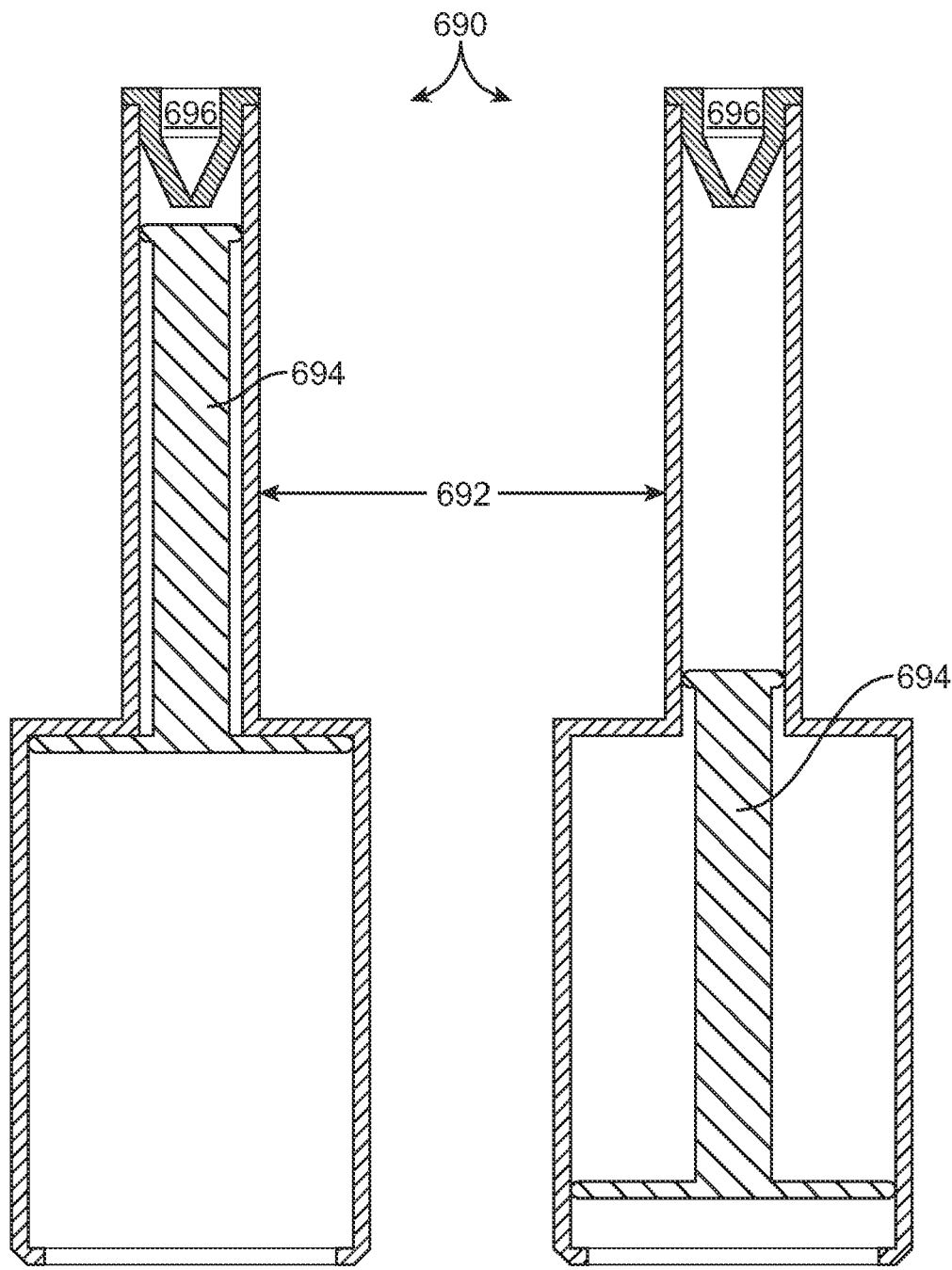
FIGS. 33A-B provide a pressure relief mechanism in accordance with an embodiment for the cartridge.

In an embodiment, and active compensator 690 may be used. An active compensator could tap off of the cooling water in the heat exchanger to operate the compensator. The compensator would consist of a housing 692, a piston 694 and a one way valve 696. The cartridge ships under-filled by the volume of the compensator with the internal piston in the retracted position (FIG. 33A). Once the cartridge is installed and the system turned on, the pressure of the cooling water would drive the piston outward to force the volume increase. The piston could be sized to reduce the pressure so that the piston extension would stop when the pressures equalized (Example: Cooling water at 20 PSI and internal pressure desired to be 2 PSI then the piston area could be reduced 10:1)(FIG. 33B). The one way valve would allow the piston to expand but not contract thereby maintaining the pressure in the cartridge. Other embodiments of an active compensator include a flexible bladder, a mechanical piston or a user applied syringe. Additional embodiments are readily available and well understood by those skilled in the art.

In an embodiment, the inner surfaces of the cartridge 604 (FIG. 31) may include a thin inner coating 601 to prevent gas permeability. For example, if the sides 604, window 602 and top plate 630 are made of plastic, a titanium base layer may be provided to prevent atmospheric gas from entering the chamber and dissolving in the fluid inside. This layer may be attached in a suitable manner, but in an embodiment is titanium that is sputtered between approximately 500 to 1500 angstroms thick onto the inside surfaces of the cartridge. Alternatively the metallization layer may be copper and nickel, or any other material suitable to fill pores in the plastic chamber and prevent gas from entering the chamber. Any material may be used for this purpose that satisfies the requirements of being insolvent in the liquid (the material will not enter into solution in any appreciable amount) and the material reduces gas permeability through the chamber material to an acceptable level. In one aspect, the dissolved oxygen (DO) content is kept below about 10 ppm. In another aspect the DO content is below about 8 ppm.

In an embodiment, the coating reduces the gas permeability of the plastics to prevent the internal fluid volume from absorbing gasses. This is done to maintain the Dissolved Oxygen level in the sealed water volume below a certain level. Metallization sputtered coatings ranging between 500 and 1500 angstroms work well for this purpose. Desirably the insides of the plastic housings are coated with 80 microinches of copper followed by 10 microinches of nickel. The testing shows that the plating absolutely reduces the gas permeability of the plastics. The thickness is not as critical assuming that the atomic radii of the coating metal are smaller than the pores in the plastic. It is believed that the atoms of metal cover and fill the pores.

A temperature sensor may be provided to sense the temperature of the water in the lower compartment 600. If desired, operation may alter according to a sensed temperature, such as by shutting down operation, slowing operation, or increasing cooling.

Figure 31:
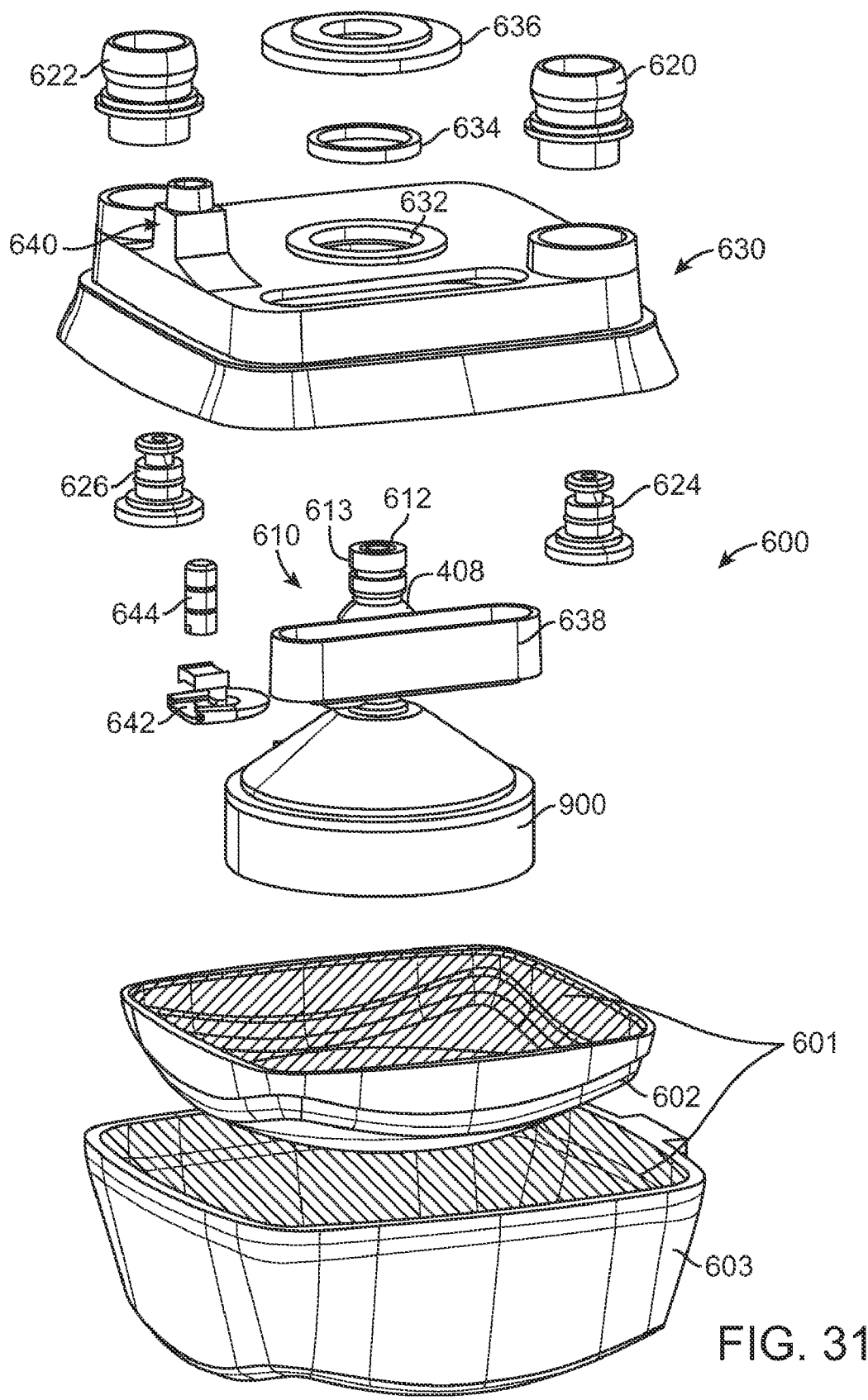
FIG. 31 is an exploded isometric view of the transducer cartridge according to an embodiment.

In an embodiment, the cartridge may be cooled directly by the fluidics of the main system (FIG. 31). The baffles are removed and the fluid from the fluidics system flows directly into the cartridge through an inlet port bal seal 620 and out through the outlet port seal 622. Fluid from the fluid circulation system floods the cartridge after it is connected to the upper compartment 510 and bathes the transducer assembly 900 in fluid. Fluid flow velocity is adjusted to provide the desired cooling time to bring the cartridge to the desired internal temperature. It may also be used to provide additional cooling to reduce skin sensitivity of a patient being treated (like placing a cold pack on the skin). In this embodiment the fluid circulation system includes a degas unit to remove gas displaced by fluid when the cartridge is initially flooded with fluid. In an embodiment the fluid is water which is filtered and degassed. A pressure adjustment device or pressure control system may be used to keep the cartridge under pressure if the window is flexible, or some other component of the cartridge may change that may effect the internal pressure.

Therapy heads described herein provide a number of benefits. First, a lower compartment can be a self-contained unit, without water connectors or water conduits. Such a lower compartment, or transducer cartridge, does not need to be drained when the lower compartment is replaced. Thus, unlike prior art systems, water is not circulated from the base unit to the lower compartment, and a particular pressure of water into a lower compartment does not have to be maintained.

Additionally, in some embodiments, the lower compartment and the transducer are integrated into an easily replaceable unit that does not require the removal of wires or water or other fluid conduits. By simply attaching a lower compartment to an upper compartment, a heat transfer plate or heat exchanger is attached to a thermoelectric device and the lower compartment is prepared for use.

The transducer assembly 900 used in the lower compartment or cartridge 600 is now described. In an embodiment the transducer assembly has a cylindrical shell having a transducer mounted in one end of the cylindrical shell, and a mechanical arm and electrical connector mounted in the opposite end of the cylindrical shell. The shell contains a PCB dedicated to run the transducer, and handle any data feedback flow from the transducer to any other part of the system 100. The transducer may be a single element mechanically focused ultrasound transducer as previously described in co-pending U.S. patent application Ser. No. 12/051,073 entitled "Interchangeable High Intensity Focused Ultrasound Transducer" which is commonly assigned. Alternatively the transducer may be an annular array, linear array or phased array transducer with the capability of delivering therapeutic ultrasound.

In another aspect the interface cable 116 has a coaxial cable for powering, controlling and receiving signals from the individual elements of an array transducer. Fewer channels in the cable 116 may be used if a transducer array has more than one element tied to a single control line, allowing all tied elements to be excited simultaneously from the same command signal.

Figure 36A:
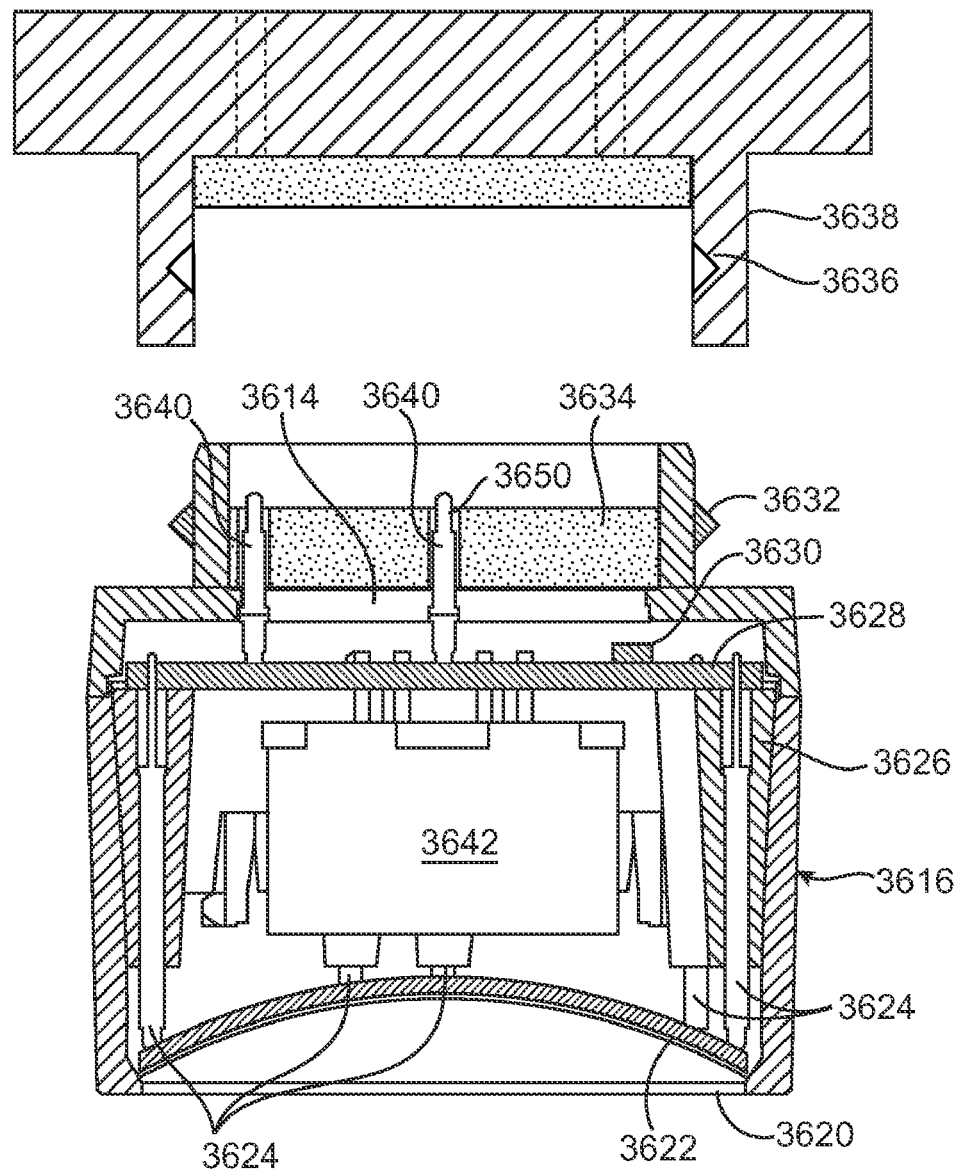
FIG. 36A shows a tall stack transducer assembly.

A transducer assembly for use in the systems described herein may allow for some variation. A tall stack and a short stack transducer assembly are provided for. The tall stack transducer possesses the features for interchanging the transducer in the therapy head. The short stack transducer is provided for embodiments that may utilize a transducer cartridge. It is possible to use the tall stack transducer in a transducer cartridge, however the cartridge becomes elongated, and the mass of the transducer on the end of the pivot arm may be problematic as the transducer is moved in a three dimensioned pivot arc. First described are the tall stack transducer assemblies. In an embodiment, a transducer for use with the therapy head is now described (FIG. 36A). The transducer can be similar to one previously described in co-pending U.S. patent application Ser. No. 12/051,073 entitled Interchangeable High Intensity Focused Ultrasound Transducer. In an embodiment, there is a housing 3616 having a substantially cylindrical shape. The housing 3616 has a neck down region located near an isolation layer 3634, and a larger diameter near a mechanically focused transducer 3622. The transducer side 3620 is open, or has a window so ultrasound energy may be broadcast out of the housing 3616 unimpeded. The transducer 3622 is secured near the open end 3620, and connects to an interface 3628 via a set of connection pins 3624. The connection pins 3624 are held in place with a concentric liner 3626 inside the housing 3616. The interface 3628 may be a set of connecting wires as previously described, or may include a circuit, PCB, PC(B)A or other hardware component. The interface may also have additional electronics, such as a transformer 3642 for tuning the transducer 3622, a data chip or integrated circuit (IC) 3630 to help identify the interchangeable transducer 3610 to the medical system. Additional components are described below.

Behind the transducer 3622, there is a seal 3614 for preventing water or atmosphere from entering the internal compartment of the transducer assembly 3610. Working in conjunction with the seal 3614 is an isolation layer 3634 for reducing pin corrosion and/or cross talk between the external electrical connectors 3640. Note the transducer side 3620 is also sealed against the outside environment. While the transducer side 3620 may be sealed with the transducer 3622 itself and various compounds which can be used to prevent leakage, the seal 3614 has one or more apertures 3650 for the protrusion of the external electrical connectors 3640. The apertures 3650 are typically large enough to allow the passage of the electrical connectors 3640. The apertures may rely on an interference fit to prevent seepage of fluid between the apertures and the pins, or the use of a sealing agent, or both. The apertures 3650 may be sealed once the external electrical connectors 3640 are placed using solder, epoxy, resin, adhesive or other suitable sealing agents. A mechanical connector 3632 is located on the housing and designed for engagement of a corresponding connection on the medical system socket 3638. The mechanical receiving element 3636 and mechanical connector 3632 form a transducer-system connection. This connection is typically one having high endurance. Repetitive reliability is desirable, but not required for the transducer connector 3632, as it is not envisioned that any one particular transducer will be removed and inserted a large number of times.

The design of the transducer connector 3632 and the system side connection (receptor) 3636 allow for individual transducers to be interchanged with the medical system on demand. This allows a single medical system to have a great deal of variety in its operational scope. Each new transducer can provide added capability as well as replacement for worn or out dated parts. In one aspect the mating of the transducer 3610 to the system can be accomplished with a low insertion force connector 3632 and receptor 3636 combination. Though the insertion force is low, the connection is robust so the transducer 3610 will be stable while mounted in socket 3638. Electrical communication between the system and the transducer is maintained regardless of how the socket might be moved. The socket is attached to the linkage allowing for the transducer to move as needed by the motor assembly.

Figure 36B:
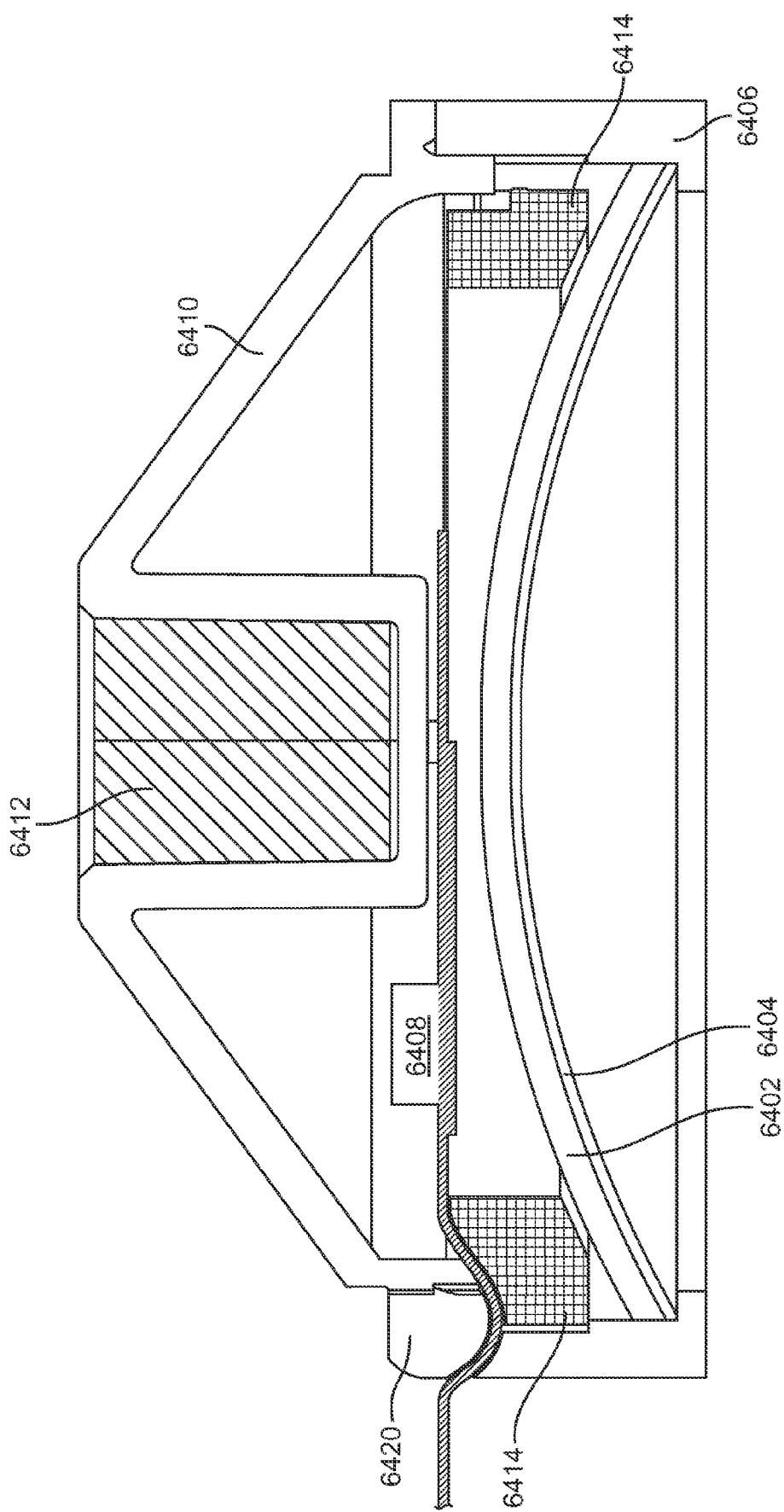
FIGS. 36B-D provide views of a short stack transducer assembly, according to embodiments.

In another embodiment, a transducer assembly having a shortened height may be used in a transducer cartridge (a short stack transducer assembly). In an aspect of the embodiment, the transducer eliminates the cylindrical housing. Instead, the transducer may be placed into a short housing dimensioned just about the size of the transducer itself (FIG. 36B). The transducer 6402 has a matching layer 6404 and the transducer is set inside a lower housing 6406. The lower housing 6406 has an inner ring shaped cut out dimensioned to match the circumference of the transducer 6402. The transducer may be secured into the lower housing using an adhesive compound, or may be welded into place. Alternatively, the transducer may be press fit into the lower housing by a donut shaped support 6414 for supporting electrical contacts. A flex circuit 6408 is laid on top of the support 6414 and upper casing 6410 is used to seal the assembly together. The upper casing 6410 has a raised roof line to make room for a recess 6412 used to receive a guide arm from the ball joint. The arm may be fitted into the recess using an interference fit, glue or other adhesive to secure the bonding between the arm component and the upper casing. A locking piece 6420 is used to help secure the upper casing 6410, the flex circuit 6408 and the lower housing 6406 together.

Figure 36C:
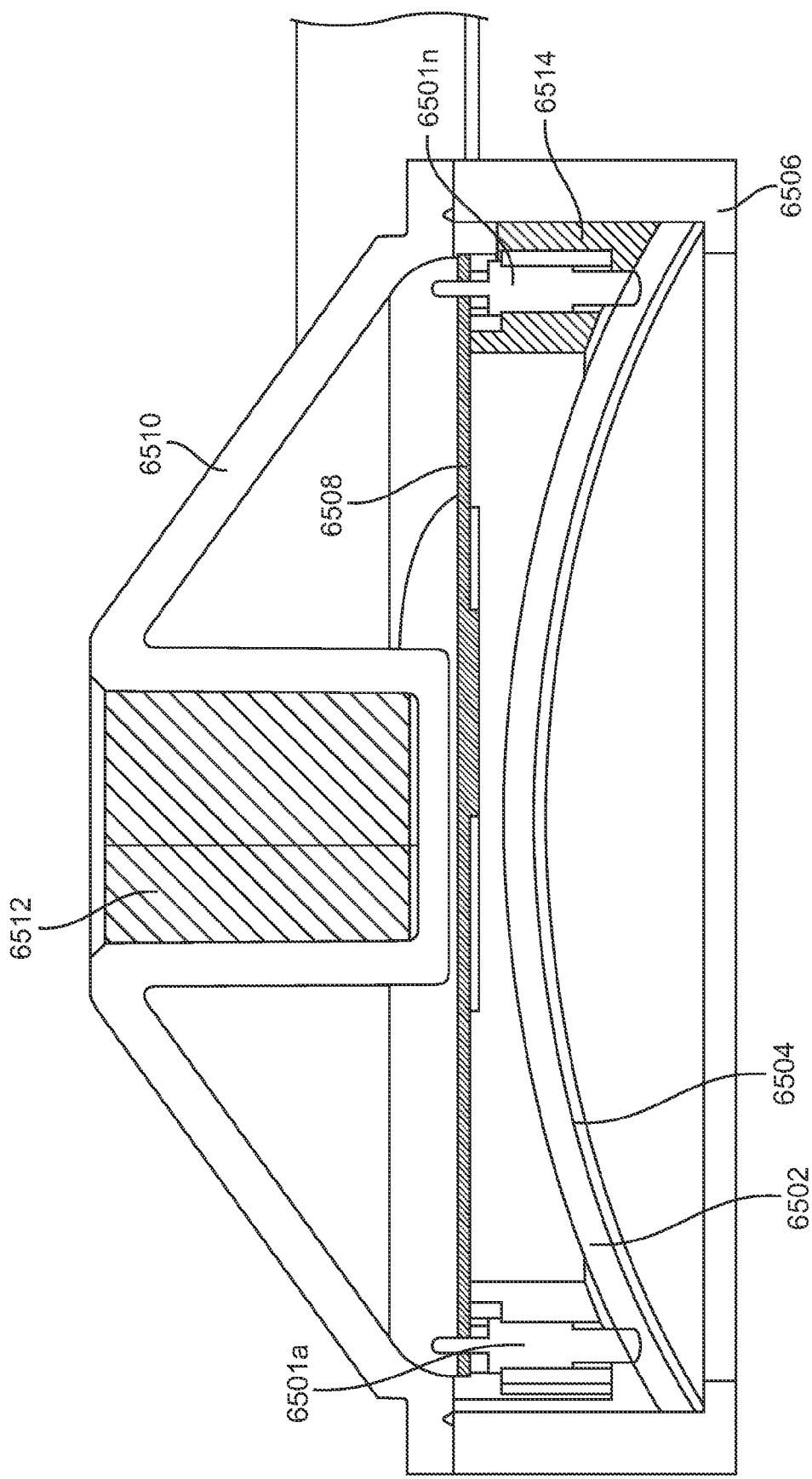

In an embodiment, the flex circuit 6508 connects to the transducer 6502 using a set of spring loaded electrical pins $6501_{a-n}$ (FIG. 36C). The spring loaded electrical pins (pogo pins) are seated in the donut shaped support 6514, and spring tension of the pins provides pressure on the transducer 6502 to keep the transducer properly seated against the lower section 6506. The housing also has an upper housing 6510 with a recess 6512 for engaging a moving post. The electrical pins 6501a-n connect to electrical lands or contacts on the transducer. A matching layer 6504 is provided on the transducer as well.

Figure 36D:
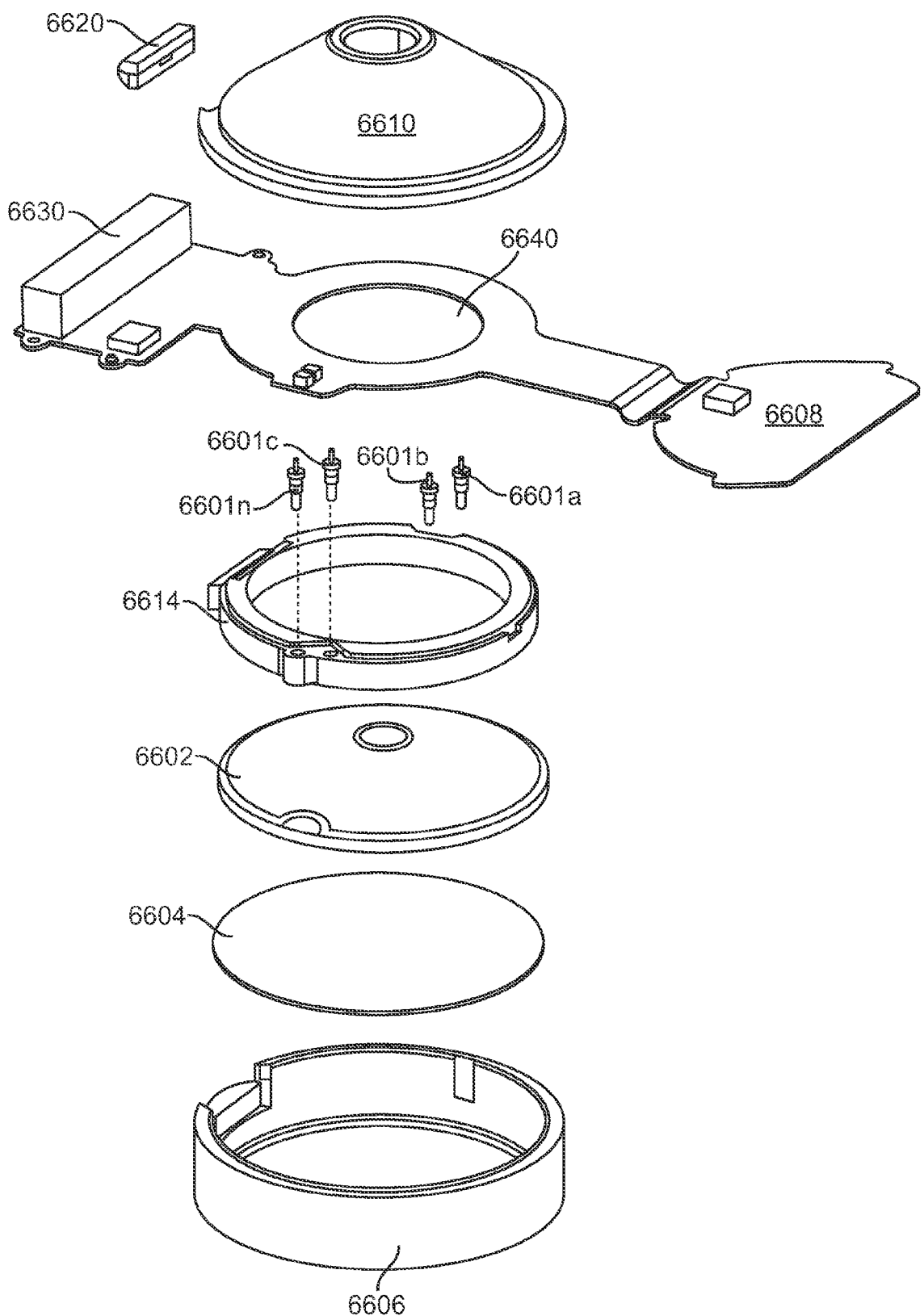

An assembly illustration of the short transducer stack is shown in FIG. 36D. The lower section 6606 has a lip on the inner circumference so the matching layer 6604, bonded to the transducer 6602, can sit on the lip. A donut shaped support 6614 sits on top of the transducer 6602 and matching layer 6604 assembly and provides physical support for a set of electrical contact pins $6601_{a-n}$, which may be spring loaded pins. The electrical contact pins are in electrical communication with the flex circuit 6608 and the transducer 6602. An upper housing 6610 sits on top of the flex circuit, donut shaped support and lower housing 6606. The upper section 6610 may be bonded to the lower section. A seal or locking piece 6620 may be used to secure the flex circuit 6608 into the assembly. The flex circuit has an electrical connector 6630 that provides electrical connection and communication between the short transducer stack and the therapy head. The electrical connector 6630 may be shaped to fit within the electrical port 638 (FIGS. 29-31A). The circular aperture 6640 of the flex circuit may be positioned to fit over the ball joint 610 and wrap around to connect to the transducer. The short stack transducer may be used in place of the transducer assembly 900.

In another embodiment, a hybrid stack transducer may be used. The hybrid stack transducer combines the space saving features of the short stack transducer assembly and the socket style interchange between the system (treatment head) and transducer assembly used in the tall stack transducer assembly. This hybrid stack allows a therapy head to use a smaller volume of coupling fluid since the size of the transducer chamber defined by a removable cap, and the lower end of the treatment head, is reduced.

Transducers used in the various transducer assemblies described herein are typically high intensity focused ultrasound transducers. Focusing may be achieved by using mechanically focused (curved) transducers, or electronically steered/focused transducers such as annular arrays, linear arrays and 2D arrays.

The transducer housing may have a metallization layer on the inside of the cylindrical housing to prevent gas from seeping from the inside of the transducer assembly into the degassed fluid used in the cartridge. Furthermore the transducer housing has a reduced axial length to allow for greater mobility within the cartridge. Shortening of the stack of components over the prior art is accomplished by reducing the housing, tightening the space between the components, and may include reducing the axial height of components such as the tuning transformer or the electrical connectors. The housing is dimensioned to allow the transducer to move and pivot within the cartridge as desired without getting tangled up in the cooling system or the side walls. Alternatively an array transducer may be used in the transducer assembly.

Optionally the treatment head 500 as described herein in various embodiments, may also include a fluid spraying system for distributing a coupling fluid from within the system, onto the body of a patient, prior to treatment by the treatment head. A system possessing the spraying device is now shown in FIGS. 37-44. In one aspect the fluid used in the fluid circulation system 208 is also used as the coupling fluid on the patient body. The medical ultrasound system 100 has a fluidics system 208 including at least one pump and filter set 220, where fluid is pumped into the treatment head 500. The fluid may be used for any of the functions and purposes described herein in addition to being used as a coupling solution for a sprayer. A sprayer 588 (FIG. 37) is positioned within the upper compartment 510 of the treatment head 500 and is linked to a manual trigger 514. A user may aim the sprayer 588 at a desired portion of the patient and spray coupling fluid on to the patient by depressing the trigger 514. Since the fluid in the fluidics system is under pressure, the fluid can spray out and cover the desired area at which the user aims at.

In one embodiment the fluid consists essentially of water. The water in the fluidics system is desirably about 99.0% or better pure, and typically free of large particulate matter. The filter(s) in the pump and filter set 220 should remove particulate mass and any impurities in the water down to a predetermined diameter, such as about 0.2 um (microns). Smaller or larger mesh size filters may be used depending on the type of particulate matter in the water, e.g., a biocide may be used to prevent bacterial growth enabling a more porous filter, while a lack of any biocide would call for a small pore filter to capture bacteria. The fluid typically does not contain surfactants. The general use of water as a coupling solutions, as described in co-pending U.S. patent application Ser. No. 11/373419 entitled Method and Apparatus for Coupling a HIFU Transducer to a Skin Surface shows no surfactant is generally needed. In one aspect, the water is degassed, filtered, gel-free, and substantially pure.

The exterior of the ultrasound head 500 can be an ergonomic form factor that is easily handled by an operator. An example of one embodiment is shown in FIG. 37, but the treatment head may take many other forms. The treatment head 500 may have cables extending from it and going to the base unit 130.

In use, the ultrasound head 500 is manually placed into contact with a patient's skin. Ultrasound treatments are administered through the ultrasound head 500.

As shown in FIG. 37, an ultrasound head 500 can include a lower compartment 600, or cartridge, and an upper compartment 510. The upper compartment 510 is desirably dry and houses wires, cables, a motor assembly, and/or other features for a transducer, which is mounted in the lower compartment 600. The lower compartment 600 preferably contains a fluid, such as degassed water, used to couple ultrasound energy from the transducer to and through a flexible window 602 located near the bottom of the lower compartment.

In operation, a technician can roll the medical ultrasound system 100 adjacent to a patient. The technician can grasp and move the treatment head 500, wielding it freely except for the cable 116 connecting the treatment head 500 to the base 130. The ultrasound head 500 is aligned so that the window 602 is in contact with the patient. The display/UI 102 may be operated to generate an appropriate treatment or diagnostic test. During use, the transducer mounted in the lower compartment 600 generates ultrasound energy, which may be used, for example, for the destruction of adipose tissue, as described in U.S. Published Application No. 2006/0122509.

The transducer assembly 900 mounted in the lower compartment 600 may take various different forms, and, in an embodiment, is movable so that it may focus toward various different locations of the window 602 as previously described.

As described in the background section of this document, as well as in the above incorporated U.S. patent application Ser. No. 11/373,419 entitled "Methods and Apparatus For Coupling a HIFU Transducer To a Skin Surface," a coupling agent or fluid (e.g., water) can be used between the ultrasound head and the skin to reduce or prevent the attenuation or reflection of ultrasound energy emitted by the ultrasound head's transducer. To this end, to enhance transmissibility between the cartridge 600 and a user's body, a coupling fluid can be applied to the skin surface to moisten the skin in a substantially even manner. The transmission window 602 can then be placed on the skin and pressed into the skin surface slightly to provide contact across the face of the flexible window with the skin surface.

Figure 38:
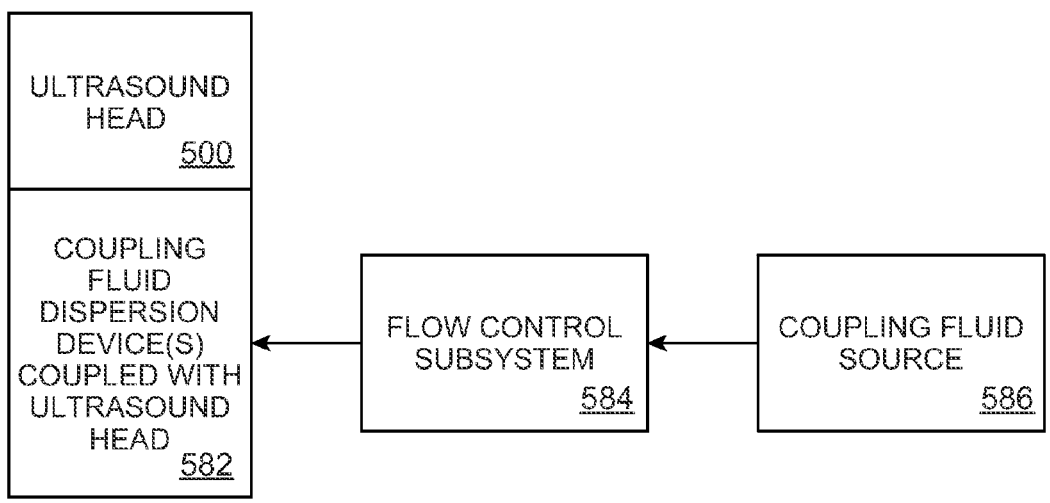
FIG. 38 is a block diagram of a coupling fluid system, in accordance with an embodiment.

FIG. 38 is a block diagram of (part of) a medical ultrasound system with integrated controlled dispersion of coupling fluid, in accordance with an embodiment. Medical ultrasound system 100 includes an ultrasound head 500. Coupled with the ultrasound head 500 are one or more coupling fluid dispersion devices 582, such as spray nozzles, through which coupling fluid is dispersed. A flow control subsystem 584 is used to control the transfer of coupling fluid from a coupling fluid source 586 to the one or more coupling fluid dispersion devices 582.

In an embodiment, the system 100 is configured so that a doctor, technician or other user can control the dispersion of the cooling fluid while holding the ultrasound head in his or her hands by using a trigger 514 (FIG. 39) positioned on the upper compartment 510, and within easy reach while holding the treatment head 500. By dispersing the cooling fluid distributed by the fluidics system of the base unit, the operator can produce a viable coupling fluid without taking their hands off the therapy head, or being distracted while reaching for an accessory device for dispersing a separate coupling fluid. Thus, in an embodiment, the cooling fluid used inside the system, may also be a coupling fluid used outside the system. The dispersed fluid is referred to as coupling fluid when it is outside (dispersed) the system.

The coupling fluid may be applied by the coupling fluid dispersion devices 582 by spraying the coupling fluid onto the skin. For example, the one or more coupling fluid dispersion devices 582 can include one or more spray nozzles configured to disperse a volume of water on a patient's skin as discussed above. The one or more spray nozzles can be positioned and oriented relative to the ultrasound head so that they can spray around the transducer cartridge to disperse coupling fluid on the patient's skin that is located under the flexible window when the ultrasound head is spaced slightly from the patient. Although a single spray nozzle can be used, in an embodiment, multiple spray nozzles are used so that each of the spray nozzles need only be positioned and oriented so as to cover a portion of the patient's skin located under the flexible window.

The one or more fluid dispersion devices 582 can also be configured to introduce coupling fluid into the space between the flexible window 602 and the skin surface so that the coupling fluid may spread out evenly by capillary action. In such an arrangement, the nozzles are used to disperse a volume of coupling fluid on the patient's skin so the skin surface is at least lightly wetted. As the coupling fluid is sprayed on the skin surface, droplets form are deposited on the skin. In one aspect the droplets remain small and separate from one another so the droplets do not pool together and roll off the skin surface. When the cartridge 600 is placed on the moistened skin surface, the droplets are compressed. The droplets collapse and run together to form a thin film of coupling fluid. The thin film of coupling fluid may be held in place between the transducer and the skin by capillary attraction.

In addition to or instead of one or more spray nozzles oriented as discussed above, the fluid dispersion device 582 may use various other fluid introduction approaches. For example, one or more fluid lines may be positioned and oriented so that discharged coupling fluid is introduced into the space between the flexible window and the skin surface. As a further example, coupling fluid may be supplied to a peripheral manifold having multiple discharge ports distributed around the periphery of the flexible window. One or more peripheral sealing members can also be used to help retain coupling fluid between the flexible window and the patient's skin.

In another embodiment, if the ultrasound head 500 is held in close proximity to a skin surface, the coupling fluid may be introduced into the space between the flexible window 602 and the skin surface, and the coupling fluid may spread out evenly by capillary action. For example, a spray nozzle can be oriented so as to spray water towards a peripheral gap between the flexible window 602 and the skin surface. Even distribution may be promoted by gently rocking the ultrasound head over the skin surface to help push out large air pockets.

The flow control subsystem 584 can include a variety of components. For example, the flow control subsystem 584 can include a hand pump or hand actuated switch 514 coupled with the ultrasound head or can include a foot pump or foot actuated switch positioned for use while the surgeon of technician is holding the ultrasound head. The flow control subsystem can be manually actuated, such as by a hand or foot operated pump. The flow control subsystem 584 can include a combination of one or more electrical pumps, control valves, and/or control switches.

Various coupling fluid sources 586 can also be used. For example, a combined coupling/cooling fluid reservoir can be used to hold a quantity of coupling/cooling fluid for subsequent dispersion onto a patient's skin. A coupling fluid source can also be a fluid supply line, such as a water supply line where water is used as the coupling fluid. As will be discussed below in more detail, a coupling fluid source can include a fluid system, such as a fluid system configured to use water to cool the ultrasound head.

Figure 39:
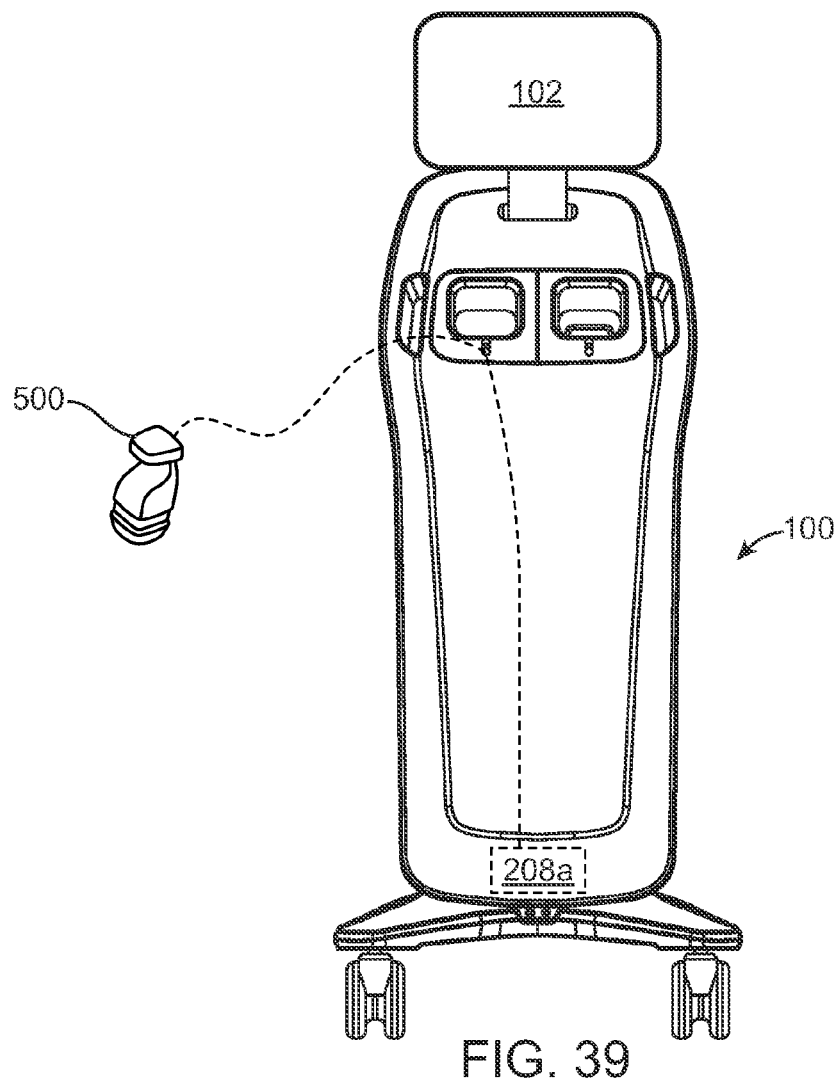
FIG. 39 shows a medical ultrasound system having a coupling fluid reservoir and a coupling fluid line, in accordance with an embodiment.
Figure 41:
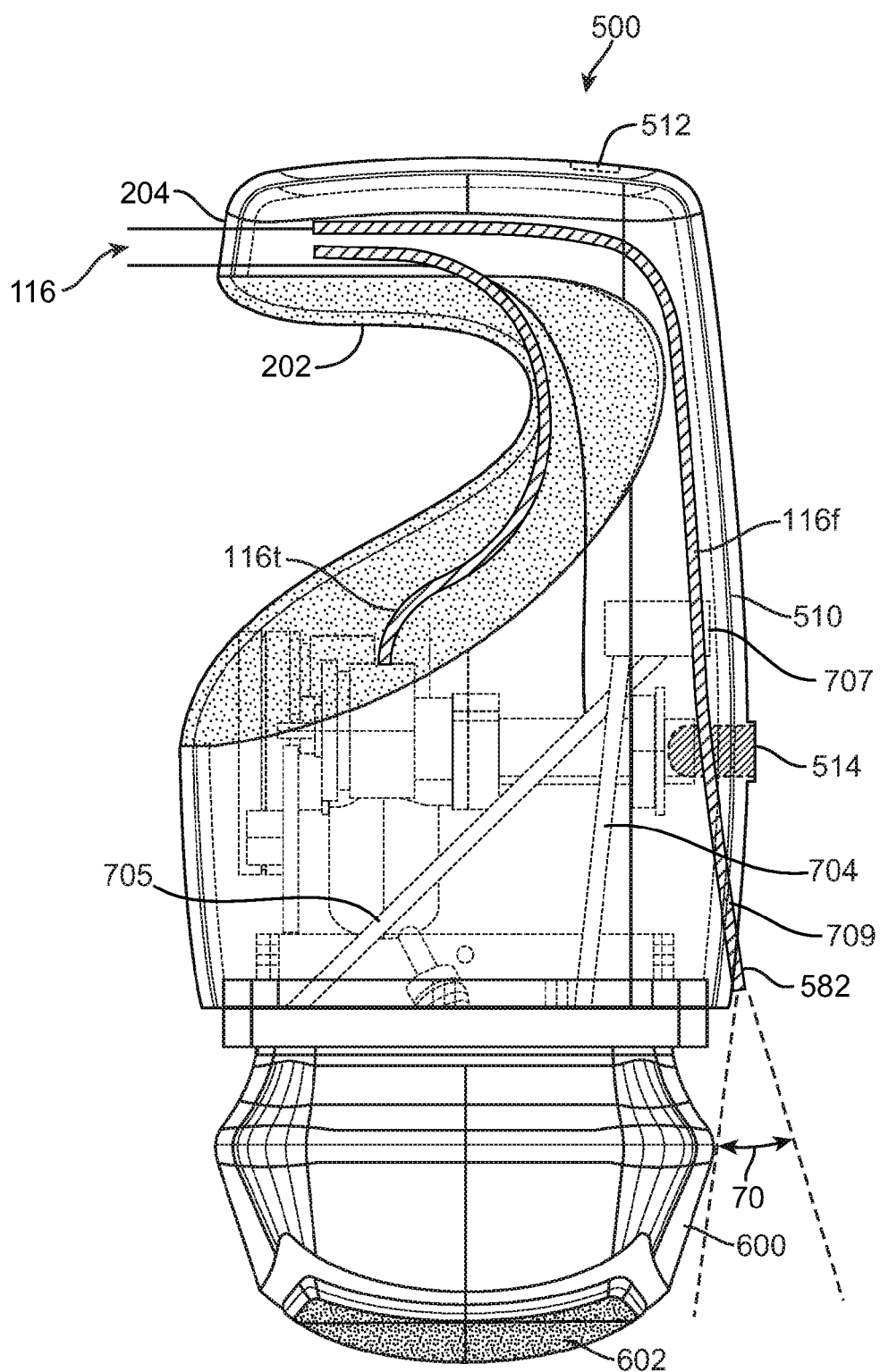
FIG. 41 is a transparent side view of a treatment head having a spray nozzle according to an embodiment.

FIG. 39 illustrates a medical ultrasound system 100 that includes a coupling fluid reservoir 208*a* as the coupling fluid source. Ultrasound system 100 includes a base unit 130 and an ultrasound head 500 having a unigrip handle 202. A coupling fluid reservoir 208*a* can be located within base unit 130 and coupled with one or more coupling fluid dispersion devices via one or more coupling fluid lines 116*f* (FIG. 41). A flow control subsystem that includes one or more flow control devices, such as a solenoid valve and/or a fluid pump, can be used to control fluid communication between the reservoir and the one or more fluid dispersion devices. For example, where the coupling fluid in the reservoir 208*a* is pressurized (e.g., at 10 to 20 psig), a valve (e.g., a solenoid valve) can be used to regulate the dispersion of control fluid. A cable 116 from the base unit is shown with the fluid lines 116*f* from the interface cable descending into a fluid controller 707. From the fluid controller 707 one fluid line 709 goes to the sprayer 582. Multiple lines may be used to feed multiple sprayers. Other fluid lines exiting the fluid controller are the fluid input line for a fluid path 704 to the cooling device 750. A return line 705 is also shown where warm water returns from the cartridge to the fluid circulation circuit 700. FIG. 41 also one possible route of the power and coax lines 116t by going through the motor assembly and entering the cartridge through the center of the control arm 578. Alternatively the power and control lines for the transducer assembly may go through a separate electrical connector.

A control switch, such as a momentary switch (i.e., normally open switch where the contacts engage only while held in the closed position), can be used to activate the solenoid valve. A control switch can also be used to activate a pump that transfers coupling fluid from the reservoir to the one or more fluid dispersion devices (e.g., spray nozzles). A combination of a pump and a solenoid valve can also be used. Manually actuated pumps, such as hand or foot actuated pumps, can also be used. A flow control device can be located inside the reservoir 208*a* or along the coupling fluid line 116*f*.

A control switch can be located for convenient use by an operator of the medical ultrasound system such that the operator does not have to take their hands off the handles of the ultrasound head. For example, the control switch, such as momentary switch, can be coupled with one of the handles so as to be operable by the operator's thumbs. As a further example, a foot activated control switch can also be used. Such a foot activated control switch can be coupled with the base unit directly in a convenient location, or can be a separate unit that can be positioned by the operator in a convenient location.

In another embodiment, coupling fluid extracted from a fluid system that has another function for the device 100 can be sprayed onto the skin for use as a coupling fluid. For example, water can be extracted from a cooling system and sprayed onto the patient's skin for use as a coupling fluid. For example, such a cooling system can be configured to circulate cooling water between a heat exchanger located within the ultrasound head and an external heat exchanger. The cooling water can absorb heat from the ultrasound head and release the heat at the external heat exchanger. After absorbing heat from the ultrasound head, the cooling water may be at a temperature where it can be sprayed onto a patient's skin without causing discomfort (i.e., not too cold and not too hot). The cooling system can be coupled with a supply reservoir or supply line to replenish the cooling system for any cooling water dispersed. Other fluid systems may be used.

Figure 40:
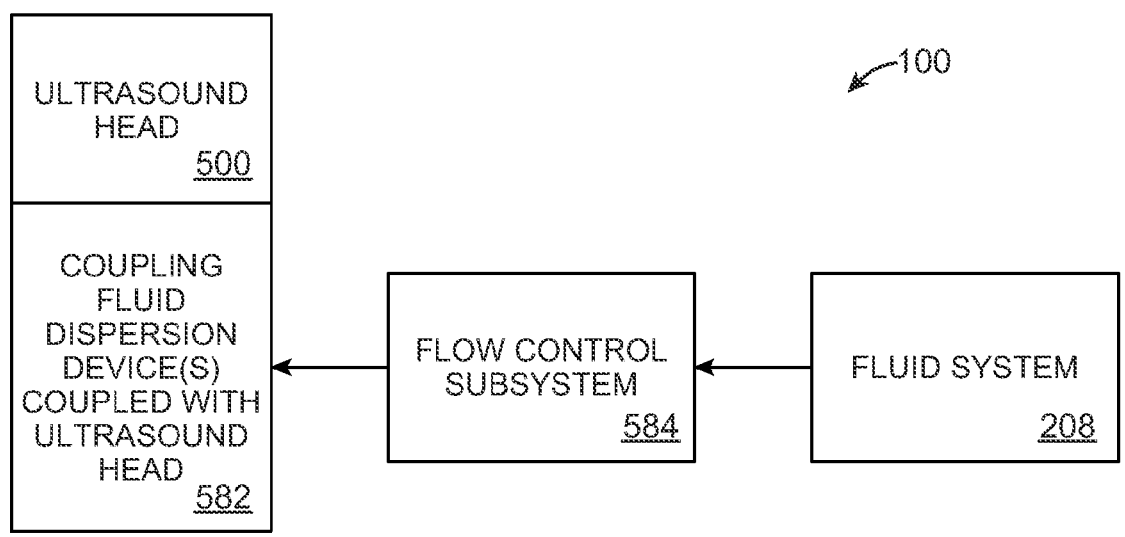
FIG. 40 is a block diagram of fluid flow system, in accordance with an embodiment.

FIG. 40 is a block diagram of (part of) a medical ultrasound system 100, in accordance with an embodiment, having a fluid system 208 from which the coupling fluid can be obtained. Similar to the medical ultrasound system 100 discussed above, the medical ultrasound system 100 includes an ultrasound head 500, one or more coupling fluid dispersion devices 582 coupled with the ultrasound head and a flow control subsystem 584 that is used to control the transfer of coupling fluid from the fluid system 208 to the one or more fluid dispersion devices 582 (FIG. 41). The fluid system 208 can be any fluid system that contains a coupling fluid (e.g., water), such as a cooling system that is configured to use water to cool the ultrasound head so as to dissipate heat generated by the ultrasound transducer. The one or more coupling fluid dispersion devices 582 and the flow control subsystem 584 can include various components and configurations, such as those discussed above with reference to the medical ultrasound system 100 (shown in FIG. 39).

Figure 44A:
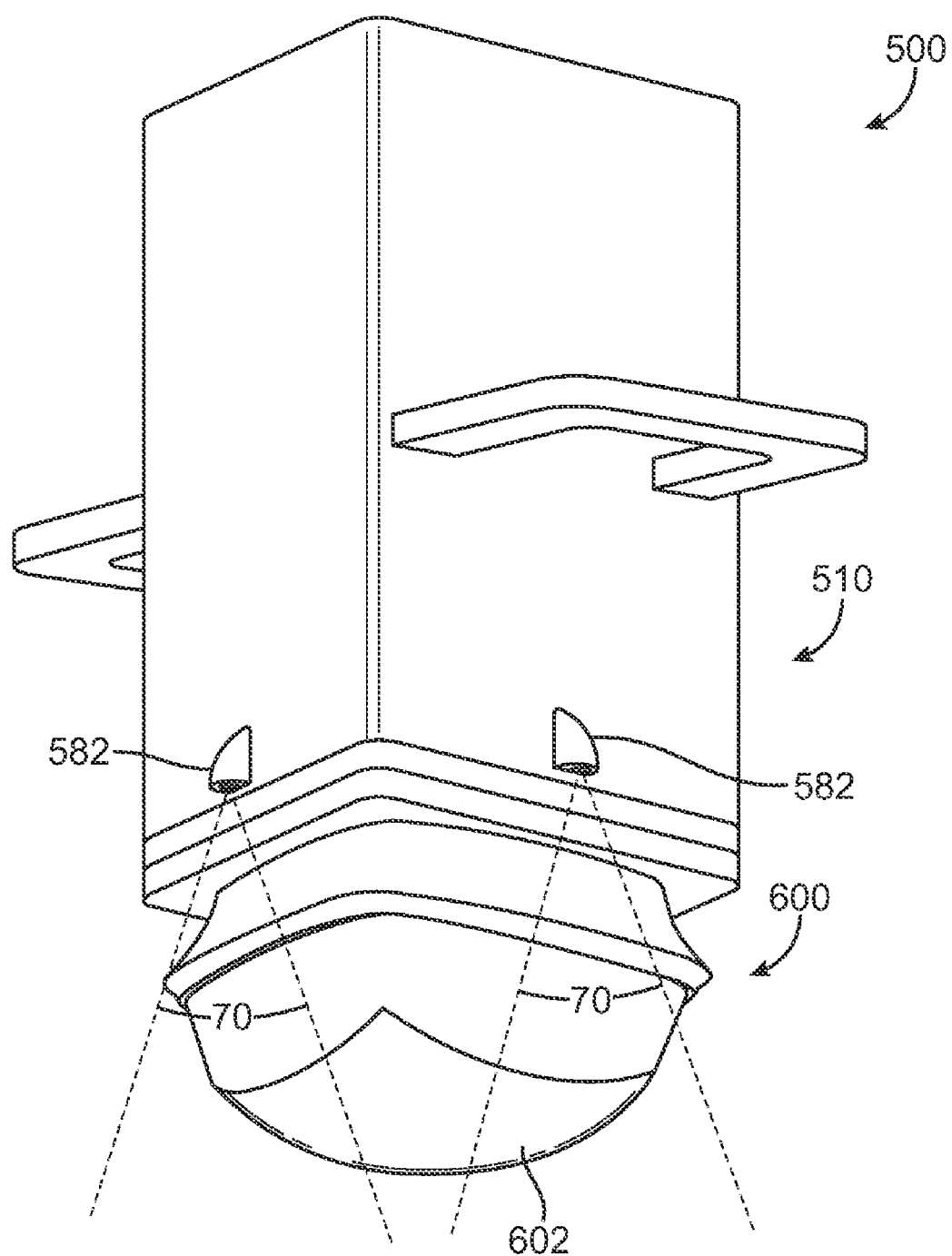
FIG. 44A is a perspective view of an ultrasound head having integrated spray nozzles, in accordance with an embodiment.

FIG. 44A is a perspective view of an ultrasound treatment head 500 having integrated spray nozzles 582, in accordance with an embodiment. The integrated spray nozzles 582 can be distributed around the ultrasound treatment head 500 and oriented so as to disperse coupling fluid as discussed above. While two spray nozzles 582 are shown, one or more spray nozzles 582 can be used. For example, four spray nozzles can be used with each side of the ultrasound head 582 having one spray nozzle 582 disposed thereon. A spray nozzle 582 can be positioned and oriented so as to disperse coupling fluid via a spray pattern 70. As discussed above, the one or more spray patterns 70 can be used to disperse and/or introduce coupling fluid on the patient's skin located underneath the flexible window 602 when the flexible window 602 is held adjacent to the patient's skin. In an embodiment, the one or more spray patterns 70 are configured so that they will fully cover the area of the skin underneath the flexible window 602 when the flexible window is spaced a predetermined distance from the patient's skin.

Figure 44B:
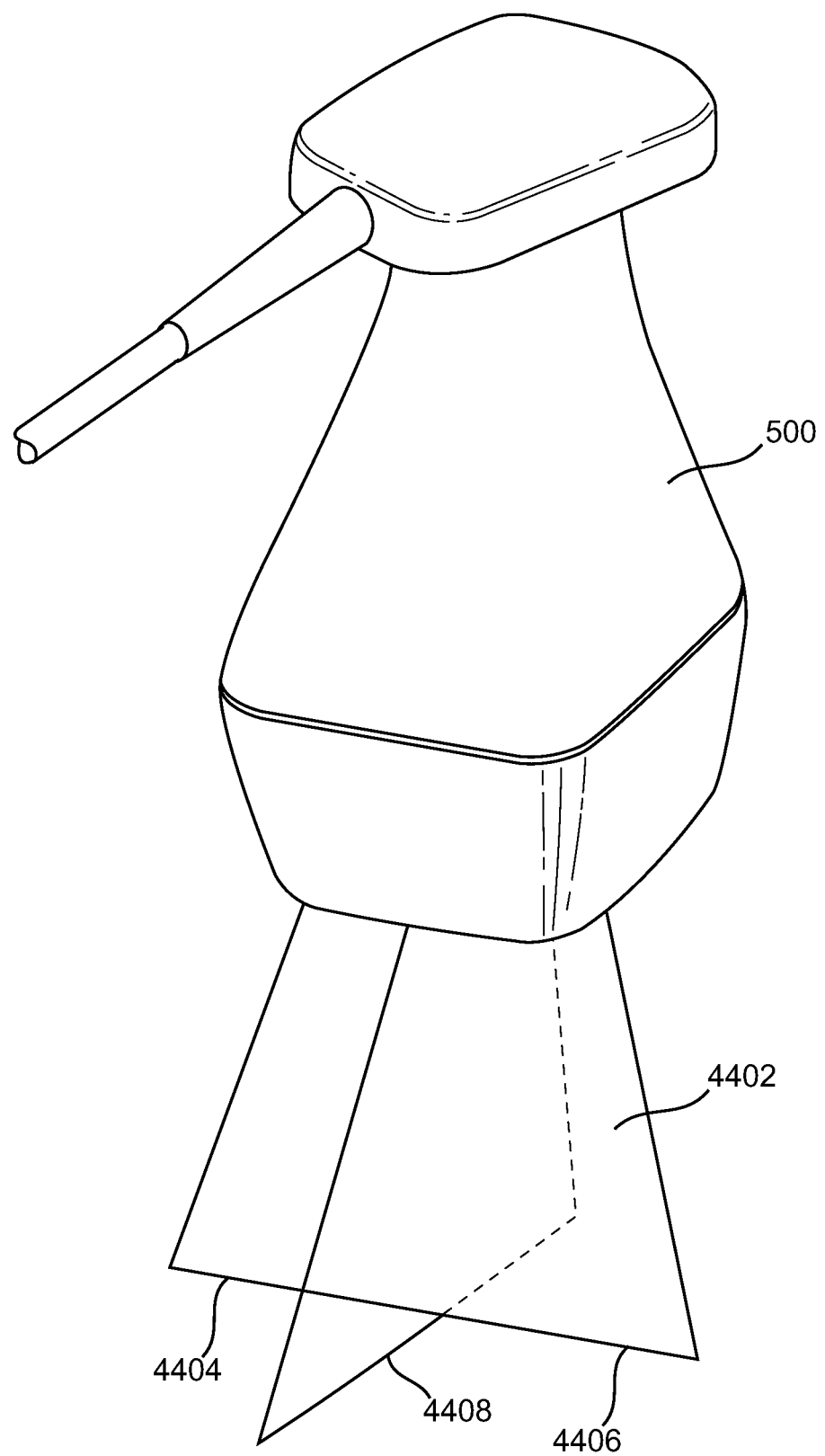
FIG. 44B provides a view of an ultrasound therapy head having a guide component for the liquid dispersal device(s) according to an embodiment.

FIG. 44B provides an embodiment of aligning the therapy head 500 to grid lines drawn on the patient body, as described below. The therapy head may project alignment markers via guide lights 4402, 4404 on the patient skin in the form of intersecting lines 4406, 4408, using lasers, LED lights or other light projecting elements. Such elements are readily available and may be incorporated on to the exterior of the therapy head to produce a guide indicia for the user. The light source may be directly presented on to the patient skin or through a reflective device (such as an oscillating reflector sometimes used with a laser to produce a visual scan line).

Figure 42:
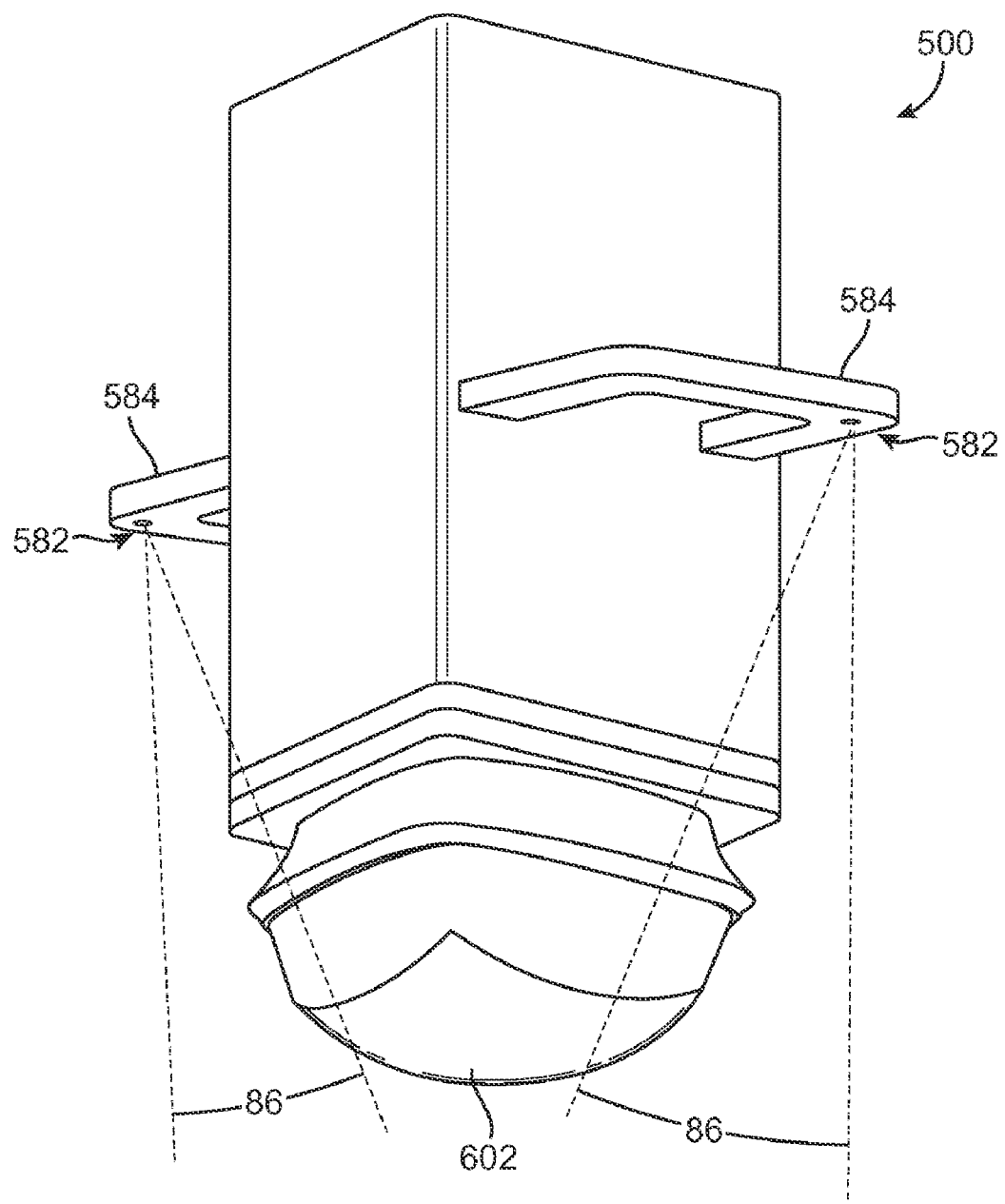
FIG. 42 is a perspective view of an ultrasound head having handles and spray nozzles coupled with the handles, in accordance with an embodiment.

FIG. 42 is a perspective view of an ultrasound treatment head 500 having one or more spray nozzles 582 disposed within handles 584, in accordance with an embodiment. A spray nozzle 582 can be disposed in a region of a handle 584 that is offset from the ultrasound therapy head 500 so that the spray pattern 86 can be directed towards the patient's skin located under the flexible window 602 when the ultrasound head is held adjacent to the patient's skin. Such an orientation can help to reduce the amount of movement of the ultrasound head from its position during coupling fluid application to its position during ultrasonic treatment or diagnostic test. The ultrasound head can be moved into contact with the skin after the coupling fluid has been applied. The one or more spray nozzles 582 can be located and oriented such that the resulting spray patterns 86 do not impinge upon the surgeon's or technician's hands while he or she is holding the ultrasonic head by the handles 584.

Figure 43:
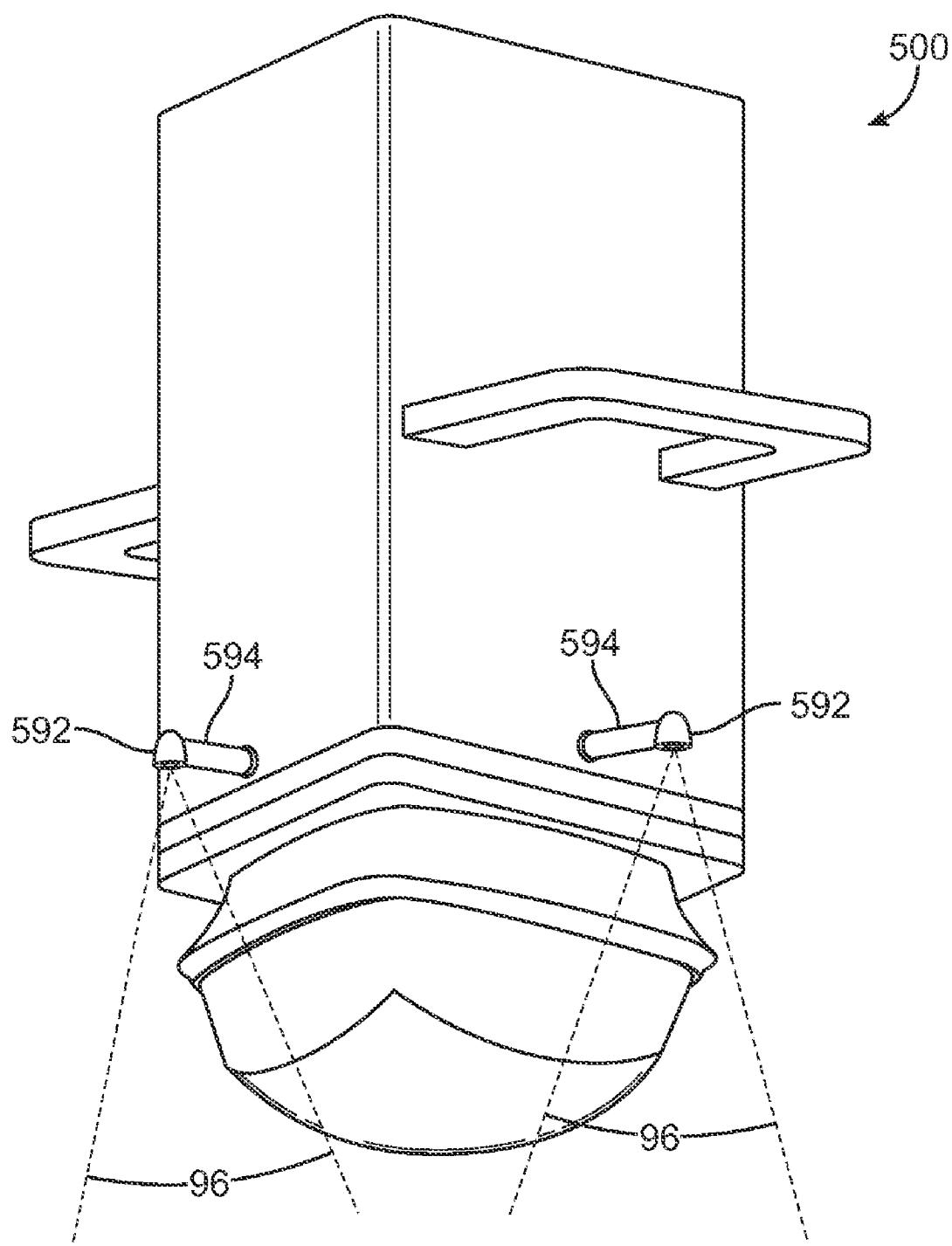
FIG. 43 is a perspective view of an ultrasound head having offset spray nozzles, in accordance with an embodiment.

FIG. 43 is a perspective view of an ultrasound treatment head 500 having one or more offset spray nozzles 592, in accordance with an embodiment. The one or more spray nozzles 592 can be offset from the ultrasonic treatment head 500, such as by way of one or more conduits 594. As noted above, with such an offset the one or more spray nozzles 592 can be oriented to result in one or more spray patterns 96 that reduce the amount of movement of the ultrasound head from its position during coupling fluid application to its position during the ultrasonic treatment or diagnostic test. The spray conduits may be fixed or retractable.

Figure 45:
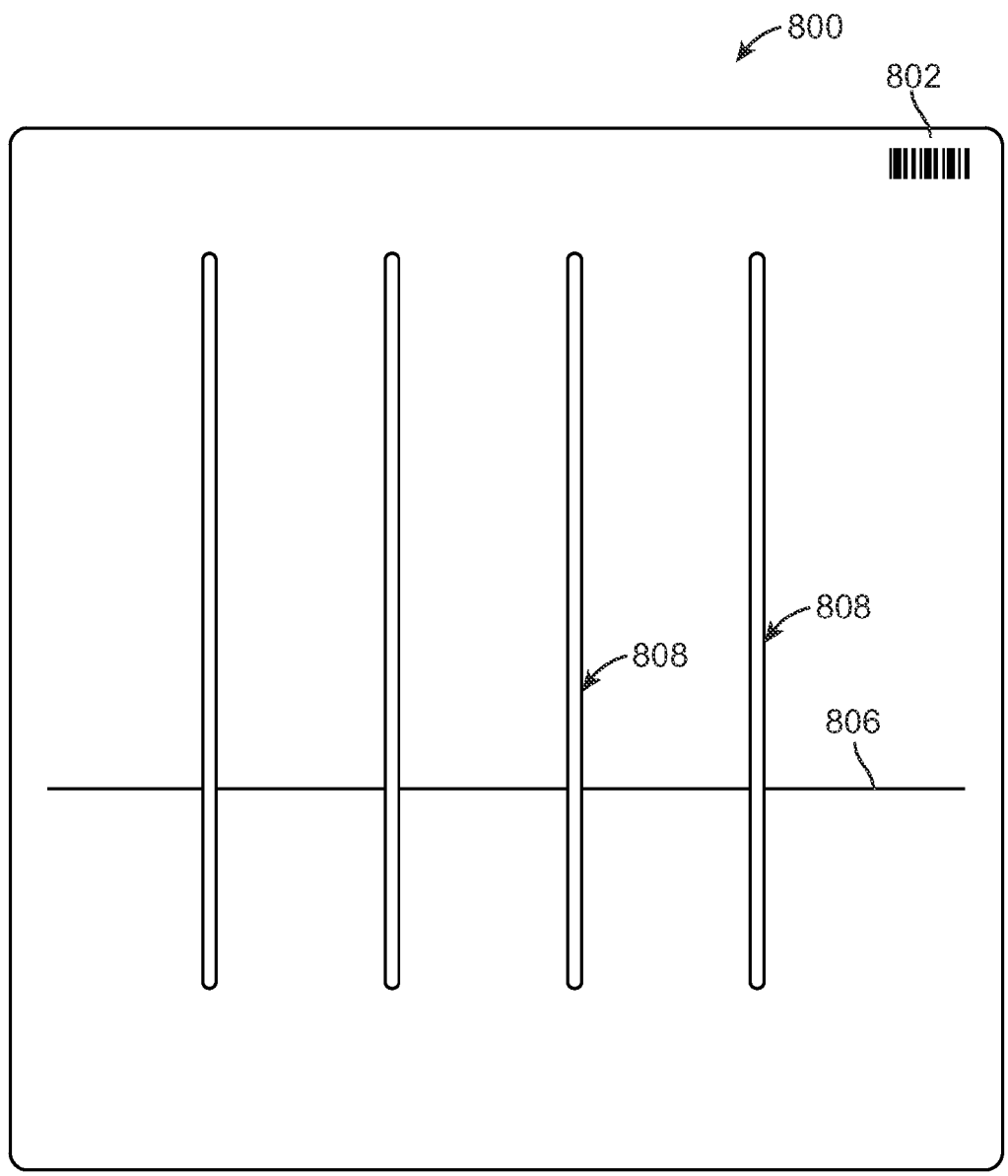
FIG. 45 is an illustration of a template for use in creating a variable size and alignment pattern on a patient body according to an embodiment.

To align the treatment head 500 on a patient body, a physician can first make a pattern of guidelines on the patient skin. The pattern of guidelines form one or more site areas. Guidelines allow a physician or user to place the treatment head on to the patient and proceed in an orderly fashion to treat the desired volume of tissue underneath the guidelines. The guidelines described herein are created using one of several guideline templates 800 (FIG. 45). The treatment head 500 can include alignment markers either on the cartridge 600 and/or on the upper compartment 510, so the user can align the therapy head 500 with the guidelines on the patient. The alignment markers can be located on the sides of the therapy head instead of the corners.

Figure 46:
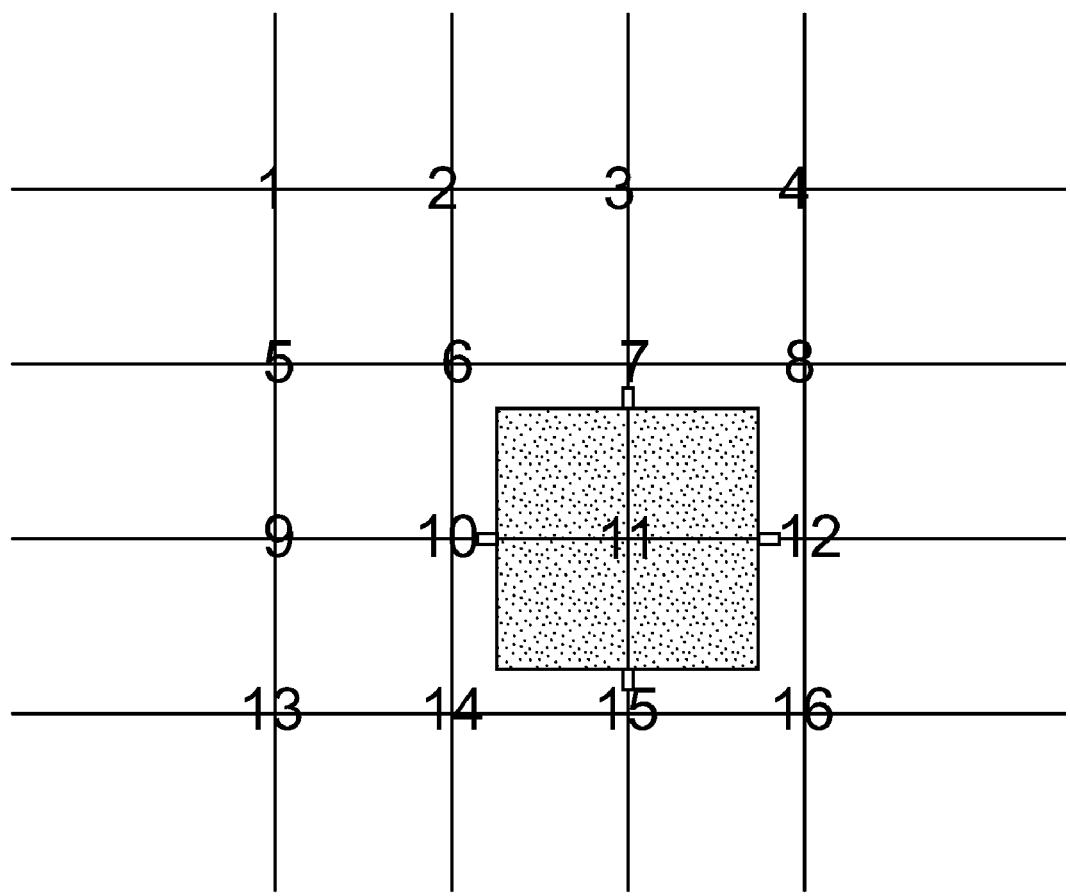
FIG. 46 is an illustration of the use of a variable treatment size pattern in an embodiment.
Figure 47:
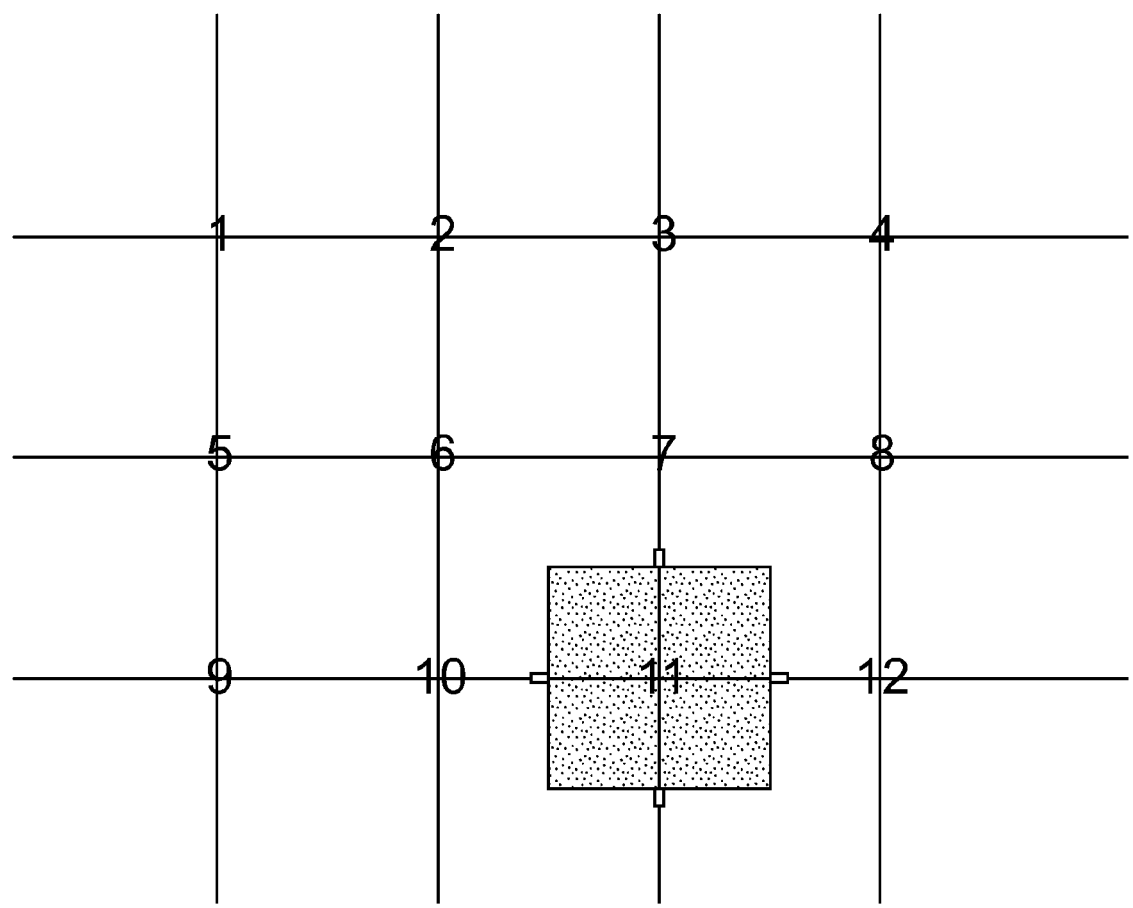
FIG. 47 is an illustration of the use of a variable treatment alignment pattern according to an embodiment.

In an aspect of the assembled therapy head, using the features of the sides of the treatment head 600 as the alignment feature of the treatment head allows a user to treat variable sized areas that are less than the foot print of the therapy head on the patient's skin. If a complete grid is drawn on the patient, then the spacing of the lines of the grid do not have to line up with the size of the treatment head face (as long as they are smaller than the treatable area of the treatment head if spaces between sites are not desired). In effect the alignment is about the intersection of the horizontal and vertical lines of the grid rather than the area encompassed by the lines. This allows for a given treatment head with its physical treatment head area to not have to match the treatment area the user may want. Another way to state it is that a given treatment head area (size) can be used with multiple grid size templates based on the area and shape of the desired treatment region. Two examples are shown in FIGS. 46 and 47 with FIG. 47 having the grid be the same size as the treatment head, while FIG. 46 has the area of the site being about ¾ the area of the treatment head. Other variations are of course possible, but are not diagrammed so as to prevent the application from being prolix.

The grid itself is very quick and easy to draw compared to marking corners. With lines we end up with Number of Lines drawn=(rows+1)+(columns+1). With corners we end up with Number of corners=(rows+1)*(columns+1). So for example with 4 rows by 5 columns of treatment grid area we have 11 lines to draw versus 30 corners. An example template 800 is shown in FIG. 45. The template 800 includes parallel guidelines 808 that allow a user to draw lines 806 on a patient. As an example, the user may draw one set of parallel lines, rotate the template 800 ninety degrees, and then draw a second set of lines that crosses the first set of lines. The two sets of lines then form a grid, such as one of the grid patterns shown in FIG. 46 or 47.

If variable site areas and various templates are available to mark guidelines, then it can be desirable to minimize the chance of a user making an error by marking one size grid on the patient and then setting up the system to treat a different size site. To minimize this chance a feature that the system can read could be embedded into the template. Then after the user marks the patient they would then present the template to the system to have it read the feature, which may be a marked site area, for example, to set up the machine to match the patient markings This feature could be implemented with an embedded barcode 802 on the marking template 800 or with radio frequency identification (RFID) type tags embedded into the template. In either case the user would "scan" the template into the system to allow entering the treatment screen to set up the system for the correct site area.

In use, a user places the template 800 on a patient, marks the gridlines 806 in one direction using the guidelines 808, rotates the template ninety degrees, and marks a second set of guidelines 806. Thus, a grid is formed. The user then aligns the side features on the treatment head 600 with two crossing lines. The center of the treatment head 600 thus is aligned where two guidelines cross.

If provided, the barcode 802 or other feature may be scanned or otherwise entered into the system after gridlines 806 are applied. In this manner, the settings of the treatment head 600 may be matched to a grid.

In an embodiment, the user is able to further define the area of treatment by using a user defined treatment tool. This embodiment provides a medical ultrasound system having the base unit with the previously described system electronics, user interface and ultrasound control electronics. The ultrasound therapy head is in electronic communication with the base unit, the therapy head has a high intensity focused ultrasound (HIFU) transducer disposed within it.

The user interface can include a touch screen interface. The touch screen can detect menu selections, and free hand drawings made either using a stylus or appendage of the user. A coordination operation coordinates the designs of free hand drawings and provides data to the ultrasound control electronics such that a user can define safe or "not safe" treatment zones through free hand drawings and enable the ultrasound control electronics to distinguish safe verse not safe treatment zones during a therapy regiment.

The ultrasound control electronics can prevent the transducer from broadcasting ultrasound energy into the "not safe" zones by controlling either the broadcasting of ultrasonic energy by the transducer, or the motor control for moving the transducer. In an embodiment, the ultrasound control electronics control a motor drive unit and prevent the motor drive unit from moving the HIFU transducer over the "not safe" treatment zones. In another embodiment, the ultrasound control electronics control the operation of the HIFU transducer and prevent the HIFU transducer from broadcasting HIFU energy over the "not safe" treatment zones. In a third embodiment the ultrasound control electronics prevent the movement over the no safe zone, and prevent the firing of the transducer over the "not safe" zones, and selects one or the other depending on the size and shape of the "not safe" zone so as to select the option most efficient for the system operation. Variations and/or combinations of these embodiments can be used.

In another embodiment, the system has a scanner for recording lines from a patient's body, the lines defining a treatment area and a non-treatment area. The system can detect through a preprogrammed detection method in the scanner, which are safe and not safe treatment zones. This may be achieved by using different colors on the safe verses not safe treatment areas (e.g. green and red), or using other indicia the scanner is able to detect and correlate with a preprogrammed detection method.

Figure 48:
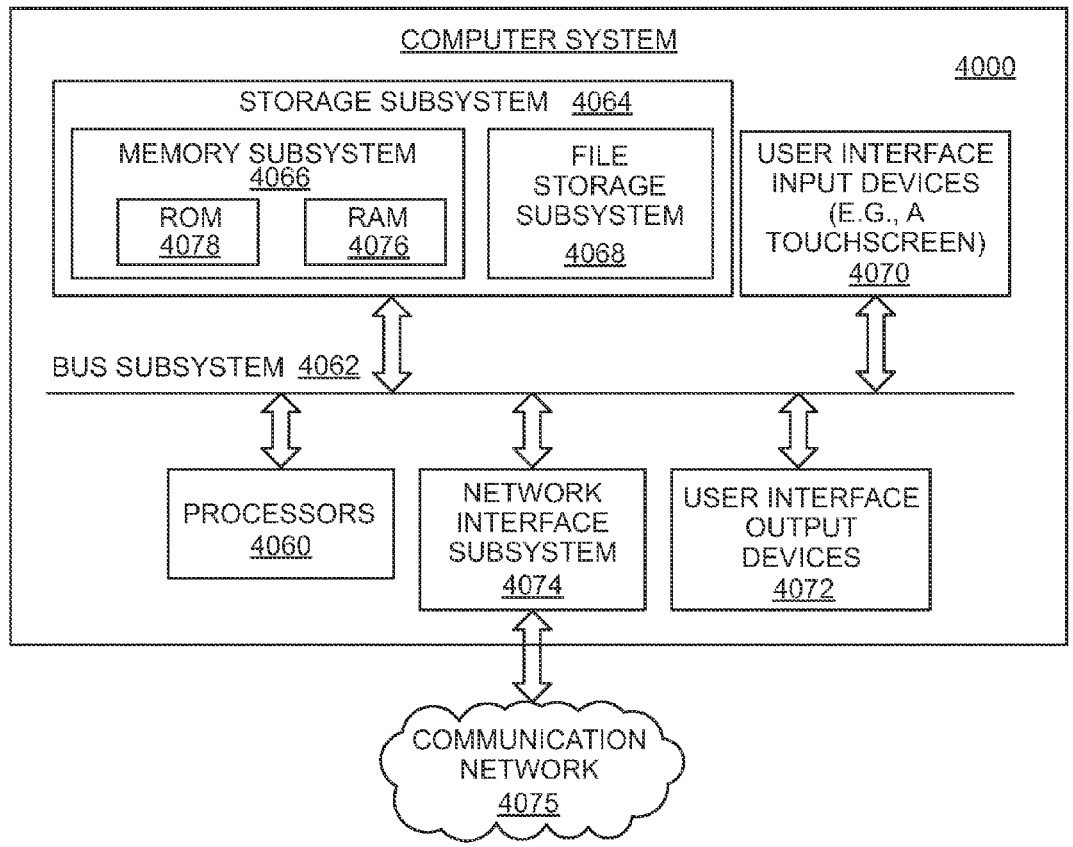
FIG. 48 illustrates a simplified block diagram of a computer system in accordance with embodiments.

FIG. 48 is a simplified block diagram of an exemplary computer system 4000 in accordance with embodiments. The computer system typically includes at least one processor 4060 which communicates with a number of peripheral devices via a bus subsystem 4062. These peripheral devices may include a storage subsystem 4064, comprising a memory subsystem 4066 and a file storage subsystem 4068, user interface input devices 4070, user interface output devices 4072, and a network interface subsystem 4074. Network interface subsystem 4074 provides an interface to a communication network 4075 for communication with other imaging devices, databases, or the like.

The processor 4060 performs the operation of the computer systems 4000 using execution instructions stored in the memory subsystem 4066 in conjunction with any data input from an operator. Such data can, for example, be input through user interface input devices 4070, such as the graphical user interface. Thus, processor 4060 can include an execution area into which execution instructions are loaded from memory. These execution instructions will then cause processor 4060 to send commands to the computer system 4000, which in turn control the operation of the ultrasound control electronics. Although described as a "processor" in this disclosure and throughout the claims, the functions of the processor may be performed by multiple processors in one computer or distributed over several computers.

User interface input devices 4070 may include a keyboard, pointing devices such as a mouse, trackball, touch pad, or graphics tablet, a scanner, foot pedals, a joystick, a touch screen incorporated into the display, audio input devices such as voice recognition systems, microphones, and other types of input devices. In general, use of the term "input device" is intended to include a variety of conventional and proprietary devices and ways to input information into the computer system. Such input devices will often be used to download a computer executable code from a computer network or a tangible storage media embodying steps or programming instructions for any of the methods of the present invention.

User interface output devices 4072 may include a display subsystem, a printer, a fax machine, or non-visual displays such as audio output devices. The display subsystem may be a cathode ray tube (CRT), a flat-panel device such as a liquid crystal display (LCD), a projection device, or the like. The display subsystem may also provide non-visual display such as via audio output devices. In general, use of the term "output device" is intended to include a variety of conventional and proprietary devices and ways to output information from the computer system to a user.

Storage subsystem 4064 stores the basic programming and data constructs that provide the functionality of the various embodiments. For example, database and modules implementing the functionality of embodiments described herein may be stored in storage subsystem 4064. These software modules are generally executed by processor 4060. In a distributed environment, the software modules may be stored in a memory of a plurality of computer systems and executed by processors of the plurality of computer systems. Storage subsystem 4064 typically comprises memory subsystem 4066 and file storage subsystem 4068.

Memory subsystem 4066 typically includes a number of memories including a main random access memory (RAM) 4076 for storage of instructions and data during program execution and a read only memory (ROM) 4078 in which fixed instructions are stored. File storage subsystem 4068 provides persistent (non-volatile) storage for program and data files, and may include a hard disk drive, re-writable non-volatile memory chips (such as Flash memory), a floppy disk drive along with associated removable media, a Compact Digital Read Only Memory (CD-ROM) drive, an optical drive, DVD, CD-R, CD-RW, or removable media cartridges or disks. One or more of the drives may be located at remote locations on other connected computers at other sites coupled to the computer system. The databases and modules implementing the functionality of the present invention may also be stored by file storage subsystem 4068. The file storage subsystem may have directory and file descriptions for accessing the files, or it may store data without descriptions and rely on the databases and modules of the system to locate the data.

Bus subsystem 4062 provides a mechanism for letting the various components and subsystems of the computer system communicate with each other as intended. The various subsystems and components of the computer system need not be at the same physical location but may be distributed at various locations within a distributed network. Although bus subsystem 4062 is shown schematically as a single bus, alternate embodiments of the bus subsystem may utilize multiple busses.

The computer system 4000 itself can be of varying types including a personal computer, a portable computer, a workstation, a computer terminal, a network computer, a module in a circuit board, a mainframe, or any other data processing system. Due to the ever-changing nature of computers and networks, the description of the computer system depicted in FIG. 48 is intended only as a specific example for purposes of illustrating one embodiment. Many other configurations of the computer system are possible having more or less components than the computer system depicted in FIG. 48.

Figure 49:
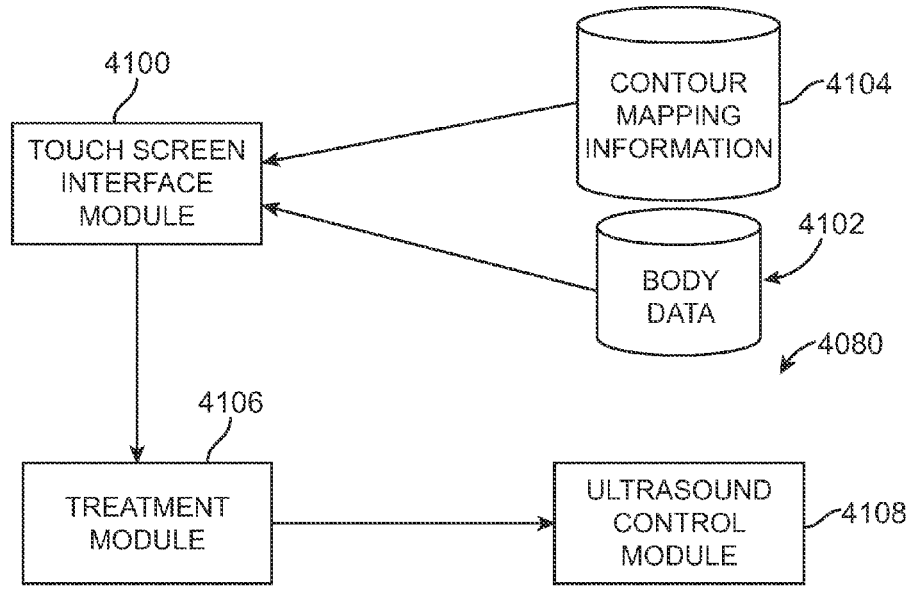
FIG. 49 schematically illustrates a series of modules according to an embodiment.

FIG. 49 schematically illustrates a plurality of modules 4080 that may carry out embodiments. The modules 4080 may be software modules, hardware modules, or a combination thereof. If the modules are software modules, the modules will be embodied on a computer readable medium and processed by a processor 4060 in any of computer systems of the present invention.

A first module is a touch screen interface module 4100. The touch screen interface module receives data from the touch screen, e.g., the user interface input device 4070, as described above. In addition, the touch screen interface module may be configured to receive body data 4102 and/or contour/mapping information 4104.

Information from the touch screen interface module is forwarded to a treatment module 4106. The treatment module 4106 generates treatment information and forwards that information to an ultrasound control module 4108, which in turn controls the ultrasound electronics for the device.

The modules 4080 are designed so that an operator may enter information into a touch screen interface, which is in turn received by the touch screen interface module 4100. The touch screen can detect menu selections and freehand drawings or other contact made with the touch screen made using either a stylus or a finger of the user.

Figure 50:
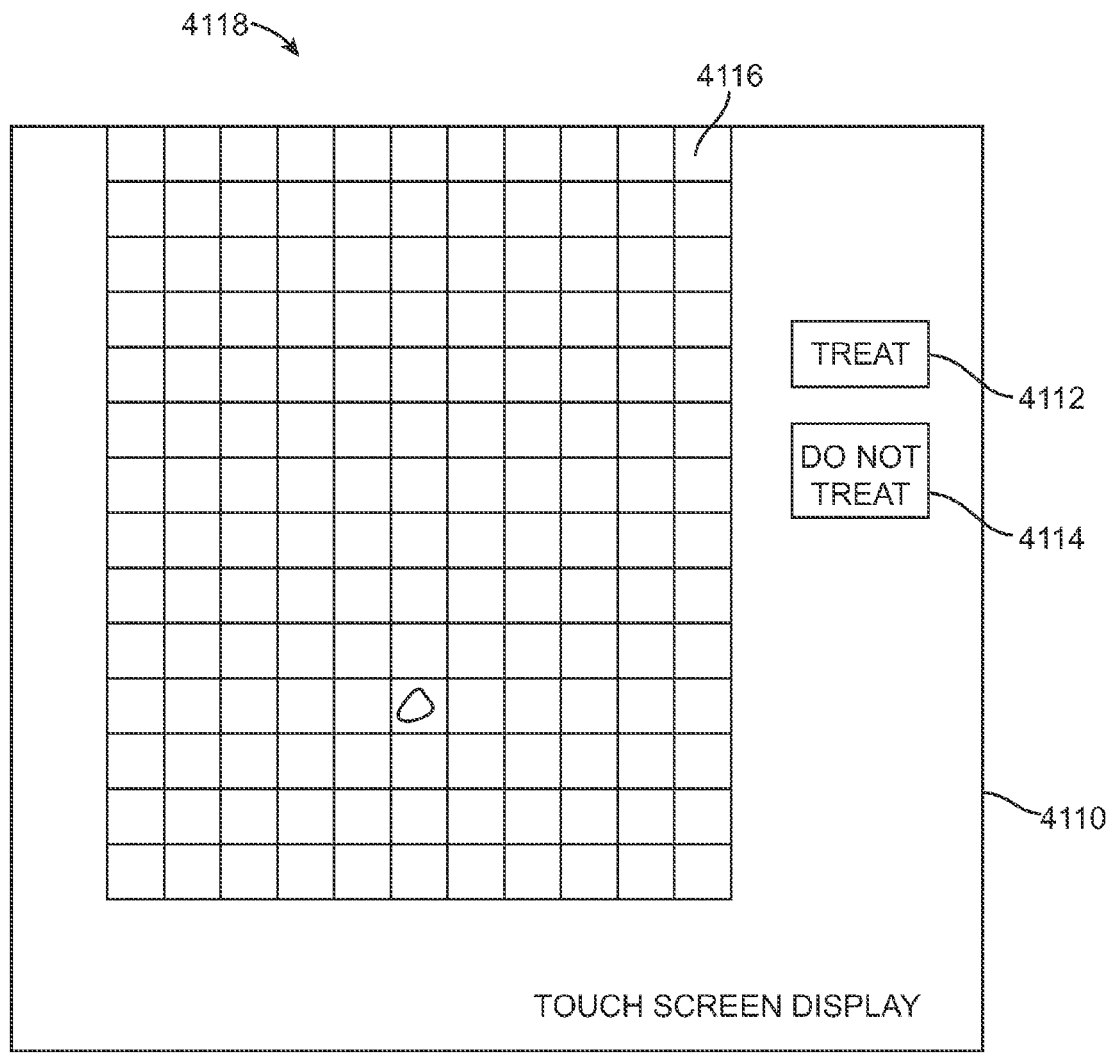
FIG. 50 is an example of a touch screen.

For example, in FIG. 50, a display 4110 for a touch screen is shown. In the display, menu selections are provided in the form of a treat button 4112 and a do not treat button 4114. These menu selections may be provided on the touch screen 4110 or via another selection device. In addition, the selection items may be called something else, such as "safe" and "nonsafe" zones or may use some other terminology.

The touch screen interface module utilizes the body data 4102 to display an image or representation of the body of the user, shown by the reference number 4116 on the touch screen display 4110. In the embodiments shown in the drawings, only a portion of a user's abdomen is shown, but a larger part of the body may be represented.

The touch screen interface module 4100 may access the contour/mapping information 4104 and overlay that information on the body image 4116. For example, a grid 4118 may be overlaid over the user. This grid may correspond with a grid that is drawn on the patient or projected on the patient.

In either event, the touch screen display 4110 shows some type of representation of a patient's body 4116 and provides some mapping or grid information that permits correlation between the patient's body and intended treatment areas on the body. Scanners, X-ray information, photographs, grid data or other information may be used to coordinate between the body data 4102 and the contour/mapping information 4104.

Figure 51:
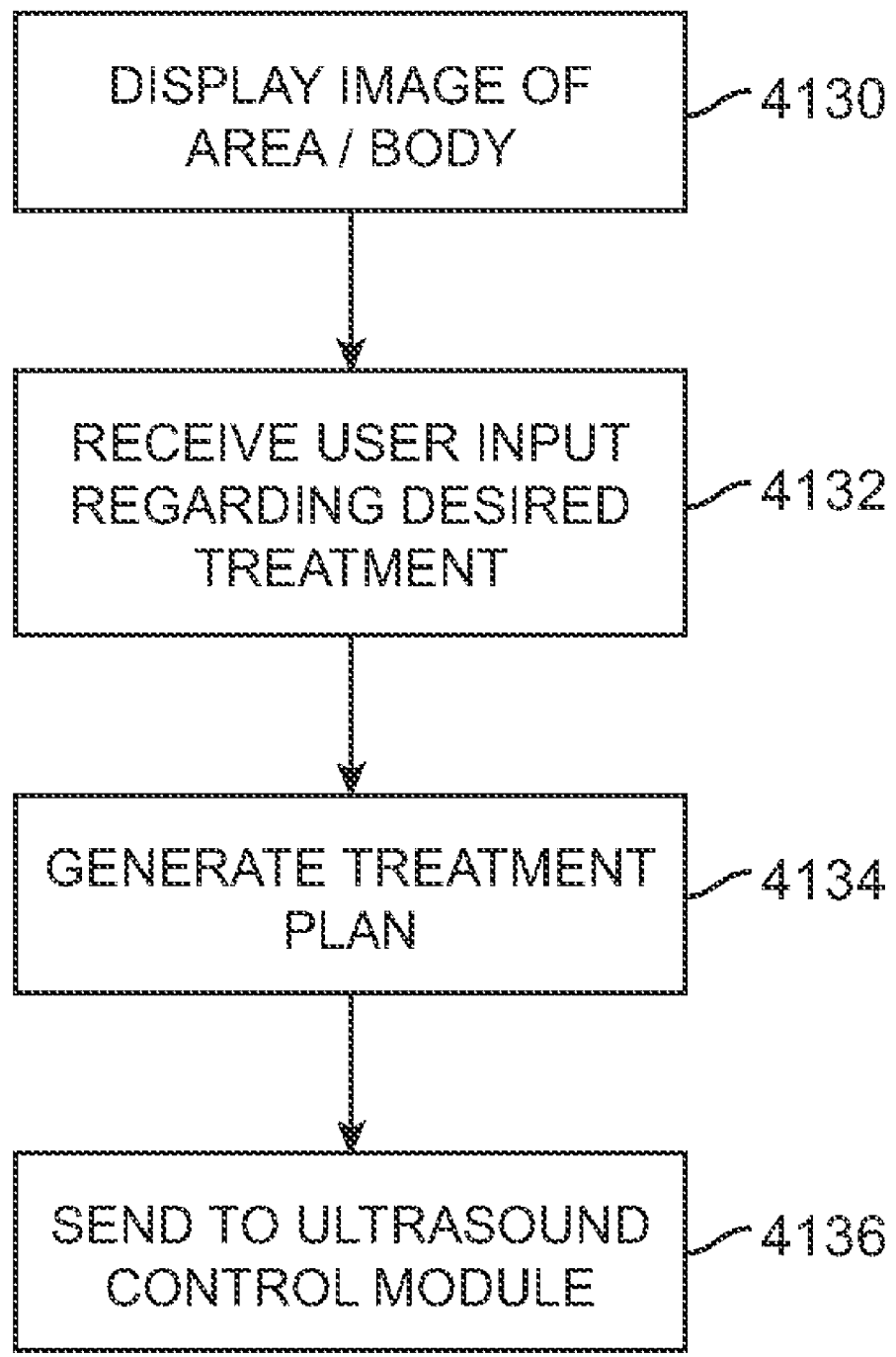
FIG. 51 shows steps for providing treatment information to a control module in accordance with embodiments.

FIG. 51 shows steps for providing treatment information to the ultrasound control module 4108 in accordance with embodiments. Beginning step 4130, an image of the body, such as the image 4116, is displayed for the user. This display may also include the contour/mapping information 4104, such as by displaying the grid 4118.

At step 4132, the system receives user input regarding a desired treatment. For example, the user may press the treat button 4112 and then run his/her finger across a portion of the screen where treatment is desired. The user may also or alternatively hit the do not treat button 4114 and then select some areas for which treatment is not desired. As an example, the user may select a rib area of a patient for not having treatment, and an area having a high percentage of subcutaneous fat for treatment.

At step 4134, a treatment plan is generated, and that treatment plan is sent to the ultrasound control module at 4136. The ultrasound control module may then utilize that information to operate the therapy head and/or ultrasound treatment device accordingly, such as by turning on and off the transducer in accordance with areas selected by the user, or causing the transducer to avoid non-treatment areas. Selective treatment of particular areas is described in more detail in the following paragraphs.

Figure 52:
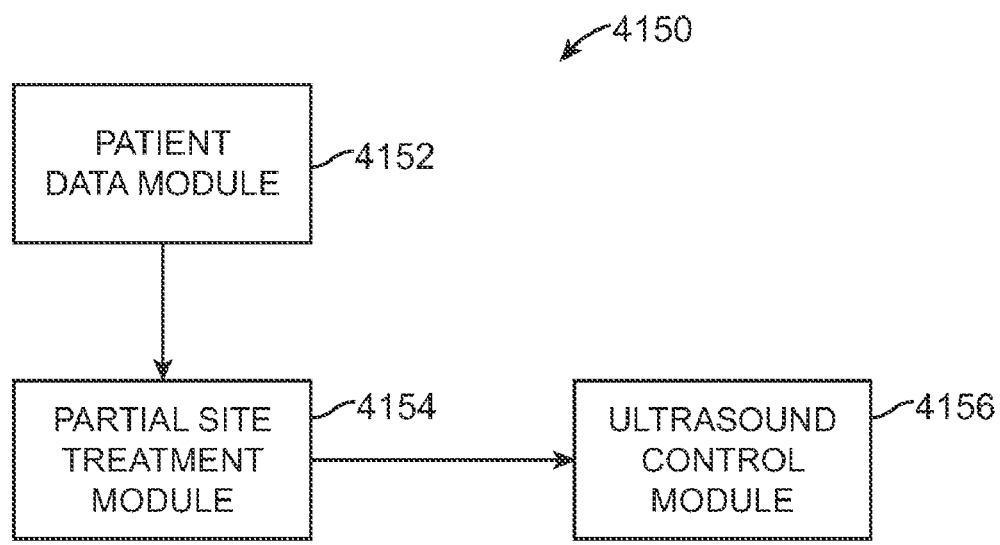
FIG. 52 illustrates a module for providing variable treatment to different areas in accordance with embodiments.

FIG. 52 schematically illustrates modules 4150 for providing variable treatment to different areas of a user in accordance with embodiments. By "variable," we mean that treatment may be given to some areas and not others, and/or more treatment or dosage may be given to some areas than others. The treatment may be variable for a single positioning of the therapy head. Thus, even though the therapy head remains stationary, areas treated while the therapy head may receive varied dosages, or no dosage at all.

A patient data module 4152 provides patient data, such as the body data 4102 and/or the contour/mapping information 4104, to a partial site treatment module 4154. The partial site treatment module generates a treatment plan and provides that treatment plan to the ultrasound control module 4156, which in turn controls the ultrasound control electronics of the device.

As an example, the therapy head may be designed to sweep over an area such as 1 inch by 1 inch, and the partial site treatment module 4154 may instruct the transducer to not move over the areas that are indicated as not having treatment and to move over and provide dosage to the areas indicated as having treatment. As an alternative, the transducer may pass over all areas, and the partial site treatment module 4154 may instruct the transducer to broadcast energy over treatment zones, and prevent the broadcast of energy over the areas that are indicated as not having treatment.

Figure 53:
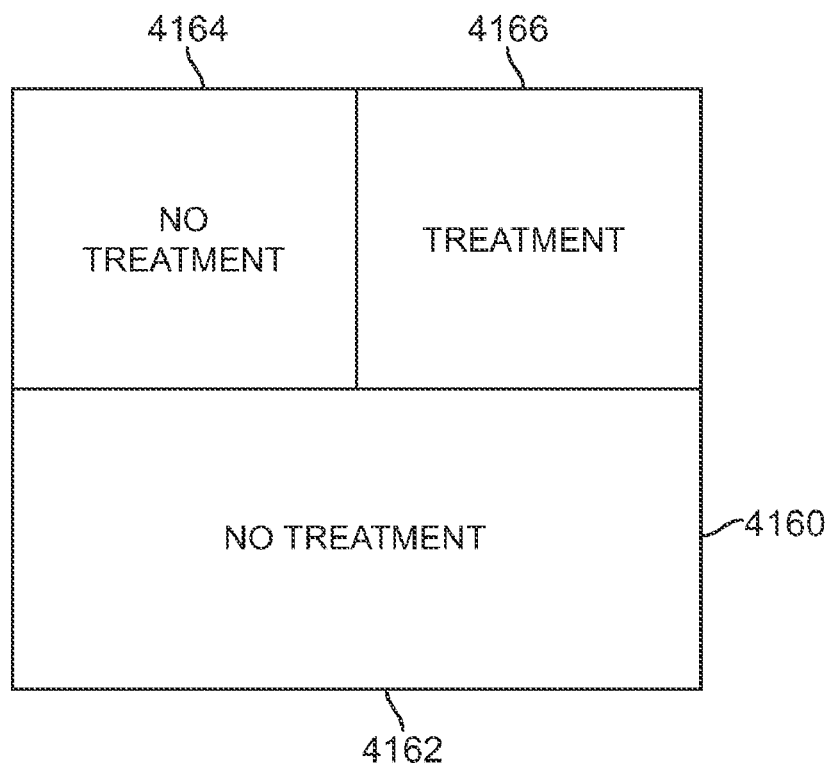
FIG. 53 shows an arrangement of broadcast zones divided into treatment and non-treatment zones.

As an example, as shown in FIG. 53, a treatment site 4160 includes two no treatment zones 4162, 4164, and a treatment zone 4166. As stated above, as the therapy head is placed over the area 4160, the transducer may either not travel to the no treatment zones 4162, 4164, or not broadcast in these zones. The therapy head will travel to and treat the treatment zone 4166.

Figure 54:
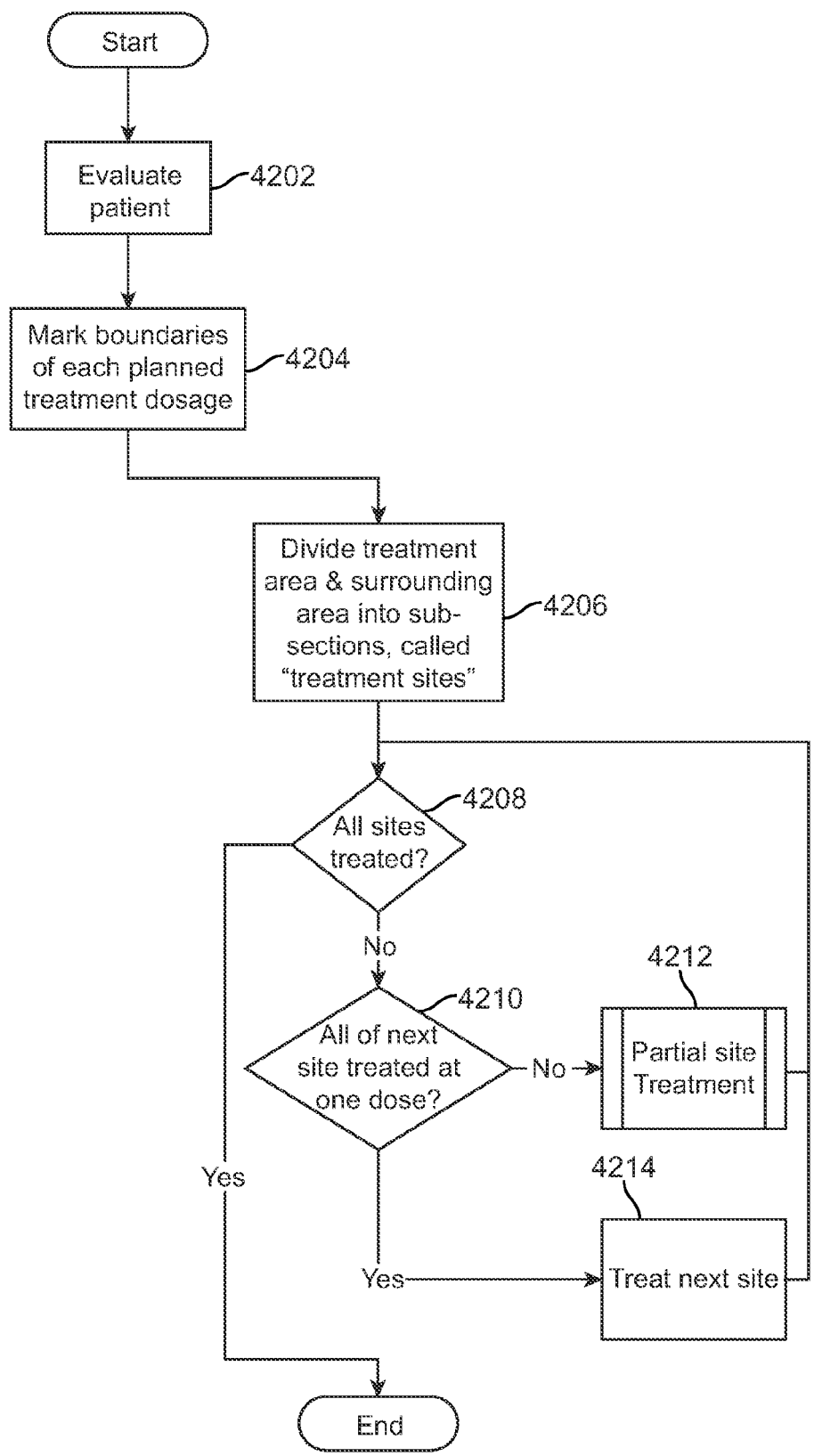
FIG. 54 shows steps for establishing a partial treatment area in accordance with embodiments.

FIG. 54 shows steps for establishing a partial treatment of an area in accordance with embodiments. The process starts at 4202, where the patient is evaluated by a medical professional. The medical professional marks boundaries of each planned treatment zone in step 4204. These boundaries may be marked on a user or may be provided via the touch screen interface as described above.

At step 4206, the treatment area is divided into treatment sites representing locations at which the therapy head will be placed. These treatment sites may represent a number of squares, which may be represented as a grid on the patient as defined above.

At step 4208, a determination is made whether all sites have been treated. If so, the process ends. If not, the process branches to step 4210, where a determination is made whether all of the next site is treated with a single dose level. If so, the process branches to step 4214, where the next site is treated. The process then branches back to step 4208. If all of the next site is not treated at one dose; i.e., part of it is treated and part of it is not, then step 4210 branches to step 4212, where partial site treatment is conducted, such as described above with respect to FIGS. 52 and 53. The process then branches back to step 4208.

It can be understood that the process described above may also be used to treat some places in the site more than others. For example, in the site 4160 shown in FIG. 53, one or more of the regions 4162, 4164, and/or 4166 may have a single dose of energy, whereas others may have two or more doses, or the dosage power may vary over boundaries. In either event, the partial site treatment module 4154 may provide appropriate instructions to the ultrasound control module 4156.

Figure 55:
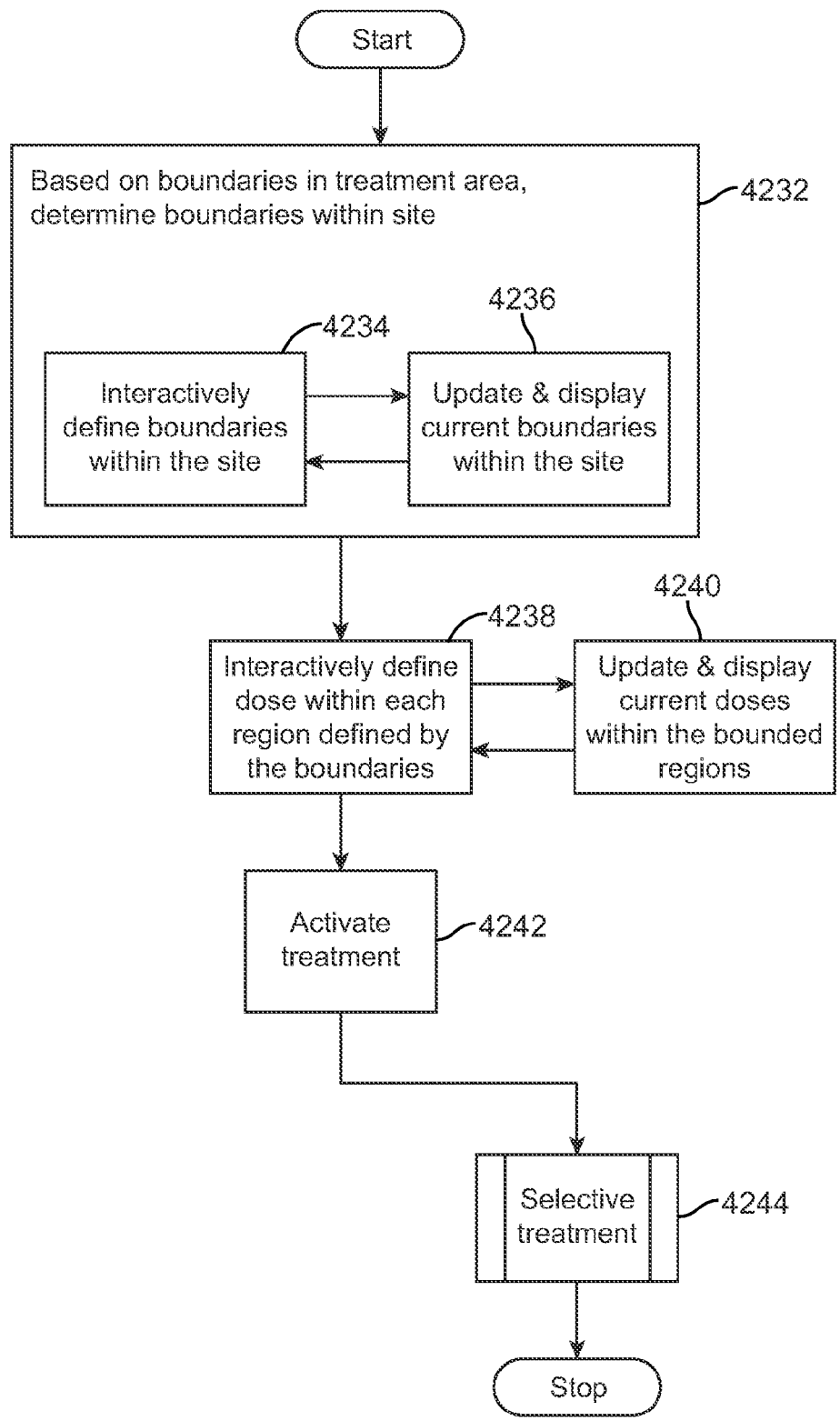
FIG. 55 shows a method for partial site treatment in accordance with embodiments.

FIG. 55 shows a method for partial site treatment in accordance with embodiments. Beginning at step 4232, based on the boundaries in the treatment area (i.e., the boundaries defined for the entire patient treatment, not just for the particular therapy head site location), the boundaries are determined for a therapy head site. This is done via steps 4234 and 4236, where the boundaries are interactively defined within the site, and then the boundaries are updated and displayed within the site. The interactive process may occur, for example, via the touch screen 4110. These boundaries form the regions within the site, such as is defined with respect to FIG. 53. At steps 4238 and 4240, the dosages within the regions defined by the boundaries are defined. This process may be done at the same time as establishing the boundaries. These dosages are interactively defined in step 4238 and updated and displayed in step 4240. At step 4242, the treatment is activated. The selected treatment occurs at step 4244.

Figure 56:
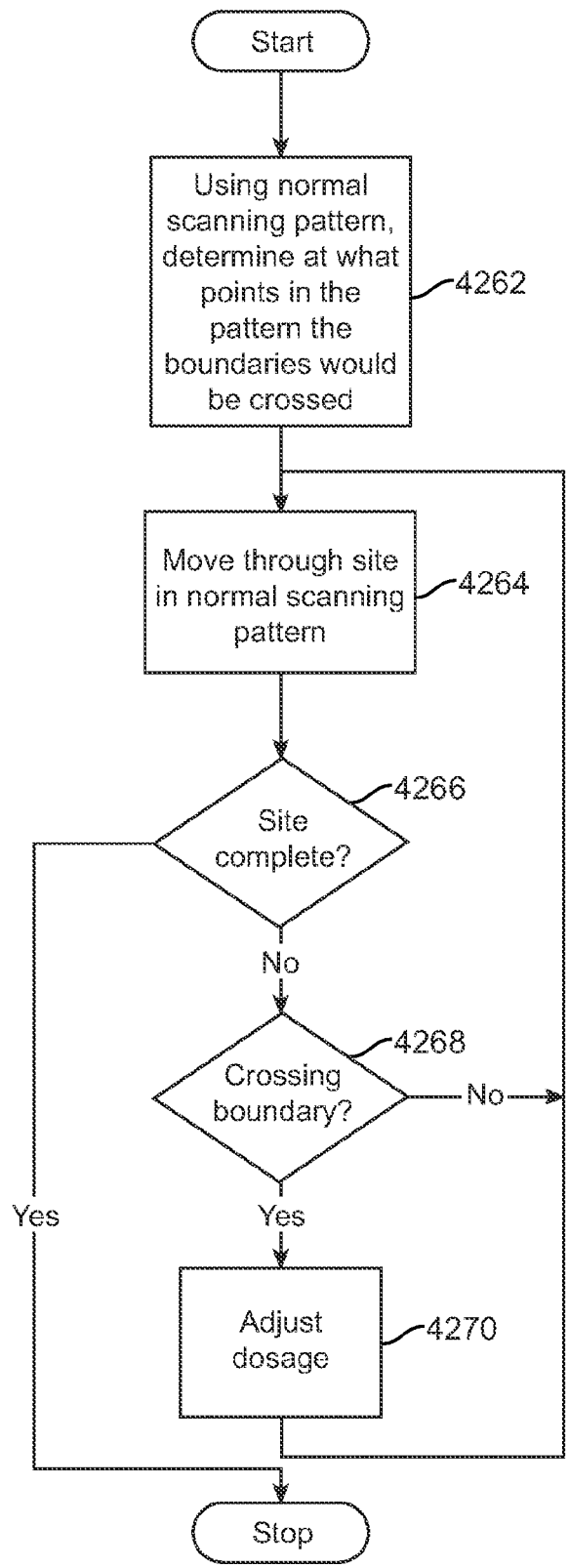
FIG. 56 shows a method for providing selective treatment at a site in accordance with embodiments.

FIG. 56 shows a method for providing selective treatment at a site in accordance with embodiments. In the methods shown in FIG. 56, the transducer moves over all locations under the therapy head, but the dosage is varied at locations, either turning the transducer off and on, or varying the dosage as desired. Beginning at step 4262, a determination is made at what points in a scanning pattern boundaries would be crossed. That is, at what points would boundaries between treatment and no treatment areas be crossed (or, as described above, varied dosage level boundaries crossed).

At step 4264, the transducer moves through the site in its normal scanning pattern (i.e., as if the entire site were to be treated). At step 4266, a determination is made whether the site is complete. If yes, the process is finished. If no, then a determination is made in step 4268 whether a boundary has been crossed. If not, the process branches back to step 4264, where the transducer continues to move through the site. If a boundary is crossed, step 4268 branches to step 4270, where the dosage from the transducer is adjusted (e.g., turned off or on, or increased or decreased, as discussed above) and the process then branches back to step 4264, where the transducer continues to scan the site.

Figure 57:
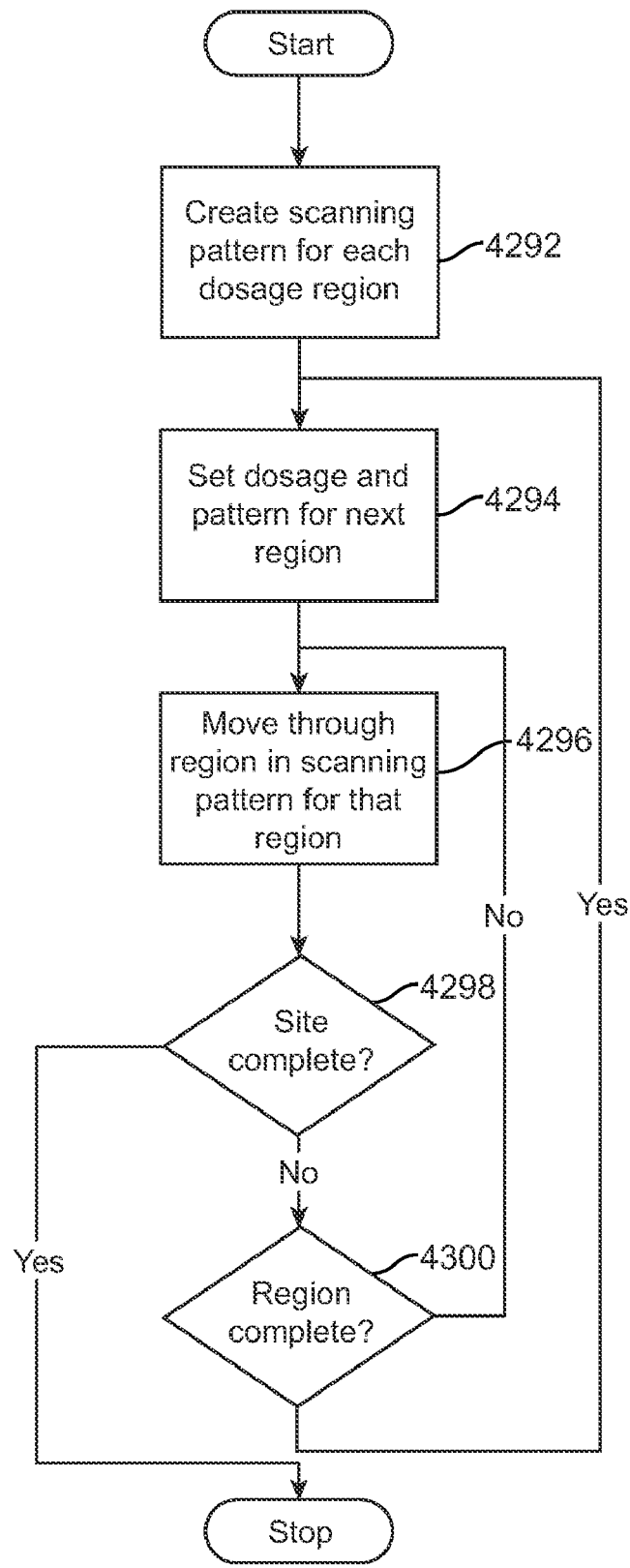
FIG. 57 shows another method of selective treatment at a therapy head site in accordance with embodiments.

FIG. 57 shows another method for selective treatment at a therapy head site in accordance with embodiments. In the methods shown in FIG. 57, the scanning pattern is varied so as to provide selective treatment. Thus, if an area is not to be treated, the transducer can skip that area. Beginning at step 4292, a scan pattern is created for each dosage region in the site. At step 4294, the dosage and pattern for the next region is set. The transducer moves through the region in a scanning pattern for that region at step 4296. At step 4298, a determination is made whether the site is complete. If yes, then the process is done. If no, then determination is made at step 4300 whether the region is complete. If no, then the process branches back to step 4296, and if yes, then the process branches back to step 4294. The process continues until the site is complete.

Other variations are within the spirit of the present invention. Thus, while the invention is susceptible to various modifications and alternative constructions, a certain illustrated embodiment thereof is shown in the drawings and has been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A liquid degas system comprising:
   a reservoir;
   a ventilation chamber within the reservoir;
   a conduit located to receive a gassed liquid from the reservoir and pass the liquid to a bottom of the ventilation chamber, said conduit having a flow restriction therein;
   a pump positioned to flow gassed liquid from the reservoir and through the flow restriction in the conduit to produce a degassed liquid and a gas which are released to the bottom of the ventilation chamber;
   a gas vent on the top of the ventilation chamber, said vent having an exit port disposed in the reservoir; and
   an outlet which receives degassed liquid from the bottom of the ventilation chamber and delivers the degassed liquid out of the ventilation chamber and reservoir.

2. The system as in claim 1, further comprising a distribution manifold within the ventilation chamber, said manifold receiving the degassed liquid and gas from the conduit and distributing such mixture throughout the ventilation chamber.

3. The system as in claim 2, wherein the distribution manifold includes side walls and a top having orifices formed therethrough.

4. The system as in claim 1, wherein the gas vent comprises a vent conduit having the exit port at a level below the top of the ventilation chamber.

5. The system as in claim 1, wherein the pump is positioned between the flow restriction and the ventilation chamber to draw liquid through the flow restriction.

6. The system of claim 5, wherein the pump draws a negative pressure in the duct between the flow restriction device and the pump in the range from about 1 PSI to 2.5 PSI absolute.

7. The system of claim 1, further comprising:
   an enclosure containing the liquid degas system;
   a cable having a proximal end and distal end, the proximal end connected to the enclosure; and
   an ultrasound therapy head connected to the distal end of the cable wherein a liquid circuit extends from the outlet through the cable into the therapy head.

8. A method of degassing a liquid, said method comprising:
   maintaining a gassed liquid in a reservoir;
   drawing the gassed liquid from the reservoir through a flow restrictor to form a mixture of degassed liquid and gas;
   passing the mixture of degassed liquid and gas into a ventilation chamber within the reservoir, wherein said mixture separates into a gas portion which rises to the top of the chamber and a degassed liquid portion which falls to a bottom of the chamber;
   venting the gas from the top of the ventilation chamber into the gassed liquid in the reservoir; and
   removing the degassed liquid portion from the bottom of the ventilation chamber.

9. The method as in claim 8, further comprising circulating the degassed liquid from the bottom of the ventilation chamber through a liquid circuit where it absorbs gas to become a gassed liquid and returning the gassed liquid to the reservoir.

10. The method as in claim 9, wherein the liquid circuit comprises a therapy head having an ultrasound transducer therein.

11. The method as in claim 10, wherein the liquid circuit further comprises a heat exchanger to cool the degassed liquid before it enters the therapy head.

12. The method of claim 8, further comprising passing the mixture of degassed liquid and gas through a distributor manifold having a plurality of orifices which create a positive pressure and restrict the flow rate of the degassed liquid.

* * * * *

UNITED STATES PATENT AND TRADEMARK OFFICE
CERTIFICATE OF CORRECTION

| | |
|---|---|
| PATENT NO. | : 8,152,904 B2 |
| APPLICATION NO. | : 12/794653 |
| DATED | : April 10, 2012 |
| INVENTOR(S) | : Jonathan K. Slobodzian et al. |

It is certified that error appears in the above-identified patent and that said Letters Patent is hereby corrected as shown below:

In the Specification:

At column 1, line number 32, change "gasses" to --gases--.

At column 2, line number 21, change "comprising" to --comprises-- and at line number 43, change "maybe" to --may be--.

At column 3, line number 30, after "23", insert --is--.

At column 7, line number 26, change "gasses" to --gases--.

At column 8, line number 58, change "provide" to --provides-- and at line number 60, change "provide" to --provides--.

At column 10, line number 49, change "system" to --systems--.

At column 14, line number 58, after "may" insert --be--.

At column 15, line number 50, change "degasses" to --degassed--.

At column 16, line number 3, change "energy . ." to --energy.-- and at line number 15, change "to help reduce" to --may reduce-- and at line number 16, change "reducing" to --may reduce-- and at line number 55, change "gasses" to --gases--.

At column 17, line number 8, change "gasses" to --gases--.

At column 19, line number 18, change "need" to --needed-- and at line number 60, change "non treatment" to --non-treatment-- and at line number 65, change "non treatment" to --non-treatment--.

Signed and Sealed this
Twenty-fourth Day of July, 2012

David J. Kappos
*Director of the United States Patent and Trademark Office*

At column 20, line number 46, after "provided", delete "on" and at line number 55, change "practices" to --practiced--.

At column 22, line number 45, change "paths" to --path--.

At column 23, line number 1, change "path" to --paths-- and at line number 31, change "gasses" to --gases-- and at line number 38, change "form" to --forms-- and at line number 60, change "gasses" to --gases--.

At column 25, line number 13, change the first occurrence of "as" to --a--.

At column 26, line number 32, change "bubble" to --bubbles--.

At column 28, line number 18, change "are" to --is--.

At column 29, line number 9, after "502", insert --that-- and at line number 48, change "are" to --is--.

At column 31, line number 1, change "circulations" to --circulation-- and at line number 29, change "gasses" to --gases--.

At column 37, line number 28, change "are" to --is--.

At column 39, line number 32, change "an" to --a--.

At column 41, line number 52, change "gasses" to --gases--.

At column 42, line number 4, change "bal" to --ball-- and at line number 19, change "effect" to --affect--.

At column 43, line number 52, change "allow" to --allows--.

At column 45, line number 36, after "aims", delete "at" and at line number 48, change "solutions" to --solution--.

At column 46, line number 56, after "system", delete ",".

At column 47, line number 14, after "form", insert --and--.

At column 48, line number 17, after "41", insert --is--.

At column 51, line number 25, change "verse" to --versus--.

At column 52, line number 8, change "control" to --controls--.

At column 54, line number 33, change "while" to --with--.

At column 56, line number 2, change "is" to --are-- and at line number 28, change "are" to --is-- and at line number 37, change "are" to --is--.